United States Patent
Keck et al.

(10) Patent No.: US 11,959,925 B2
(45) Date of Patent: *Apr. 16, 2024

(54) METHOD OF DETERMINING TOXICITY OF AN IMMUNOMODULATORY DRUG FOR USE IN HUMANS

(71) Applicant: The Jackson Laboratory, Bar Harbor, ME (US)

(72) Inventors: James Keck, Granite Bay, CA (US); Chunting Ye, Roseville, CA (US)

(73) Assignee: The Jackson Laboratory, Bar Harbor, ME (US)

( * ) Notice: Subject to any disclaimer, the term of this patent is extended or adjusted under 35 U.S.C. 154(b) by 477 days.

This patent is subject to a terminal disclaimer.

(21) Appl. No.: 16/605,753

(22) PCT Filed: Apr. 17, 2018

(86) PCT No.: PCT/US2018/027887
§ 371 (c)(1),
(2) Date: Oct. 16, 2019

(87) PCT Pub. No.: WO2018/195027
PCT Pub. Date: Oct. 25, 2018

(65) Prior Publication Data
US 2021/0132080 A1 May 6, 2021
US 2022/0003781 A9 Jan. 6, 2022

Related U.S. Application Data

(60) Provisional application No. 62/521,617, filed on Jun. 19, 2017, provisional application No. 62/486,441, filed on Apr. 17, 2017.

(51) Int. Cl.
*G01N 33/68* (2006.01)
*A01K 67/0278* (2024.01)
*C07K 16/28* (2006.01)

(52) U.S. Cl.
CPC ..... *G01N 33/6863* (2013.01); *A01K 67/0278* (2013.01); *C07K 16/2809* (2013.01); *C07K 16/2818* (2013.01); *C07K 16/2887* (2013.01); *C07K 16/2893* (2013.01); *A01K 2227/105* (2013.01); *A01K 2267/0325* (2013.01)

(58) Field of Classification Search
CPC ........... G01N 33/6863; G01N 2800/24; G01N 33/5044; G01N 33/6893; A01K 67/0278; A01K 2227/105; A01K 2267/0325; A01K 2207/12; A01K 2217/15; A01K 67/0271; C07K 16/2809; C07K 16/2818; C07K 16/2887; C07K 16/2893
See application file for complete search history.

(56) References Cited

U.S. PATENT DOCUMENTS

| 7,105,158 B1 | 9/2006 | D'Souza et al. |
| 2011/0082091 A1 | 4/2011 | Hunig |
| 2013/0316326 A1 | 11/2013 | Filinova |
| 2015/0007357 A1 | 1/2015 | Bouguermouh et al. |
| 2017/0172121 A1 | 6/2017 | Stevens et al. |
| 2017/0273285 A1 | 9/2017 | Murphy et al. |
| 2018/0187210 A1 | 7/2018 | Keck |
| 2022/0214330 A1 | 7/2022 | Keck et al. |

FOREIGN PATENT DOCUMENTS

| CN | 103304669 A | 9/2013 |
| CN | 104160272 A | 11/2014 |
| CN | 105452861 A | 3/2016 |
| JP | 2016-518828 A | 6/2016 |
| WO | WO 2017/040930 A2 | 3/2017 |
| WO | WO 2019/141251 A1 | 7/2019 |

OTHER PUBLICATIONS

England et al., J Nuclear Med., vol. 58, No. 1:162-168, Jan. 2017 (Year: 2017).*
Malcolm et al., Journal of Immunological Methods 384 (2012) 33-42 (Year: 2012).*
McIntosh et al., Chimerism, vol. 6, Nos. 1-2: 40-45, 2016 (Year: 2016).*
Gregoire-Gauthier et al. Bone Marrow Transplantation (2012) 47, 439-450 (Year: 2012).*
International Search Report and Written Opinion dated Jul. 31, 2018 in connection with Application No. PCT/US2018/027887.
International Preliminary Report on Patentability dated Oct. 31, 2019 in connection with Application No. PCT/US2018/027887.
Abramowicz et al., Release of tumor necrosis factor, interleukin-2, and gamma-interferon in serum after injection of OKT3 monoclonal antibody in kidney transplant recipients. Transplantation. Apr. 1989;47(4):606-8.
Brady et al., Preclinical screening for acute toxicity of therapeutic monoclonal antibodies in a hu-SCID model. Clin Transl Immunology. Dec. 1, 20149;3(12):e29, 7 pages. doi: 10.1038/cti.2014.28.
Carayol et al., Quantitative analysis of T helper 1, T helper 2, and inflammatory cytokine expression in patients after allogeneic bone marrow transplantation: relationship with the occurrence of acute graft-versus-host disease. Transplantation. May 15, 1997;63(9):1307-13.
Carson et al., A fatal cytokine-induced systemic inflammatory response reveals a critical role for NK cells. J Immunol. Apr. 15, 1999;162(8):4943-51.

(Continued)

*Primary Examiner* — Kimberly Ballard
*Assistant Examiner* — Stacey N MacFarlane
(74) *Attorney, Agent, or Firm* — Wolf, Greenfield & Sacks, P.C.

(57) ABSTRACT

Humanized mouse models and methods are provided for determining whether administration of an immunomodulatory drug likely elicits a severe cytokine release syndrome in a human. Humanized mouse models and methods are also provided for determining the immunotoxicity in a human of a drug candidate or of drug combinations.

15 Claims, 34 Drawing Sheets

(56) References Cited

OTHER PUBLICATIONS

Duff, Expert Scientific Group on Phase One Clinical Trials, Final Report. The Stationery Office. Nov. 30, 2006;1-108. https://webarchive.nationalarchives.gov.uk/20130105143109/http://www.dh.gov.uk/prod_consum_dh/groups/dh_digitalassets/@dh/@en/documents/digitalasset/dh_073165.pdf [last accessed Jan. 15, 2020].

Gogishvili et al., Rapid regulatory T-cell response prevents cytokine storm in CD28 superagonist treated mice. PLoS One. 2009;4(2):e4643, 9 pages. doi: 10.1371/journal.pone.0004643. Epub Feb. 27, 2009.

Gribble et al., Toxicity as a result of immunostimulation by biologics. Expert Opin Drug Metab Toxicol. Apr. 2007;3(2):209-34.

Hunig, Manipulation of regulatory T-cell No. and function with CD28-specific monoclonal antibodies. Adv Immunol. 2007;95:111-48.

Lee et al., Current concepts in the diagnosis and management of cytokine release syndrome. Blood. Jul. 10, 2014;124(2):188-95. doi: 10.1182/blood-2014-05-552729. Epub May 29, 2014.

Malcom et al., A humanized mouse model of cytokine release: Comparison of CD3-specific antibody fragments. J Immunol. Methods. Oct. 31, 2012;384(1-2):33-42. doi: 10.1016/j.jim.2012.07.001. Epub Jul. 11, 2012.

Nguyen et al., Loss of Siglec expression on T lymphocytes during human evolution. Proc Natl Acad Sci USA. May 16, 2006;103(20):7765-70. Epub May 8, 2006.

Schraven et al., CD28 superagonists: what makes the difference in humans? Immunity. May 2008;28(5):591-5. doi: 10.1016/j.immuni.2008.04.003.

Suntharalingam et al., Cytokine storm in a phase 1 trial of the anti-CD28 monoclonal antibody TGN1412. N Engl J Med. Sep. 7, 2006;355(10):1018-28. Epub Aug. 14, 2006.

Teachey et al., Identification of Predictive Biomarkers for Cytokine Release Syndrome after Chimeric Antigen Receptor T-cell Therapy for Acute Lymphoblastic Leukemia. Cancer Discov. Jun. 2016;6(6):664-79. doi: 10.1158/2159-8290.CD-16-0040. Epub Apr. 13, 2016.

Wang et al., The cytokine storm and factors determining the sequence and severity of organ dysfunction in multiple organ dysfunction syndrome. Am J Emerg Med. Jul. 2008;26(6):711-5. doi: 10.1016/j.ajem.2007.10.031.

Weir, Hazard identification and risk assessment for biologics targeting the immune system. J Immunotoxicol. Jan. 2008;5(1):3-10. doi: 10.1080/15476910801897409.

Weißmüller et al., TGN1412 Induces Lymphopenia and Human Cytokine Release in a Humanized Mouse Model. PLoS One. Mar. 9, 2016;11(3):e0149093, 19 pages. doi: 10.1371/journal.pone.0149093.

Wing, Monoclonal antibody first dose cytokine release syndromes-mechanisms and prediction. J Immunotoxicol. Jan. 2008;5(1):11-5. doi: 10.1080/15476910801897433.

International Search Report and Written Opinion dated Dec. 27, 2021 in connection with Application No. PCT/US2021/051734.

Adigbli et al., Development of LT-HSC-Reconstituted Non-Irradiated NBSGW Mice for the Study of Human Hematopoiesis In Vivo. Front Immunol. Mar. 25, 2021;12:642198. doi: 10.3389/fimmu.2021.642198.

Ali et al., Xenogeneic graft-versus-host-disease in NOD-scid IL-2Rγnull mice display a T-effector memory phenotype. PLoS One. 2012;7(8):e44219. doi: 10.1371/journal.pone.0044219. Epub Aug. 28, 2012.

Brehm et al., Engraftment of human HSCs in nonirradiated newborn NOD-scid IL2rγ null mice is enhanced by transgenic expression of membrane-bound human SCF. Blood. Mar. 22, 2012;119(12):2778-88. doi: 10.1182/blood-2011-05-353243. Epub Jan. 12, 2012.

Futrega et al., Direct bone marrow HSC transplantation enhances local engraftment at the expense of systemic engraftment in NSG mice. Sci Rep. Apr. 11, 2016;6:23886. doi: 10.1038/srep23886.

Jin et al., Modeling anti-CD19 CAR T cell therapy in humanized mice with human immunity and autologous leukemia. EBioMedicine. Jan. 2019;39:173-181. doi: 10.1016/j.ebiom.2018.12.013. Epub Dec. 20, 2018.

King et al., Human peripheral blood leucocyte non-obese diabetic-severe combined immunodeficiency interleukin-2 receptor gamma chain gene mouse model of xenogeneic graft-versus-host-like disease and the role of host major histocompatibility complex. Clin Exp Immunol. Jul. 2009;157(1):104-18. doi: 10.1111/j.1365-2249.2009.03933.x.

Pearson et al., Creation of "humanized" mice to study human immunity. Curr Protoc Immunol. May 2008;Chapter 15:Unit 15.21. doi: 10.1002/0471142735.im1521s81. Author Manuscript, 28 pages.

Ponomaryov et al., Induction of the chemokine stromal-derived factor-1 following DNA damage improves human stem cell function. J Clin Invest. Dec. 2000;106(11):1331-9. doi: 10.1172/JCI10329.

Ratajczak et al., Emerging Strategies to Enhance Homing and Engraftment of Hematopoietic Stem Cells. Stem Cell Rev Rep. Feb. 2016;12(1):121-8. doi: 10.1007/s12015-015-9625-5.

Singh et al., An improved protocol for efficient engraftment in NOD/LTSZ-SCIDIL-2Rγnull mice allows HIV replication and development of anti-HIV immune responses. PLoS One. 2012;7(6):e38491. doi: 10.1371/journal.pone.0038491. Epub Jun. 4, 2012.

Sterner et al., GM-CSF inhibition reduces cytokine release syndrome and neuroinflammation but enhances CAR-T cell function in xenografts. Blood. Feb. 14, 2019;133(7):697-709. doi: 10.1182/blood-2018-10-881722. Epub Nov. 21, 2018.

Ye et al., A rapid, sensitive, and reproducible in vivo PBMC humanized murine model for determining therapeutic-related cytokine release syndrome. FASEB J. Sep. 2020;34(9):12963-12975. doi: 10.1096/fj.202001203R. Epub Aug. 9, 2020.

Yong et al., Humanized Mice as Unique Tools for Human-Specific Studies. Arch Immunol Ther Exp (Warsz). Aug. 2018;66(4):245-266. doi: 10.1007/s00005-018-0506-x. Epub Feb. 7, 2018.

Yaguchi et al., Human PBMC-transferred murine MHC class I/II-deficient NOG mice enable Long-term evaluation of human immune responses. Cell Mol Immunol. Nov. 2018; 15(11):953-962. doi: 10.1038/cmi.2017.106. Epub Nov. 20, 2017.

Kim et al., Humanized mice for studying human leukocyte integrins in vivo. Methods Mol Biol. 2012;757:509-21. doi: 10.1007/978-1-61779-166-6_30. Author Manuscript, 13 pages.

Inoue et al., Safety evaluation of biotechnology-derived pharmaceuticals. Drug Deliv System. 2011;26-6:622-27.

* cited by examiner

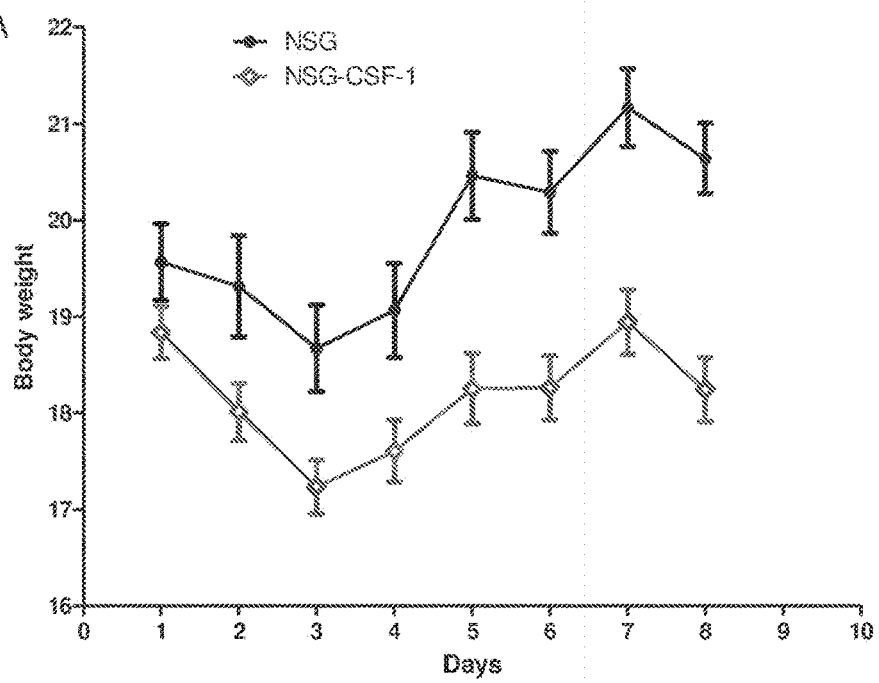
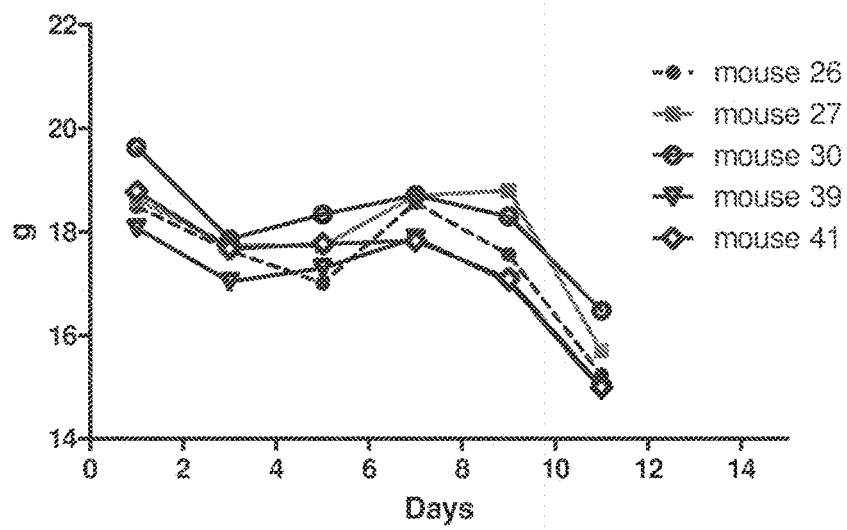

FIG. 4B

| ID | Age | Gender | Race | Weight (lbs) | AOB type | CD3 % | CD19 % | CD14 % | CD11C % | CD16 % | CD56 % | HLA-A Allele 1 2 | HLA-B Allele 1 2 | HLA-C Allele 1 2 | HLA-DRB1 Allele 1 2 |
|---|---|---|---|---|---|---|---|---|---|---|---|---|---|---|---|
| 362 | 20 | M | Caucasian | 120 | B | 74.3 | 4.8 | 15.4 | 19.7 | 5.8 | 4.5 | 01 23 | 40 49 | 03 07 | 03 11 |
| 366 | 49 | M | Caucasian | 176 | A | 83.3 | 8.5 | 5.7 | 9.0 | 3.9 | 6.9 | 0201 6801 | 35 40 | 03 04 | 04 15 |
| 345 | 39 | M | Caucasian | 250 | O | 49.9 | 3.3 | 28.2 | 39.8 | 16.5 | 6.5 | 31 32 | 07 40 | 03 07 | 04 15 |
| 213 | 25 | F | Caucasian | 210 | O | 66.3 | 10.4 | 26.7 | 34.5 | 11.5 | 10.5 | 02 02 | 35 56 | 01 04 | 11 01 |
| 364 | 65 | F | Caucasian | 189 | O | 63.3 | 8.1 | 18.4 | 23.2 | 10.4 | 6.5 | 11 26 | 35 45 | 04 17 | 11 103 |
| 353 | 21 | M | African-American | 285 | O | 32.5 | 14.4 | 33 | 51 | 15.5 | 9 | 0201 23 | 0702 5802 | 06 07 | 09 13 |
| 309 | 22 | F | Caucasian | 145 | A | 65 | 14.4 | 12.9 | 20.2 | 6.7 | 7.4 | 01 24 | 07 15 | 04 07 | 1501 1502 |
| A4692 | | | | | | 59.3 | 6.7 | | | | 26.5 | 0207 2901 | 0705 5701 | 0602 1505 | 0701 1001 |

FIG. 6

| Donor | IFN-γ | | IL-10 | |
|---|---|---|---|---|
| | OKT3 | Anti-CD28 | OKT3 | Anti-CD28 |
| A4692 | > | > | > | > |
| A4625 | > | + | > | + |
| A4668 | > | > | > | > |
| 362 | > | > | > | > |
| 366 | > | + | > | + |
| 345 | > | + | > | + |
| 213 | > | + | > | + |
| 364 | + | - | + | - |
| 353 | + | - | + | - |
| 309 | > | + | > | + |

\>: IFN-γ ≥ 1,800 pg/ml or IL-10 ≥ 120 pg/ml

+: 300 pg/ml ≤ IFN-γ < 1,800 pg/ml or 25 pg/ml ≤ IL-10 < 120 pg/ml

- : IFN-γ < 300 pg/ml or IL-10 < 25 pg/ml

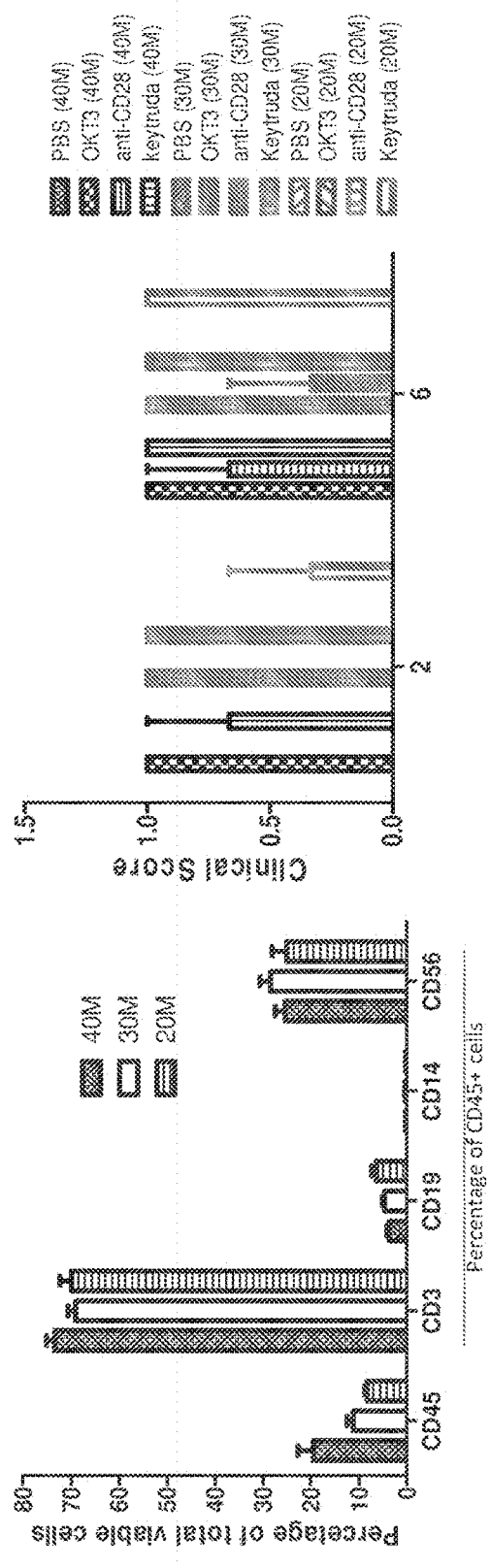
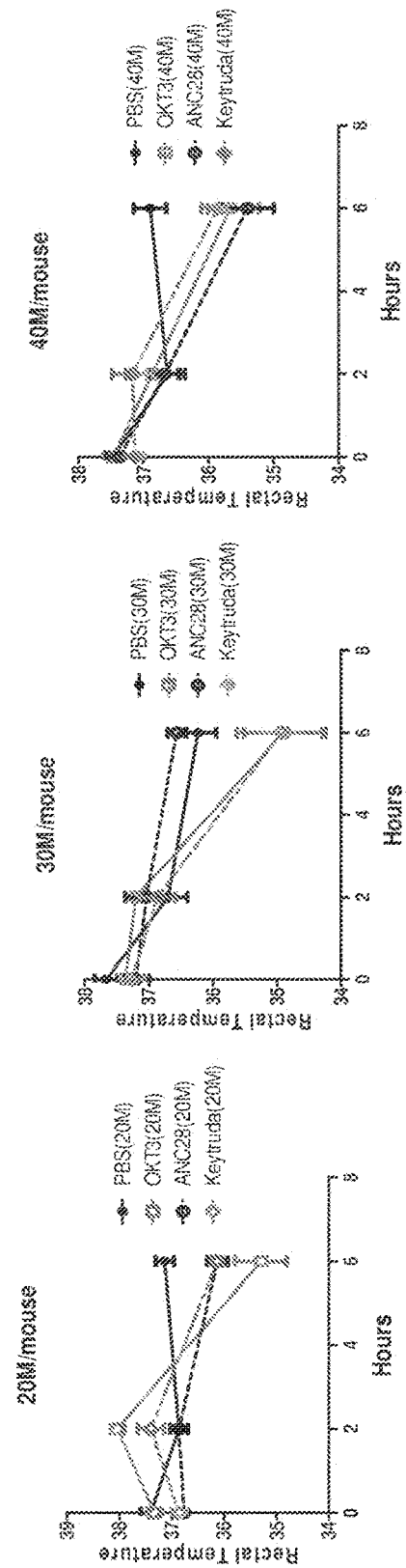

METHOD OF DETERMINING TOXICITY OF AN IMMUNOMODULATORY DRUG FOR USE IN HUMANS

CROSS-REFERENCE TO RELATED APPLICATIONS

This application is a national stage filing under 35 U.S.C. § 371 of international application number PCT/US2018/027887, filed Apr. 17, 2018, which was published under PCT Article 21(2) in English and claims the benefit under 35 U.S.C. § 119(e) of U.S. provisional application No. 62/486,441, filed Apr. 17, 2017, and U.S. provisional application No. 62/521,617, filed Jun. 19, 2017, each of which is herein incorporated by reference in its entirety.

FIELD OF THE INVENTION

The present invention generally relates to a method of determining if an immunomodulatory drug elicits a cytokine release syndrome response in a human to whom the immunomodulatory drug is administered. The present invention also provides an in vivo mouse method that has a predictive value for use in pharmaceutical safety evaluations of a drug candidate.

BACKGROUND OF THE INVENTION

Monoclonal antibodies (mAbs) have been used therapeutically in the treatment of cancer and autoimmune diseases. Many of these therapeutic mAbs are targeted against proteins on the surface of immune cells, especially T-cells and B-cells. However, mAbs can have a variety of adverse effects at the time of infusion, such as cytokine release syndrome (CRS), or systemic inflammatory response syndrome (SIRS), which can be lethal. CRS clinically manifests when large numbers of lymphocytes (B cells, T cells, and/or natural killer (NK) cells) and/or myeloid cells (macrophages, dendritic cells, and monocytes) become activated by the administered mAbs and release inflammatory cytokines. Timing of symptom onset and CRS severity depends on the types of mAbs and the magnitude of immune cell activation.

There are generally two existing methods for toxicity testing prior to clinical trials of a drug, in vivo testing in animal models and in vitro whole-blood or peripheral blood mononuclear cell (PBMC) assays. Unfortunately, these two methods cannot properly predict or determine the toxicity, especially the immune toxicity in humans. In vitro testing cannot mimic the human patient body; the systemic response to potential drug toxicity cannot be modeled in any models other than in vivo. The genomic responses in rodent and non-human primate's models may not mimic human response. There is a significant gap between pre-clinical testing and clinical trials in terms of toxicity.

Methods have been attempted to graft human stem cells into a non-human mammal for testing. However, such methods suffer major problems with regard to obtaining non-embryonic stem cells from a patient (e.g., obtaining bone marrow from the patient), and are also disadvantageous in that they take too much time waiting for the stem cells to grow and differentiate into various cells. Thus, such methods are invasive (if possible at all), cumbersome, and impractical.

TGN1412, developed by the now defunct TeGenero A G, Wurzburg, is a humanized monoclonal antibody (mAb) of the $IgG_4$ subclass specific for the costimulatory molecule CD28 expressed by human T-cells. It is called a "CD28 superagonist" (CD28SA) because unlike the classic CD28-specific mAb, it can activate T-lymphocytes without simultaneous engagement of the T-cell antigen receptor (TCR) (Hunig, 2007, Adv Immunol 95: 111-148).

During a first-in-man trial conducted by the independent Parexel Clinical Trial Unit at Northwick Park Hospital, London, on Mar. 13, 2006, intravenous application of 100 µg/kg body weight of TGN1412 to healthy human volunteers led to a life-threatening cytokine release syndrome that was only controlled after transfer of the volunteers to the hospital's intensive care unit (Suntharalingam et al., 2006, Engl J Med 355: 1018-1028). Thus, the anti-CD28 immunomodulatory drug TGN1412 horribly failed in its phase I trial due to cytokine storm occurring in the subjects being tested, which severely threatened the life of six healthy volunteers involved, all six suffering from multiple organ failure.

The pre-clinical work in that study, however, showed no evidence for such a "cytokine storm" in an analogous rat model using a rat-CD28-specific superagonist, and in cynomolgus monkeys (*Macaca fascicularis*) receiving TGN1412 itself at up to 50-fold higher doses than the human volunteers (Duff, 2006, Expert Scientific Group on Phase One Clinical Trials Final Report. Norwich, UK: Stationary Office). Furthermore, addition of TGN1412 to cultures of human PBMCs did not result in cytokine release. All key monkey and PBMC culture experiments were repeated by the British National Institute for Biological Standards and Control (NIBSC) acting on behalf of the government's Expert Scientific Group on Phase One Clinical Trials, and confirmed the innocuous behavior of TGN1412 in these systems (Duff, 2006). Thus, these rat, cynomolgus, and cultured human PBMC assays were not adequate to warn against the cytokine storm experienced by the human volunteers. The failure of rodents and cynomolgus monkeys to release toxic systemic cytokines after injection of CD28SA may be due to interspecies differences in the reactivity of the intact immune system to such agents, and specific suggestions for such differences have been made. (Gogishvili et al., 2009, PLoS ONE 4(2): e4643. https://doi.org/10.1371/journal.pone.0004643; Nguyen et al., 2006, Proc Natl Acad Sci USA. 103:7765-7770; Schraven and Kalinke, 2008, Immunity 28: 591-595).

A human has roughly $1\times10^{12}$ T-lymphocytes, and less than one percent of these cells are circulating in the blood at any given moment. It is presently unknown whether failure of cultured PBMCs to respond to TGN1412 is due to a functional defect in these cells as compared to those residing in lymphoid tissues (which obviously responded with cytokine release in the volunteers), or due to the requirement of a cell type present in lymphoid organs but not in blood for TGN1412-mediated activation of T-lymphocytes.

The failure of known human PBMC cultures to respond to soluble TGN1412 with cytokine release indicates that this system does not respond to all lymphocyte-activating agents in the same manner as does the intact human immune system inside the body. Correction of this defect may not only allow a detailed analysis of the effects of human CD28 superagonists (SA) such as TGN1412, but may also reveal the reactivity of other, seemingly innocuous drugs during pre-clinical development.

Thus, there is a continuing need for a new in vivo humanized animal model effective for toxicity testing of immunomodulatory drugs and for determining toxicities such as cytokine release syndrome in individuals prior to patient treatment and clinical trials.

SUMMARY OF THE INVENTION

According to non-limiting example embodiments, the present invention provides a method of determining whether an immunomodulatory drug likely elicits a severe cytokine release syndrome in a human following administration of the immunomodulatory drug. According to example embodiments, the present method includes:
(a) providing an immunodeficient mouse, said mouse is irradiated with 75-125 cGy X-ray;
(b) engrafting $1.5\text{-}3.0 \times 10^7$ peripheral blood mononuclear cells (PBMCs) isolated from a human to said mouse;
(c) administering to said mouse an immunomodulatory drug 5-7 days after engrafting with the PBMCs;
(d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and
(e) determining said immunomodulatory drug likely elicits a severe cytokine release syndrome in said human, wherein presence of a severe cytokine release syndrome in said mouse is indicative that administration of said immunomodulatory drug likely elicits a severe cytokine release syndrome in said human.

According to another example embodiment, there provides a method of determining whether a combination of a first immunomodulatory drug and a second immunomodulatory drug likely elicits a severe cytokine release syndrome in a human following administration of said combination of immunomodulatory drugs. The method includes:
(a) providing an immunodeficient mouse, said mouse is irradiated with 75-125 cGy X-ray;
(b) engrafting $1.5\text{-}3.0 \times 10^7$ peripheral blood mononuclear cells (PBMCs) isolated from a human to said mouse;
(c) administering to said mouse a first immunomodulatory drug and a second immunomodulatory drug 5-7 days after engrafting with the PBMCs;
(d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and
(e) determining said combination of immunomodulatory drugs likely elicits a severe cytokine release syndrome in said human, wherein presence of a severe cytokine release syndrome in said mouse is indicative that administration of said combination of immunomodulatory drugs likely elicits a severe cytokine release syndrome in said human.

According to other example embodiments, the present invention provides a method of determining a safe dosage of an immunomodulatory drug that elicits no cytokine release syndrome in a human following administration of the immunomodulatory drug. In an embodiment, the method comprises:
(a) providing an immunomodulatory drug having a first dosage, said first dosage of the immunomodulatory drug is determined to elicit a mild or severe cytokine release syndrome in a first humanized irradiated immunodeficient mouse following its administration;
(b) providing a second immunodeficient mouse, said second mouse is irradiated with 75-125 cGy X-ray;
(c) engrafting $1.5\text{-}3.0 \times 10^7$ peripheral blood mononuclear cells (PBMCs) isolated from a human to said second mouse;
(d) administering to said second mouse an immunomodulatory drug 5-7 days after engrafting with the PBMCs, said immunomodulatory drug is administered at a second dosage that is lower than said first dosage;
(e) determining blood concentration in said second mouse of a plurality of cytokines comprising IFN-γ and IL-10; and
(f) determining a safe dosage of said immunomodulatory drug for administration in said human, said safe dosage is a dosage producing a blood concentration of IFN-γ is <300 pg/ml and IL-10 is <25 pg/ml following administration of said immunomodulatory drug to said second mouse,
wherein blood concentration of IFN-γ<300 pg/ml and IL-10<25 pg/ml in said second mouse is indicative that administration of said safe dosage of said immunomodulatory drug likely elicits no cytokine release syndrome in said human.

According to other example embodiments, the present invention provides a method of determining immunotoxicity of a drug candidate for use in a human. In an embodiment, the method comprises:
(a) providing an immunodeficient mouse, said mouse is irradiated with 75-125 cGy X-ray;
(b) engrafting $4.5\text{-}5.5 \times 10^7$ of human PBMCs to said mouse;
(b) administering a drug candidate to said mouse 4-7 days after engrafting;
(c) determining cytokine concentration in blood of said mouse, wherein said cytokine is at least one cytokine selected from the group consisting of IFN-γ, IL-2, IL-4, IL-6, IL-10, and TNF; and
(d) determining immunotoxicity of said drug candidate, wherein blood concentration in said mouse of at least one cytokine selected from the group consisting of:
IFN-γ≥300 pg/ml,
IL-2≥15 pg/ml,
IL-4≥10 pg/ml,
IL-6≥10 pg/ml,
IL-10≥25 pg/ml, and
TNF≥5 pg/ml, which is indicative of an immunotoxicity of said drug candidate in a human.

In another embodiment, there provides a method of determining likelihood that administration of an immunomodulatory drug to a human will induce a severe cytokine release syndrome in the human The method comprises:
(a) providing a blood sample from a humanized irradiated immunodeficient mouse administered an immunomodulatory drug 5-7 days after engraftment with $1.5\text{-}3.0 \times 10^7$ isolated peripheral blood mononuclear cells (PBMCs) from a human; and
(b) detecting in vitro the concentration of a plurality of cytokines comprising IFN-γ and/or IL-10 present in the blood sample of the mouse, wherein a concentration of IFN-γ≥1,800 pg/ml or of IL-10≥120 pg/ml is indicative that administration of the immunomodulatory drug to the human is likely to induce a severe cytokine release syndrome.

In another embodiment, there provides is a method of determining likelihood that administration of a combination of a first immunomodulatory drug and a second immunomodulatory drug to a human will induce a severe cytokine release syndrome in the human. The method comprises:

(a) providing a blood sample from a humanized irradiated immunodeficient mouse administered a combination of a first immunomodulatory drug and a second immunomodulatory drug 5-7 days after engraftment with 1.5-3.0×10$^7$ isolated peripheral blood mononuclear cells (PBMCs) from a human; and (b) detecting in vitro the concentration of IFN-γ and/or IL-10 present in the blood sample of the mouse, wherein a concentration of IFN-γ≥1,800 pg/ml or of IL-10≥120 pg/ml is indicative that administration of the combination of the first immunomodulatory drug and the second immunomodulatory drug to the human is likely to induce a severe cytokine release syndrome.

In another embodiment, there provides a method of determining immunotoxicity of a drug candidate in a human. The method comprises:

(a) providing a blood sample from a humanized, irradiated, immunodeficient mouse administered a drug candidate 4-7 days after engraftment with 4.5-5.5×10$^7$ isolated human peripheral blood mononuclear cells (PBMCs); and (b) detecting in vitro the concentration of at least one human cytokine present in the mouse blood sample to determine human immunotoxicity of the drug candidate, wherein the at least one human cytokine isselected from the group consisting of IFN-γ, IL-2, IL-4, IL-6, IL-10, and TNF and wherein the drug candidate has low human immunotoxicity when low human cytokine concentration is detected in the mouse blood sample.

BRIEF DESCRIPTION OF DRAWINGS

Non-limiting example embodiments are described herein, with reference to the following accompanying Figures:

FIG. 1A depicts NSG and NSG-CSF-1 mice body weight measurement after engraftment of human peripheral blood mononuclear cell (hPBMC) 2×10$^7$ hPBMCs/mouse. There were 10 mice per group and data are presented as mean±SEM.

FIG. 1B depicts NSG mice body weight measurement after 2×10$^7$ hPBMC/mouse engraftment. Each line represents one mouse.

FIG. 4B depicts de-identified patient donors' information before engraftment (except for donors A4625 and A4668).

FIG. 5A depicts the IFN-γ levels after induction following mAb challenges: severe/high response: ≥1,800 pg/ml; medium/mild response: 300 pg/ml≤IFN-γ<1,800 pg/ml; and low/no response: <300 pg/ml.

FIG. 5B depicts the IL-10 levels: severe/high response: ≥120 pg/ml; medium/mild response: 25 pg/ml≤IL-10<120 pg/ml; and low/no response: <25 pg/ml.

FIG. 5C depicts the IL-6 level of the humanized mice after induction of cytokines following mAb challenges.

FIG. 5D depicts the IL-2 level of the humanized mice after induction of cytokines following mAb challenges.

FIG. 5E depicts the IL-4 level of the humanized mice after induction of cytokines following mAb challenges.

FIG. 5F depicts the TNF level of the humanized mice after induction of cytokines following mAb challenges.

FIG. 6 depicts the different responses among the 10 donors receiving the administration of OKT3 or anti-CD28 mAb. After anti-CD28 mAb administration, donors A4692, A4668 and 362 responded with severe/high levels of IFN-γ and IL-10; donors A4625, 266, 345, 309 and 213 responded with medium/mild levels of IFN-γ and IL-10; and donors 364 and 353 responded with low/no levels of IFN-γ and IL-10.

FIG. 9A depicts the IFN-γ level went up above 1,800 pg/ml in 5×10$^7$ PBMCs/mouse but not in 2×10$^7$ PBMCs/mouse.

FIG. 9B depicts the IL-10 level went up above 120 pg/ml in $5\times10^7$ PBMCs/mouse but not in $2\times10^7$ PBMCs/mouse.

FIG. 9C depicts the IL-6 level with $2\times10^7$ PBMCs/mouse and $5\times10^7$ PBMCs/mouse.

FIG. 9D depicts the IL-2 level with $2\times10^7$ PBMCs/mouse and $5\times10^7$ PBMCs/mouse.

FIG. 9E depicts the IL-4 level with $2\times10^7$ PBMCs/mouse and $5\times10^7$ PBMCs/mouse.

FIG. 9F depicts the TNF level with $2\times10^7$ PBMCs/mouse and $5\times10^7$ PBMCs/mouse.

FIG. 10A depicts the INFγ level with $2\times10^7$ PBMCs/mouse, $3\times10^7$ PBMCs/mouse, and $4\times10^7$ PBMCs/mouse.

FIG. 10B depicts the IL-10 level with $2\times10^7$ PBMCs/mouse, $3\times10^7$ PBMCs/mouse, and $4\times10^7$ PBMCs/mouse.

FIG. 10C depicts the IL-6 level $2\times10^7$ PBMCs/mouse, $3\times10^7$ PBMCs/mouse, and $4\times10^7$ PBMCs/mouse.

FIG. 10D depicts the IL-2 level $2\times10^7$ PBMCs/mouse, $3\times10^7$ PBMCs/mouse, and $4\times10^7$ PBMCs/mouse.

FIG. 10E depicts the IL-4 level $2\times10^7$ PBMCs/mouse, $3\times10^7$ PBMCs/mouse, and $4\times10^7$ PBMCs/mouse.

FIG. 10F depicts the TNF level $2\times10^7$ PBMCs/mouse, $3\times10^7$ PBMCs/mouse, and $4\times10^7$ PBMCs/mouse.

FIGS. 11A-11D depict the body temperature and clinical score changes in response to OKT3, anti-CD28 and KEYTRUDA® (pembrolizumab) in donor 309 PBMC humanized mice.

FIG. 11A depicts donor 309 mice cell population on day 5. Five NSG mice were engrafted with $2\times10^7$ hPBMC/mouse; five NSG mice were engrafted with $3\times10^7$ hPBMC/mouse, and five NSG mice were engrafted with $4\times10^7$ hPBMC/mouse. All mice were engrafted 4 hours after 100cGy X-ray irradiation. Mice were bled on day 5 for CD45, CD3, CD19, CD14 and CD56 cell population testing by flow cytometry.

FIG. 11B depicts the clinical score of humanized mice at 2 and 6 hours after injection of the drug: control PBS, 0.5 mg/kg OKT3, 1 mg/kg anti-CD28, or 10 mg/kg KEYTRUDA® (pembrolizumab). The clinical score was evaluated with the following criteria: Score: 0=normal activity; 1=normal activity, piloerection, tiptoe gait; 2=hunched, reduced activity but still mobile; 3=hypomotile but mobile when prompted; 4=moribund. 5 mice/group and data are presented as mean±SEM.

FIG. 11C shows rectal temperatures that were measured using $2\times10^7$ hPMBCs/mouse with donor 309. Mice were injected with control PBS, 0.5 mg/kg OKT3, 1 mg/kg anti-CD28 or 10 mg/kg KEYTRUDA® (pembrolizumab). The rectal temperature was measured at 2 and 6 hours after drugs injection. 3-5 mice/group and data are presented as mean±SEM.

FIG. 11D shows rectal temperatures that were measured using $3\times10^7$ hPMBCs/mouse with donor 309. Mice were injected with control PBS, 0.5 mg/kg OKT3, 1 mg/kg anti-CD28 or 10 mg/kg KEYTRUDA® (pembrolizumab). The rectal temperature was measured at 2 and 6 hours after drugs injection. 3-5 mice/group and data are presented as mean±SEM.

FIG. 11E shows rectal temperatures that were measured using $4\times10^7$ hPMBCs/mouse with donor 309. Mice were injected with control PBS, 0.5 mg/kg OKT3, 1 mg/kg anti-CD28 or 10 mg/kg KEYTRUDA® (pembrolizumab). The rectal temperature was measured at 2 and 6 hours after drugs injection. 3-5 mice/group and data are presented as mean±SEM.

FIGS. 12A-12F depict the dose effect of KEYTRUDA® (pembrolizumab) in the induction of different cytokines levels with different doses of KEYTRUDA®. NSG mice were engrafted $3\times10^7$ hPBMCs/mouse of donor 358 six days before KEYTRUDA® dosing. At the day of dose, mice were iv injected with PBS, 0.5 mg/kg OKT3, 2.5 mg/kg, 5 mg/kg and 10 mg/kg KEYTRUDA®. Mice were bled at 2 and 6 hours and circulating cytokine concentrations were measured by BD CBA Th1/Th2 II kit. 5 mice/group and data are presented as mean±SEM.

FIG. 12A depicts the INFγ level with $3\times10^7$ PBMCs/mouse.

FIG. 12B depicts the IL-10 level with $3\times10^7$ PBMCs/mouse.

FIG. 12C depicts the IL-6 level with $3\times10^7$ PBMCs/mouse.

FIG. 12D depicts the IL-2 level with $3\times10^7$ PBMCs/mouse.

FIG. 12E depicts the IL-4 level with $3\times10^7$ PBMCs/mouse.

FIG. 12F depicts the TNF level with $3\times10^7$ PBMCs/mouse.

FIG. 13A depicts donor 358 mice cell population on day 5. Four (4) NSG mice were engrafted with $3\times10^7$ hPBMC 4 hours after 100cGy X-ray irradiation. Mice were bled on day 5 for CD45, CD3, CD19, CD14, and CD56 cell population testing by flow cytometry.

FIG. 13B depicts humanized mice clinical score after injection of the drugs. After 2 and 6 hours of PBS, 0.5 mg/kg OKT3, 2.5 mg/kg, 5 mg/kg and 10 kg/mg KEYTRUDA® (pembrolizumab), the clinical score was evaluated with following criteria: Score: 0=normal activity; 1=normal activity, piloerection, tiptoe gait; 2=hunched, reduced activity but still mobile; 3=hypomotile but mobile when prompted; 4=moribund. 5 mice/group and data are presented as mean±SEM.

FIG. 13C depicts the rectal temperature measured in humanized mice at different times. Mice were injected with control PBS, 0.5 mg/kg OKT3, 2.5 mg/kg, 5 mg/kg and 10 mg/kg KEYTRUDA® (pembrolizumab), and the rectal temperature was measured at 2 and 6 hours after drugs injection. 5 mice/group and data are presented as mean±SEM.

FIG. 14A presents histograms comparing cytokine release levels in response to anti-CD28 treatment obtained by in vitro (panels a and c) or in vivo (panels b and d) experiments with 4 different PBMC donors for IFN-γ (panels a and b) or IL-10 (panels c and d). Data are presented as mean±SEM FIG. 14B presents histograms comparing cytokine release levels in response to anti-CD28 treatment obtained by in vitro (panels e and g) or in vivo (panels f and h) experiments with 4 different PBMC donors for IL6 (panels e and f) or IL-4 (panels g and h). Data are presented as mean±SEM.

FIG. 22A presents graphs of level of IFN-γ(panel a), IL-10 (panel b), and IL-6 (panel c).

FIG. 22B presents graphs of level of IL-2 (panel d), IL-4 (panel e), and TNF (panel f).

DETAILED DESCRIPTION OF THE INVENTION

Figure 2A:
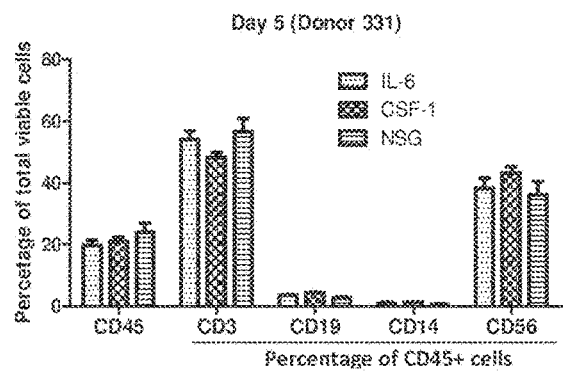
FIG. 2A depicts NSG, NSG-IL-6, and NSG-CSF-1 mice reconstitution of human PBMCs on day 5 after engraftment of 2×10$^7$ hPBMCs/mouse from donor 331. 5 mice per group and data are presented as mean±SEM.

Definitions:

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

The term "NSG" refers to the immunodeficient mouse model of NOD scid gamma (i.e., NOD.Cg-Prkdc$^{scid}$ Il2rg$^{tm1wjl}$/SzJ mice; Jackson laboratory Stock No: 005557). The mice carry two mutations on the NOD/ShiLtJ genetic background; severe combined immune deficiency (scid) and a complete null allele of the Interleukin-2 (IL2) receptor common gamma chain (IL2rgnull). These mice are extremely immunodeficient.

The term "NSG-CSF-1" refers to the NSG mouse model whose genome contains a human CSF-1 (macrophage colony-stimulating factor-1) gene and the transgenic NSG-CSF-1 mice express human CSF-1 cytokine (Jackson Laboratory Stock No: 028654).

The term "NSG-IL-6" refers to the NSG mouse model whose genome contains a human Interleukin-6 (IL-6) gene and expresses human IL-6 cytokine (Jackson Laboratory Stock No:028655).

The term "CD" refers to the Cluster of Differentiation.

The term "CD3" refers to the Cluster of Differentiation 3 and represents an antigen that is part of the T cell receptor (TCR) complex on a mature T lymphocyte.

The term "CD4" refers to the Cluster of Differentiation 4 and this antigen is a glycoprotein found on the surface of immune cells such as T helper cells, monocytes, macrophages, and dendritic cells.

The term "CD8" refers to the Cluster of Differentiation 8 and is a co-receptor is predominantly expressed on the surface of cytotoxic T cells, but can also be found on natural killer cells, cortical thymocytes, and dendritic cells.

The term "CD14" refers to the Cluster of Differentiation 14 and is an antigen expressed mainly by macrophages and dendritic cells.

The term "CD19" refers to Cluster of Differentiation 19 and this antigen is found on B-cells.

The term "CD28" refers to the Cluster of Differentiation 28 and is one of the proteins expressed on T cells that provide co-stimulatory signals required for T cell activation and survival. T-cell stimulation through CD28 in addition to the T-cell receptor (TCR) can provide a potent signal for the production of various interleukins (e.g., IL-6).

The term "CD45 cells" refers to the Cluster of Differentiation 45 and this antigen is present on human lymphocytes, monocytes and other myeloid cells.

The term "CD56" refers to the Cluster of Differentiation 56 and is a homophilic binding glycoprotein expressed on the surface of natural killer cells (NK cells).

The term "peripheral blood mononuclear cells (PBMCs)" refers to peripheral blood cells having a round nucleus. These mononuclear blood cells recirculate between tissues and blood, and are a critical component in the immune system to fight infection and adapt to intruders. There are two main types of mononuclear cells, lymphocytes and monocytes. The lymphocyte population of PBMCs typically consists of T-cells, B-cells and NK cells. PBMCs may be isolated from whole blood samples by methods well known in the art (e.g., Ficoll gradient).

The term "cytokine" refers to a member of a class of small proteins (~5-20 kDa) that are important in cell signaling. Cytokines include chemokines, interferons, interleukins, lymphokines, and tumor necrosis factors. Examples of cytokines include IFN-γ, IL-2, IL-4, IL-6, IL-10, and TNFα. Cytokines are produced by a broad range of cells, including immune cells like macrophages, B lymphocytes, T lymphocytes, and mast cells; a given cytokine may be produced by more than one type of cell. Their release has an effect on the behavior of the cells around them. Cytokines have been identified as involved in autocrine signaling, paracrine signaling, and endocrine signaling as immunomodulating agents.

The terms "cytokine release syndrome" ("CRS") is used interchangeably herein with "systemic inflammatory response syndrome" ("SIRS"), "cytokine cascade", "hypercytokinemia", and "cytokine storm." "Cytokine storm", which is also known as "hypercytokinemia" in the art defines a systemic inflammatory response in a patient inter alia characterized by hypotension, pyrexia and/or rigors, and potentially resulting in death. A cytokine storm is presumably caused by an uncontrolled positive feedback loop between cytokines and immune cells, resulting in highly elevated levels of various cytokines. While these terms may differ some in degree, they are all the result of unacceptably high release of cytokines by a subject, as a result of administration of certain antibodies to the subject. The subject reacts to the treatment by releasing the unacceptably high levels of cytokine. Referring to one of these terms herein is intended to encompass all of the terms.

The term "Grading of cytokine release syndrome (CRS)" is based on that defined by Daniel W. Lee, et al., "Current Concepts in the Diagnosis and Management of Cytokine Release Syndrome", Blood. 2014 Jul. 10; 124(2): 188-195: Grade 1: symptoms are not life threatening and require symptomatic treatment only (e.g., fever, nausea, fatigue, headache, myalgias, malaise); Grade 2: symptoms require and respond to moderate intervention, Oxygen requirement <40%, or hypotension responsive to fluids or low dose of one vasopressor, or Grade 2 organ toxicity; Grade 3: symptoms require and respond to aggressive intervention, Oxygen requirement ≥40%, or hypotension requiring high dose or multiple vasopressors, or Grade 3 organ toxicity or grade 4 transaminitis; Grade 4: Life-threatening symptoms, Requirement for ventilator support, or Grade 4 organ toxicity (excluding transaminitis); Grade: 5 Death. For purpose of this application, severe CRS refers to Grades 4-5 and mild CRS encompasses Grades 1-3.

The present inventors have determined that the concentrations of certain cytokines released in the humanized mouse models in response to an administered drug or drug candidate can be used to predict relative severity of cytokine release syndrome to be expected in a human in response to the administered drug or drug candidate. The inventors have determined, for immunodeficient mice engrafted with 1.5-3.0×10$^7$ PBMCs from a human, threshold values for mouse blood concentration of certain cytokines to determine severity of cytokine release induced in the mouse by a drug administered to the mouse 5-7 days after engraftment. The threshold values are summarized in the following table.

TABLE 1

Threshold values to determine severity of cytokine release induced by a drug administered to an immunodeficient mouse engrafted with 1.5-3.0 × 10$^7$ hPBMCs

| Cytokine | Severe/high response | Medium/mild response | Low/no response |
|---|---|---|---|
| IFN-γ | ≥1,800 pg/ml | 300 pg/ml to <1,800 pg/ml | <300 pg/ml |
| IL-10 | ≥120 pg/ml | 25 pg/ml to <120 pg/ml | <25 pg/ml |
| IL-6 | ≥25 pg/ml | 10 pg/ml to <25 pg/ml | <10 pg/ml |
| IL-2 | ≥80 pg/ml | 15 pg/ml to <80 pg/ml | <15 pg/ml |
| IL-4 | ≥25 pg/ml | 10 pg/ml to <25 pg/ml | <10 pg/ml |
| TNFα | ≥20 pg/ml | 5 pg/ml to <20 pg/ml | <5 pg/ml |

The mouse cytokine threshold concentration values of Table 1 were determined from the experimental data, in conjunction with available literature reports, and have a variability of ±10%.

The mouse cytokine threshold concentration values for a severe/high response correspond to a human CRS grade of 4-5; the mouse cytokine threshold concentration values for a medium/mild response correspond to a human CRS grade of 1-3; and the mouse cytokine threshold concentration values for a medium/mild response correspond to a human CRS grade of <1.

In the disclosed methods with 1.5-3.0×10$^7$ engraftment of PBMCs in the mice, the inventors have determined that when a severe/high response is observed in the mice, for example when IFN-γ≥1,800 pg/ml or IL-10≥120 pg/ml, then it is likely that the human may have a severe cytokine release syndrome following administration of the drug or drug candidate. Similarly, in the disclosed methods with 1.5-3.0× 10$^7$ engraftment of PBMCs in the mice, the inventors have determined that when a low/no response is observed in the mice, for example when IFN-γ≤300 pg/ml or IL-10<25 pg/ml, then it is likely that the human will not have a severe cytokine release syndrome following administration of the drug or drug candidate, but instead will likely have at most a low level of cytokine release. A concentration of IFN-γ or IL-10 in the mice engrafted with 1.5-3.0×10' PBMCs between these threshold values is designated a medium/mild response, indicating that the human is likely to experience a medium/mild cytokine release syndrome following administration of the drug or drug candidate. The threshold values in mice of induced IL-6, IL-4, IL-2, or TNFα can be used similarly to assess severity of the cytokine response to a drug or drug candidate The threshold values in mice of induced IFN-γ, IL-10, IL-6, IL-4, IL-2, and TNFα can be used alone or in any combination to assess severity of the cytokine response to a drug or drug candidate in a human.

The terms "donors", "individuals", "humans", "subjects" and "patients" (and the singular forms of these terms), are used herein somewhat interchangeably. In the tests conducted by the present inventors, "donor" PBMC was used. In the present method, rather than a "donor", PBMCs from a particular human, individual, subject, or patient, for whom the immunomodulatory drug is being considered for possible administration would be used. The use of one of these terms herein is intended to encompass each of these terms. In the present method, the individuals, subjects, and patients are human. However, it is contemplated that the method may be applied to other mammals, perhaps with some modifications to the method, which may be determined by those skilled in the art, using the methods and techniques described herein.

The term "immunomodulatory drug" means any therapeutic agent (e.g., mAb) that can activate or suppress the immune system, e.g., by activating or inhibiting lymphocyte functions, for example, T-cell functions like T-cell inhibition or activation Immunomodulatory drugs or agents, or immunomodulators, or immunotherapeutic drugs may include for example interleukins, cytokines, chemokines, immunomodulatory imide drugs or other agents that may be used in immunotherapy. By way of non-limiting example, cancer immunotherapy attempts to stimulate the immune system to destroy tumors. Thus, immunomodulatory drugs or agents may be used to try to treat cancer in a patient, but immunomodulatory drug uses are not limited to treatment of cancer Immunotherapy may be used on its own, or in combination with other treatment methods. An example embodiment of the immunomodulatory drug is an immunostimulating drug, like an antibody, preferably a monoclonal antibody (mAb). For example, the monoclonal antibody can be a human CD28 specific superagonistic monoclonal antibody.

Examples of immunomodulatory drugs include granulocyte colony-stimulating factor (G-CSF); interferons; imiquimod; thalidomide and its derivatives or analogues, lenalidomide (REVLIMID®), pomalidomide (IMNOVID®), and apremilast; azathioprine, cladribine, cyclophosphamide, intravenous immunoglobulin, methotrexate, mitoxantrone; IMLYGIC™ (talimogene laherparepvec), a genetically modified oncolytic viral therapy; daratumumab (DARZALEX®), an anti-CD38 antibody; adalimumab (HUMIRA®), EMPLICITI™ (elotuzumab), epacadostat, an orally available hydroxyamidine inhibitor of indoleamine 2,3-dioxygenase (IDO1), catumaxomab (REMOVAB®), ibritumomab tiuxetan (ZEVALIN®), tositumomab-I$^{131}$ (BEXXAR®), brentuximab vedotin (ADCETRIS®), betuximab (ERBITUX®), rituximab (MAB THERA® or RITUXAN®), alemtuzumab (CAMPATH-1H®), bevacizumab (AVASTIN®), pertuzumab (PERJETA®), trastuzumab (HERCEPTIN®), trastuzumab emtansinen (KADCYLA™), denosumab (PROLIA® or XGEVA®), ipilimumab (YERVOY®), ofatumumab (ARZERRA®), and panitumumab (VECTIBIX®).

A checkpoint inhibitor is a drug that blocks certain proteins made by some types of immune system cells, such as T cells, and some cancer cells. These proteins help keep immune responses in check and can keep T cells from killing cancer cells. When these proteins are blocked by the checkpoint inhibitor, the "brakes" on the immune system are released. While this release of the immune "brakes" can permit T cells to be better able to kill cancer cells, it can also lead to CRS as an adverse effect.

An exemplary class of immunomodulatory drugs is checkpoint inhibitors, which are often monoclonal antibodies such as the FDA approved cancer drugs ipilimumab (YERVOY®), pembrolizumab (KEYTRUDA®), and nivolumab (OPDIVO®). An important aspect of the immune system is its ability to differentiate between normal cells in the body and those it sees as "foreign." This lets the immune system attack the foreign cells while leaving the normal cells alone. To do this, it uses "checkpoints", molecules on certain immune cells that need to be activated (or inactivated) to start an immune response. Exemplary FDA-approved checkpoint inhibitors include the CTLA-4 inhibitor ipilimumab (YERVOY®), the PD-1 inhibitors pembrolizumab (KEYTRUDA®) and nivolumab (OPDIVO®), and the PD-L1 inhibitors atezolizumab (TECENTRIQ®), avelumab (BAVENCIO®), and durvalumab (IMFINZI®).

The term "T-cell activation" preferably specifies the mechanisms of activation of T-cells which may vary slightly between different types of T cells. The "two-signal model" in CD4+ T cells, however, is applicable for most types of T-cells. In more detail, activation of CD4+ T cells typically occurs through the engagement of both the T cell receptor and CD28 on the T cell surface by the major histocompatibility encoded antigen-presenting molecule and with its bound antigenic peptide and B7 family members on the surface of an antigen presenting cell (APC), respectively. Both cell-cell contacts are generally required for the production of an effective immune response. For example, in the absence of CD28 co-stimulation, T-cell receptor signaling alone may result in T-cell anergy. The further signaling pathways downstream from both CD28 and the T cell receptor involve many further proteins known to the skilled person. The activation of T-cells may be determined by cytokine release and/or cell proliferation, in particular, proliferation of T-cells, as described herein below.

The term "Clinical Score" is adopted that as defined by Jamie L Brady, et al. "Preclinical Screening for Acute Toxicity of Therapeutic Monoclonal Antibodies in a hu-SCID Model", Clinical & Translational Immunology (2014) 3, e29; doi:10.1038/cti.2014.28; published online 19 Dec. 2014: 0=normal activity; 1=normal activity, piloerection, tiptoe gait; 2=hunched, reduced activity but still mobile; 3=hypomotile but mobile when prompted; 4=moribund (non-responsive to touch).

The term "dose" or "dosage" means the amount of a drug to be taken at one time by a patient.

A "safe dosage" of an immunomodulatory drug for a human refers herein to a dosage producing a cytokine blood concentration in mouse corresponding to a low/no response, e.g., IFN-γ is <300 pg/ml and IL-10 is <25 pg/ml, following administration of the immunomodulatory drug to an irradiated, immunodeficient mouse engrafted with $1.5$-$3.0 \times 10^7$ peripheral blood mononuclear cells (PBMCs) isolated from the human, as determined by the methods disclosed herein. An immunologically safe dosage may or may not correspond to a dosage having therapeutic efficacy.

"Efficacy" means the ability of a drug or an active agent administered to a patient to produce a therapeutic effect in the patient.

A "therapeutically effective amount" or "effective amount" is that amount of a pharmaceutical agent to achieve a pharmacological effect. The term "therapeutically effective amount" includes, for example, a prophylactically effective amount. An "effective amount" of a drug is an amount needed to achieve a desired pharmacologic effect or therapeutic improvement without undue adverse side effects. The effective amount of a drug will be selected by those skilled in the art depending on the particular patient and the disease. It is understood that "an effective amount" or "a therapeutically effective amount" can vary from subject to subject, due to variation in metabolism of the drug, age, weight, general condition of the subject, the condition being treated, the severity of the condition being treated, and the judgment of the prescribing physician.

The term "immunotoxicity" herein refers to the propensity of a drug or a drug candidate to generate adverse immunostimulation, such as cytokine release syndrome.

The term "drug candidate" means any potential drug or composition, including one or more active agents such as antibodies, small molecules and/or other compounds that are identified by drug discovery screening to potentially have a therapeutic effect of alleviating, treating, and/or curing a disease, illness, injury, ailment or condition.

In one aspect, the present inventors invented a humanized mouse model for screening and determining drug immune toxicity, in particular, cytokine release syndrome (CRS) in an individual, for pre-clinical testing, clinical trials, and/or individual treatment of the individual with the drug. The present invention is useful to determine the reactivity of individuals to immunomodulatory drugs and to determine a safe dosage of administration of an immunomodulatory drug to the individuals.

In another aspect, the present humanized mouse method is also useful in pharmaceutical safety evaluations of a drug candidate. In particular, the disclosed method provides an improved pre-clinical animal test of the immunotoxicity of a drug candidate in humans.

The methods for determining drug immunotoxicity disclosed herein have the advantages of an ability to detect individual variation in response to a given immunomodulatory drug or combination of immunomodulatory drugs, greater accuracy in response prediction than prior art methods such as in vitro PBMC cell culture methods, a requirement for only moderate amounts (100 ml or less) of blood drawn from an individual for testing, commercial availability of suitable immunodeficient mice, and a turnover time of less than two weeks.

With respect to pre-clinical immunotoxicity testing of drug candidates, the method has all the above advantages, and further provides a sensitive method for assessing the level of immunostimulation that a drug candidate will induce after administration, permitting savings of time and costs in drug development by permitting early elimination of drug candidates inducing unacceptably high levels of immunostimulation (e.g., cytokine release induced by administration of such drug candidates in humans).

Advantageously, as discussed further herein, the present inventors have found that this assay system is predictive of the in vivo responses and represents a powerful tool in research and pharmaceutical safety evaluations. Current clinical testing of new drug candidates on volunteer human subjects often results in drugs failing. The failure is because the toxicities were not exposed in pre-clinical studies largely due to the inadequacy of the existing in vivo animal models. There is a long-felt unmet need for an in vivo animal model that can accurately predict the adverse effects of a potential drug candidate. The present humanized mouse model is useful as a drug screening platform with a high degree of accuracy to identify from a large number of clinically relevant drug candidates the potential drug candidates that elicit cytokine release. The present methods thus represent robust prediction assays for drug immunotoxicity testing, providing a necessary link between pre-clinical and clinical testing. The integration of the present assay into drug development programs should accelerate the drug approval process, such as before the FDA, for therapeutic drug development.

In one aspect, the present invention is directed to a method of determining whether an immunomodulatory drug causes immune toxicity in a human In other words, the present method can serve as a screening assay for individual patients to be received an immunomodulatory drug if that patient is safe to receive such an immunomodulatory drug. The method can comprise: harvesting peripheral blood mononuclear cells (PBMCs) from a human subject; administering the immunomodulatory drug (e.g., mAb) to a immunodeficient non-human mammal that has been irradiated and engrafted with the harvested PBMCs from that individual (e.g., humanized immunodeficient mouse); and detecting one or more cytokines (exemplified by IFN-γ and/or IL-10) released; and thus determining whether the immunomodulatory drug causes an immune toxicity, wherein if the immunomodulatory drug elicits a severe cytokine storm in the non-human mammal then the immunomodulatory drug causes immune toxicity in that individual.

There is a long-felt unmet need for a reliable in vivo mouse method useful for physicians to determine potential CRS in human subjects prior to administration of an immunomodulatory drug. Ideally, the method should accurately determine which of the human subjects receiving the immunomodulatory drug would suffer severe CRS adverse events. As reported in March 2006, discussed above, during the human trail at Northwick Park Hospital involving mAb TGN1412, six volunteers in the trial were hospitalized because of the adverse events. Many of the patients suffered angioedema, swelling of skin and mucous membranes followed by multiple organ dysfunction although pre-clinical work for that trial showed no suggestion of CRS in a rat model or in cynomolgus monkeys (*Macaca fascicularis*), or in in vivo human PBMC cell culture assays. However, it was discovered by the present inventors, that certain patients may or may not have severe CRS adverse events to a given immunomodulatory drug, and they have invented a method for determining in advance whether a particular patient may suffer from CRS if administered a particular drug.

Cytokine release syndrome occurs with activation of T cells and Natural Killer (NK) cells as well as other immune cell populations (e.g., macrophages, etc.). With the addition of immunomodulators, the activation of the T cells and natural killer cells can lead to the release of high levels of cytokines and downstream injury and possible death. While the role of T cell activation has received much attention due to the TGN1412 clinical trial, NK cell activation has also been shown to be a source of cytokine release syndrome in response to certain immunomodulators, For example, treatment with CAMPATH 1-H, an anti CD52 antibody, was shown to involve NK cells, with the release of high levels of TNF, IFN-γ and IL-6 in vivo (Wing M. G. et al. (1995) Ther. Immunol. 2:183-190) and the toxicity resulting from treatment with the combination of IL-2 and IL12 was shown to be the result of activation of natural killer cells, but not B or T cells (Carson W. E., (1999) *J Immunol* 162; 4943-4951). With different immunomodulators and the activation of various immune cell populations, cytokine release syndrome can manifest with high levels of cytokine release that can vary with the various activated immune cell populations.

The present inventors realized that in this complex biological system, many variables would have to be carefully chosen and optimized before a mouse model can provide an accurate prediction of drug-induced CRS. Unfortunately, at the present time there is little guidance in the art as to which variables should be selected or how they should be optimized. Given the highly intricate and complex nature of the system, a delicate balance among these variables is required in order for a mouse model to provide a useful and accurate prediction of drug-induced CRS.

The present inventors discovered that human cell number (i.e., the number of PBMCs administered to the mouse) and the distribution of human cell types present in the mouse (which changes with time after engraftment) are critical variables in the system. It is discovered that when human PBMCs are injected into a mouse, only human T cells can expand; the other human cell types, e.g., NK cells and B cells, will begin to die out. It is further discovered that when the human T cell count becomes too high in the mouse, they will cause GVHD which is manifested by body weight loss, hunched posture, fur loss, reduced mobility, tachypnea, and eventual death. When a mouse exhibits severe GVHD, accuracy of the testing results is severely impaired.

Without being bound by a theory, it is unexpectedly discovered that the adult human T cells in the PBMCs recognize the mouse as foreign and start to attack the mouse, causing health issues for the mouse and possibly death, with concomitant release of cytokines. When this happens, the mouse starts to suffer significant weight loss and exhibits sick symptoms that render the mouse model inaccurate in determining CRS.

Without being bound by a theory, it is believed that engraftment of too many PBMCs increases the cytokine release profile in the mouse such that the method provides an inaccurate prediction (i.e., is prone to providing a false positive). It is observed that when the number of PBMCs engrafted exceeds $5 \times 10^7$ PBMC/mouse, some mice suffer significant weight loss, probably due to GVHD (graft versus host disease) very quickly after engraftment. When the mice have GVHD, the cytokine release response in these mice induced by an immunomodulatory drug cannot accurately determine the response of the human subject to the immunomodulatory drug. Alternatively, when the number of PBMCs engrafted is below a certain threshold (e.g., $<1 \times 10^7/$ mouse), the method also cannot determine the response of the human subject to an immunomodulatory drug with optimal sensitivity, and will provide a false negative. Moreover, we irradiate the mice by X-ray to destroy the mouse immune system prior to engraftment to minimize rejection and maximize survival of the injected human PBMCs.

Thus, the present inventors have determined that the number of PBMCs engrafted and the PBMC engraftment time prior to immunomodulatory drug administration are critical for optimal accuracy of the assay by balancing presence of an adequate population and distribution of human immune cells in the mouse against onset of GVHD in the mouse.

The PBMC humanized mouse model, unlike earlier BLT (bone marrow/liver/thymus) or stem cell humanized mouse models, has been considered in the art to be a T cells only model, since when human PBMCs are injected into a mouse body, only the T cell population can expand, while the other human cell types die out with time. In the art, PBMC humanized mice have usually been used after 10 days of PBMC engraftment, with a PBMC engraftment number of usually from 1 to 10 million cells per mouse, requiring the research to wait for the T cell population to expand to a large enough number to do the experiment. Usually 10% human CD45 or human CD3 T cells present in the mouse cell population has been used as the standard for the minimum number of human cells. However, the present inventors have determined that in order for the PBMC humanized mouse model to provide optimal drug toxicity testing, not only T cells are needed in the mouse, but also other cell types, especially NK cells and monocytes.

Accordingly, in certain embodiments herein, the present invention fulfills a long-felt unmet need and is directed to an in vivo method of determining if an immunomodulatory drug elicits a cytokine storm response (i.e., severe cytokine release syndrome) in an individual, such as a human, comprising the steps of: (a) harvesting or isolating PBMCs from an individual human who is being considered to receive an immunomodulatory drug; (b) engrafting $1.5\times10^7$-$3.0\times10^7$ harvested/isolated PBMCs into an immunodeficient mouse (NSG, NSG-IL-6, or NSG-CSF-1) that has received irradiation (e.g., to functionally suppress mouse immune cells to attack engrafted PBMCs); (c) administering the engrafted immunodeficient mouse with the immunomodulatory drug day 5-7, preferably day 6, after the engraftment; (d) detecting the presence of one or more cytokines released after the administration; and (e) evaluating the cytokine response to the immunomodulatory drug in comparison to a control agent (e.g., control mAb) to determine whether the cytokine release in the mouse by determining blood concentration in the mouse of a plurality of cytokines comprising IFN-γ and IL-10 is of a level that indicates severe cytokine release syndrome.

In one embodiment, the present method comprises engrafting $1.5\times10^7$-$3.0\times10^7$ PBMCs isolated from a human into an irradiated immunodeficient mouse (e.g., an NSG, NSG-IL-6, or NSG-CSF-1); administering an immunomodulatory drug to the engrafted immunodeficient mouse 5-7 days, preferably 6 days, after the engraftment; detecting the amount of one or more cytokines released after the administration; and determining the immunomodulatory drug likely elicits a severe cytokine release syndrome in the human wherein presence of a severe cytokine release syndrome in said mouse is indicative that administration of said immunomodulatory drug likely elicits a severe cytokine release syndrome in said human. The present method can further comprise providing the irradiated immunodeficient mouse, said mouse is irradiated with 75-125 cGy X-ray, or isolating the PBMCs from the human, or comparing the cytokine amounts released after drug administration to amount released after administration of a negative control agent. Examples of a suitable negative control agent include a buffer or an isotype control mAb. The cytokine detected can be IFN-γ, IL-10, IL-6, IL-2, IL-4, TNF, or a combination of the foregoing, preferably the cytokine is IFN-γ or IL-10. The present assay enables a physician to differentiate (or identify) which human patient(s) would likely suffer from a severe CRS as compared to others who would not suffer from a severe CRS.

According to preferred example embodiments, prior to engrafting, the immune deficient mouse is irradiated with 75-125 cGy X-ray, or 100 cGy X-ray. According to further example embodiments, the irradiation takes place at least four hours prior to engrafting.

The present inventors have established that PBMCs can be harvested from an individual (supposed to receive an immunomodulatory drug) and can be used to engraft in an immunodeficient mouse (e.g., NSG, NSG-IL-6, or NSG-CSF-1) to obtain a humanized mouse to test immune toxicity (i.e., cytokine release) induced by one or more drugs using the assay disclosed herein. Advantageously, the present inventor has surprisingly found that this assay system is predictive of the in vivo responses in a human patient who would receive the administration of an immunomodulatory drug.

There are a variety of human cytokines that can be used in the methods of the invention. Many inflammatory cytokines are known to be released during cytokine release syndrome, including IFN-γ, IL-β, TNF, IL-2, IL-6, IL-8, IL-10, and IL-12. Some cytokines are believed to have more significant importance than others in determining cytokine release syndrome. In the present invention, it may be especially appropriate to include IFN-γ and/or IL-10 as predictive cytokines for determining a CRS response (Teachey D T, et al. Cancer Discov. 2016 June; 6(6):664-79. doi: 10.1158/2159-8290. CD-16-0040. Epub 2016 Apr. 13).

The present inventors discovered that IFN-γ and/or IL-10 in the humanized mouse blood can be used to reliably predict the severity of the CRS that can be expected in a subject. The IFN-γ levels and IL-10 levels in PBMC-humanized mice are high compared to other cytokine levels after induction by an immunomodulatory drug and compared to humans. It is contemplated that other antibodies may be used to help determine the severity of potential response.

The present inventors have discovered that donors whose IFN-γ level in the blood of the humanized mouse was at or above 1,800 pg/ml and/or the IL-10 level was at or above 120 pg/ml, 6 hours after administration of an immunomodulatory drug to the mouse, such as anti-CD28 (ANC28.1/5D10), were likely to develop severe CRS (e.g. grade 4-5) if the drug were to be administered to that human subject. Donors whose IFN-γ level was between 300 pg/ml and 1,800 pg/ml, and/or whose IL-10 level was between 25 pg/ml and 120 pg/ml in the blood of the humanized mouse were likely to develop a modest CRS (develop grade 1-3 CRS) (but not a severe CRS) after receiving the immunomodulatory drug. Donors whose IFN-γ level was below 300 pg/ml and/or IL-10 level was below 25 pg/ml in the blood of the humanized mouse were likely not to develop CRS after receiving the immunomodulatory drug (Teachey D T, et al. 2016; Weiβmuller et al., PloS One DOI:10.1371/journal.pone.0149093 March 2016).

In certain embodiments, the present invention is directed to using 15 million to 30 million harvested/isolated human PBMCs per mouse from a donor/subject and engrafting the PBMCs in the immune deficient mouse to obtain a humanized immunodeficient mouse, as discussed below. In certain preferred embodiments, 15 million to 25 million harvested/isolated human PBMCs per mouse are used. In certain preferred embodiments, 20 million harvested/isolated human PMBCs per mouse are used. 5-7 days after the engraftment, an immunomodulatory drug is administered to the mouse, and the human cytokine concentrations in the mouse are measured to determine if the cytokine release of IFN-γ and IL-10 is that of a "severe or high response", "medium or low response" or "no response", as a predictor or determiner of whether the particular donor/subject will exhibit cytokine release syndrome (CRS) after administration of the immunomodulatory drug. "Severe/high response" is measured as an IFN-γ level equal to or above 1,800 pg/ml and an IL-10 level equal to or above 120 pg/ml at 6 hours after administering the immunomodulatory drug to the humanized mouse. IFN-γ and IL-10 are measured because they have been identified as being most predictive of whether cytokine release syndrome or cytokine storm will occur. The inventors demonstrated that, using the present in vivo assay system, different human donor PBMCs engrafted into immunodeficient mice respond differently to CRS inducing agents.

In the present methods, if the subject is a "low/no responder" in the humanized mouse model method, he/she will not likely elicit a cytokine response upon immunomodulatory drug administration, in which case it is safe to administer the immunomodulatory drug to the individual. Therefore, immunomodulatory drugs that were previously unavailable for use in treatment, because of the potential to have extremely adverse cytokine storm effects, may in fact be used on a particular individual, if that individual is determined to be a "low/no responder" using the present methods. If that individual is determined through the present methods to have severe/high IFN-γ and IL-10 response to an immunomodulatory drug using the mice humanized with the individual's PBMCs, that individual is likely to elicit a cytokine storm response, and then it is not safe to administer the immunomodulatory drug to the individual.

In the present methods, immune deficient mice (also known as immunodeficient mice) are used. NSG mice are a strain of inbred laboratory mice that are immunodeficient. NSG mice lack mature T-cells, B-cells, and natural killer (NK) cells or a combination thereof. NSG mice are also deficient in multiple cytokine signaling pathways, and they have many defects in innate immunity. The compound immunodeficiencies in NSG mice permit the engraftment of a wide range of primary human cells to obtain humanized mice, and enable sophisticated modeling of many areas of human biology and disease. The present inventors discovered that NSG mice have similar responses as that of NSG-CSF-1 mice and NSG-IL-6 mice. As used herein, the terms "humanized mouse", "humanized immune deficient mouse", "humanized immunodeficient mouse", and the plural versions thereof are used interchangeably. Thus, the use of one of these terms, should be construed as encompassing all.

In certain embodiments, the non-human mammal is a genetically modified mouse lacking an immune system (i.e., a humanized immunodeficient mouse). Examples of an immunodeficient mouse include but are not limited to NSG (i.e., NOD scid gamma (NOD.Cg-Prkdc$^{scid}$I12rg$^{tm1wjl}$/SzJ) mice), NSG-CSF-1, NSG-IL-6, and the like. The present invention is intended to encompass other specific examples of immunodeficient mice. The immunodeficient mouse preferably lacks its own T-cells, B-cells, NK cells or a combination thereof. As a result, the immunodeficient mouse is expected to allow engraftment of human peripheral blood mononuclear cells (PBMCs) without immediate graft-v-host rejection.

Although a prior in vivo assay can be used to demonstrate a drug-induced cytokine signal, it is hypothesized by the present inventors that because prior assays fail to consider criticality of numbers of donor cells as well as its dynamic immunological changes (e.g., sufficient circulating CD3 cells and NK cells as well as presence of GVHD) in the tested animals, prior art assays are susceptible to producing false positive and false negative responses. The former may be due to too many donor cells (i.e., CD3 cells and NK cells), thus rendering the assay too sensitive—and failing to yield an accurate prediction of cytokine release. The latter may be due to too little donor cells (i.e., CD3 cells and NK cells), also rendering the assay too insensitive—failing to yield an accurate prediction of cytokine release. To complicate the matter, too high CD3 cells can cause the graft v. host defense mechanism operating in the tested animals, making the mouse model unsuitable for screening cytokine release.

The present invention cures the long-felt unmet need of providing an in vivo screening assay that accurately determines severe CRS in human subjects. This is achieved by adjusting the amounts of PBMCs engrafted and the timing of administering a drug after PBMC engraftment.

As appreciated by those of skill in the art, there are many suitable ways to harvest and isolate PBMCs. There are also many suitable ways to introduce PBMCs into an immunodeficient mouse, including by way of non-limiting example, intravenously and intracardially.

The present inventors have established that PBMCs can be harvested from an individual human (supposed to receive an immunomodulatory drug) and then can be used to engraft in an immunodeficient mouse (e.g., NSG, NSG-IL-6, or NSG-CSF-1) to test toxicity (i.e., cytokine release) using the assay disclosed herein. Advantageously the present inventors have found that this assay system is predictive of the in vivo responses in the human patient providing the PBMCs who would receive the administration of an immunomodulatory drug.

Without being committed to a theory, it is believed that too many PBMCs may enhance the sensitivity of the cytokine release profile such that it overreaches to provide an inaccurate prediction (i.e., provides many false positives). It is observed that when the number of PBMCs exceeds $5 \times 10^7$ PBMC/mouse, some mice suffer significant weight loss, probably due to GVHD (graft versus host disease). When this happens, the cytokine release response in these mice induced by the immunomodulatory drug cannot accurately determine CRS in a human subject. Alternatively, when the number of PBMCs administered is below a certain threshold (e.g., $<1 \times 10^7$/mouse), the method also cannot determine a CRS with an optimal sensitivity (i.e., provides many false negatives).

In example embodiments of the present methods, at least four hours before engrafting isolated PBMCs to the immune deficient mouse, the mouse is irradiated with 100 cGy X-ray (or 75 cGy-125 cGy X-ray). The irradiation may occur after, before or simultaneous with the step of harvesting and isolating the PBMCs from the human. It is believed that by using irradiation, the T cells will expand faster in NSG mice. Without being bound by theory, it is believed that irradiation enhances the engraftment of human cells. Although the exact mechanism is still not clear, irradiation can lead to myeloablation, which destroys the mouse immune cells and increases human PBMC survival factors and speeds up human T cell expansion. The irradiation also induces cell death (apoptosis) of mouse immune cells in the peripheral blood, spleen, and bone marrow allowing increased human immune cells to go to the bone marrow. Without irradiation, it would take longer to get enough human immune cells to perform the present methods. However, with time, the human PBMCs will lose some cells types, for example, NK cells and monocytes, because these cell types cannot grow in mice and they just survive for some days and die out. NK and myeloid cells turn over more rapidly than CD3 T cells in general, however the short survival of NK cells and myeloid cells in the mice is due to the lack of factors, such as IL15, that stimulate their survival. With or without irradiation, the NK cells should be lost by day 10 after PBMC engraftment due to the short survival of NK cells (and myeloid cells). Only T cells can expand in NSG mice. The assay needs as many human immune cell types for testing toxicity as possible. Therefore, the time period with the optimal population of engrafted human immune cells and before onset of severe GVHD, e.g., day 5-7 for the present method with engraftment at $1.5\times10^7$ to $3.0\times10^7$ PBMCs, is critically important to achieving optimal sensitivity while minimizing false negatives.

In certain example embodiments, the present invention relates to engrafting a specific range of human PMBCs (1.5 to $3.0\times10^7$/mouse) to an immunodeficient mouse. In certain preferred embodiments, the number of engrafted human PBMCs is $2\times10^7$/mouse.

The present inventors also discovered that when a particular individual's PBMC is engrafted in an irradiated immunosuppressed mouse, and then an immunomodulatory drug is administered to the mouse during a critical time period after such engrafting (e.g. 5-7 days later) (preferably, 6 days later), then cytokine response can be measured using IFN-γ and/or IL-10 to determine if that particular human is a "severe" or "high responder", meaning that the subject will likely elicit a massive cytokine release response such as cytokine release syndrome, which may be potentially lethal to the human, and therefore should not be administered the immunomodulatory drug.

Certain T-cell activating agents, in particular monoclonal antibodies (mAb) addressing the T-cell antigen receptor (TCR) such as ORTHOCLONE OKT®3 ("OKT3"), a murine monoclonal antibody (mAb) which was the first mAb used in the clinic for immunosuppression, may induce the systemic release of pro-inflammatory cytokines (Abramowicz D. et al., Transplantation, 1989 April; 47(4): 606-8). The most dangerous of these are TNF, interferon-gamma (IFN-gamma) and IL-2. In patients receiving mAb therapies, control of such a cytokine release syndrome or "cytokine storm" is routinely achieved by high dose corticosteroid treatment. ORTHOCLONE OKT®3 is a brand name for muromonab-CD3, an immunosuppressant drug given intravenously to reverse acute rejection of transplanted organs, including the heart, kidneys, and liver. OKT3 acts by blocking the function of T cells which play a major role in acute graft rejection. OKT3 reacts with and blocks the function of a molecule called CD3 in the membrane of T cell. The binding of OKT3 to T lymphocyte results in their early activation, leads to cytokine release, followed by blocking T cell functions. It is an immunosuppressant drug that is a strong inducer of CRS. The anti-CD28 antibody ANC28.1/5D10, is a weaker CRS inducer. Other antibodies and immunomodulatory agents may be used in the present methods, including drug candidates under development.

Examples of immunomodulatory drugs include, but are not limited to, an anti-CD28 monoclonal antibody (mAb), an anti-CD3 mAb, an anti-CD20 mAb, an anti-CD52 mAb; granulocyte colony-stimulating factor (G-CSF); an interferon; imiquimod; thalidomide and its derivatives or analogues, such as lenalidomide (REVLIMID®), pomalidomide (IMNOVID®), and apremilast; azathioprine, cladribine, cyclophosphamide, intravenous immunoglobulin, methotrexate, mitoxantrone; IMLYGIC™ (talimogene laherparepvec); adalimumab (HUMIRA®), catumaxomab (REMOVAB®), ibritumomab tiuxetan (ZEVALIN®), tositumomab-I$^{131}$ (BEXXAR®), brentuximab vedotin (ADCETRIS®), betuximab (ERBITUX®), rituximab (MAB THERA® or RITUXAN®), alemtuzumab (CAMPATH-1H®, CAMPATH® or LEMTRADA®), bevacizumab (AVASTIN®), pertuzumab (PERJETA®), trastuzumab (HERCEPTIN®), trastuzumab emtansinen (KADCYLA™), denosumab (PROLIA® or XGEVA®), ofatumumab (ARZERRA®), panitumumab (VECTIBIX®), pembrolizumab (KEYTRUDA®), nivolumab (OPDIVO®), ipilimumab (YERVOY®), atezolizumab (TECENTRIQ®), avelumab (BAVENCIO®), durvalumab daratumumab (DARZALEX®), ceritinib (ZYKADIA®), and anti-thymocyte globulin (THYMOGLOBULIN® (rabbit) or ATGAM® (equine)).

Accordingly, in certain example embodiments, the immunomodulatory drug is a therapeutic antibody. The antibody may be monoclonal or polyclonal. Monoclonal antibodies (mAbs) may include, but are not limited to, TGN1412 (anti-CD28 mAb) (TAB08), OKT3 (anti-CD3 mAb), RITUXAN® (rituximab) (anti-CD20 mAb), LEMTRADA® (alemtuzumab, also marketed as CAMPATH®) (anti-CDS2 mAb), KEYTRUDA® (pembrolizumab), OPDIVO® (nivolumab), YERVOY® (ipilimumab), ZYKADIA® (ceritinib), TECENTRIQ® (atezolizumab), BAVENCIO® (avelumab), IMFINZI® (durvalumab) and the like. In other embodiments, the immunomodulatory drug can be a small molecule drug, such as REVLIMID® (lenalidomide); a polyclonal antibody such as anti-thymocyte globulin; or a biologic drug such as a protein, such as an interferon.

As will be appreciated by those of skill in the art, the immunomodulatory drug can be administered to the non-human immunodeficient mammal using a variety of routes of administration. Exemplary routes of administration include, but are not limited to, intravenous, intrafemoral, intraventricular, intracardial, intraperitoneal routes of administration, and the like. Preferred route of administration is intravenous infusion.

Without committing to a particular theory, it is believed that the predominant cells present in a humanized immunodeficient mouse at day 5-7 after engrafting the mouse with human PBMCs may be tested for cytokine release syndrome or cytokine storm toxicity upon administration of an immunomodulatory drug. The testing depends on factors including the number of PBMC cells and the ratio of human PBMC after injection. The balance of cell types and cell number (quantity) of cells administered is believed to be important in determining cytokine release syndrome. For example, as shown in the FIG. 2B, NK cells (CD56) were about 20-30% of the CD45 cells present and decreased to 1-5% by day 10 after engraftment. Therefore, by day 10, the predominant cell types in this PBMC humanized mice is T cells, and the PBMC humanized mice don't have many other human cell types and is not a good model for toxicity testing.

Non-limiting example embodiments of the present invention include a method of determining whether an immunomodulatory drug is likely to elicit cytokine release syndrome (CRS), SIRS, or cytokine storm (a severe case of CRS) in an individual human upon administration of an immunomodulatory drug to the individual. According to example embodiments, the method includes the following steps:

(a) providing an immunodeficient mouse, said mouse is irradiated with 75-125 cGy X-ray;
(b) engrafting 1.5-3.0×10$^7$ peripheral blood mononuclear cells (PBMCs) isolated from a human to said mouse;
(c) administering to said mouse an immunomodulatory drug 5-7 days after engrafting;
(d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and
(e) determining said immunomodulatory drug likely elicits a severe cytokine release syndrome in said human, wherein presence of a severe cytokine release syndrome in said mouse is indicative that administration of said immunomodulatory drug likely elicits a severe cytokine release syndrome in said human.

In another non-limiting example embodiments, the present invention includes a method of determining whether an immunomodulatory drug is likely to elicit cytokine release syndrome (CRS), SIRS, or cytokine storm (a severe case of CRS) in an individual human upon administration of an immunomodulatory drug to the individual. According to example embodiments, the method includes the following steps:

(a) isolating peripheral blood mononuclear cells (PBMCs) from a human;
(b) engrafting 2×10$^7$ of said isolated PBMCs to an irradiated immunodeficient mouse;
(c) administering to said mouse an immunomodulatory drug 5-7 days after engrafting;
(d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse, and
wherein presence of a severe cytokine release syndrome in said mouse is indicative that administration of said immunomodulatory drug likely elicits a severe cytokine release syndrome in said human.

According to example embodiments, the method may further include
(e) determining whether the human is suitable for therapy with the immunomodulatory drug,
wherein the elicited severe cytokine release syndrome in the mouse is indicative of the human not being suitable for therapy with the immunomodulatory drug.

If the concentrations of the cytokines IFN-γ and IL-10 in response to the immunomodulatory drug in the mouse model are measured as "severe/high", the immunomodulatory drug is likely to elicit a severe cytokine release syndrome or a cytokine storm, and the human is not suitable for therapy. If a human is deemed not suitable for therapy with that particular immunomodulatory drug, another antibody or chemotherapy or other drugs may be tried for treatment of the individual/patient.

If the concentrations of both IFN-γ and IL-10 exhibit "low/no response" or "low response" then the individual human is suitable for therapy with the immunomodulatory drug. The determination of "no response" vs. the low end of "low response" may be difficult to discern and may depend on the sensitivity of the assay, but it may not be necessary to set a bright line at this end of the response spectrum, as both "no response" and "low response" indicates that the human is suitable for therapy.

As described herein, humanized engrafted mice were injected with different immunomodulatory drugs such as various therapeutic antibodies including e.g., anti-CD28 mAb), OKT3 (anti-CD3 mAb), and the effects of the antibodies in humanized mice were observed. Both anti-CD28 and OKT3-treated mice showed a significant increase in major inflammatory cytokines with respect to certain individuals/samples. Administration to non-humanized mice did not induce the cytokine responses. These findings show that humanized mice engrafted with PBMC can determine immune toxicity of certain drugs for a particular subject/individual.

The present method comprises administering an immunomodulatory drug to a non-human mammal that has been engrafted with human PBMCs, and determining whether the immunomodulatory drug causes toxicity in the non-human mammal, wherein if the agent causes toxicity in the non-human mammal then the agent is believed to cause immune toxicity in a human.

Immune toxicity refers to the undesirable/unintended effect of an agent on the functioning of the immune system of an individual. See, for example, Weir, A, Journal of Immunotoxicology, 5:3-10 (2008); Gribble, E J., et al., Expert Opinion Drug Metab Toxicol, 3(2) (2007).

In some instances, immune toxicity can produce a cytokine storm in a human. Cytokine storm, cytokine release syndrome, or infusion reaction is an adverse event usually seen upon first exposure to an agent (e.g., a therapeutic mAb). It is characterized by the systemic release of several inflammatory cytokines. Symptoms range from mild to severe, including fatigue, headache, urticaria, pruritus, bronchospasm, dyspnea, sensation of tongue or throat swelling, rhinitis, nausea, vomiting, flushing, fever, chills, hypotension, tachycardia, and asthenia. See, for example, Wing, M., et al. Journal of Immunotoxicology, 5:11-15 (2008) and Wang, H., et al., American Journal of Emergency Medicine, 26:711-715 (2008).

Thus, in yet another aspect, the invention is directed to a method of determining whether administration of an (one or more) agent will cause cytokine release syndrome in an individual (e.g., human) in need thereof. The method comprises administering the agent to a non-human mammal that has been engrafted with a certain number of PBMCs after a certain number of days, and determining level of one or more human cytokines within the non-human immunodeficient mammal induced by the agent; and determining whether the agent causes cytokine release syndrome in the non-human mammal, wherein if the agent causes cytokine release syndrome in the non-human mammal then the agent will cause cytokine release syndrome in the human.

The present inventors discovered that the number of days of testing an immunomodulatory drug after the engraftment of PBMCs in an NSG, NSG-IL-6, or NSG-CSF-1 mouse is essential, insofar as the number of days results in a suitable cell composition. The number of days may vary somewhat depending on how many PBMCs are initially engrafted in the mouse. That is, if more PBMCs are engrafted (within the present range), then the number of days before testing an immunomodulatory drug may be somewhat shorter (again, within the present range), than if fewer PBMCs (within the present range) are engrafted. It is believed that the mice undergo Graft-Versus-Host Disease (GVHD) as the engrafted PBMCs start to kill the mouse cells due to the immune cell allogenic recognition of the adult human T cells to the mouse. When this happens, the mouse starts to suffer significant weight loss and exhibits severe sick symptoms that render the mouse model is inaccurate in determining CRS. In certain embodiments, the present invention provides the administration of an immunomodulatory drug 4-7 days or 5-7 days after PBMC engraftment. In certain preferred embodiments, the present invention provides the administration of an immunomodulatory drug 6 days after PBMC engraftment.

Figure 9A:
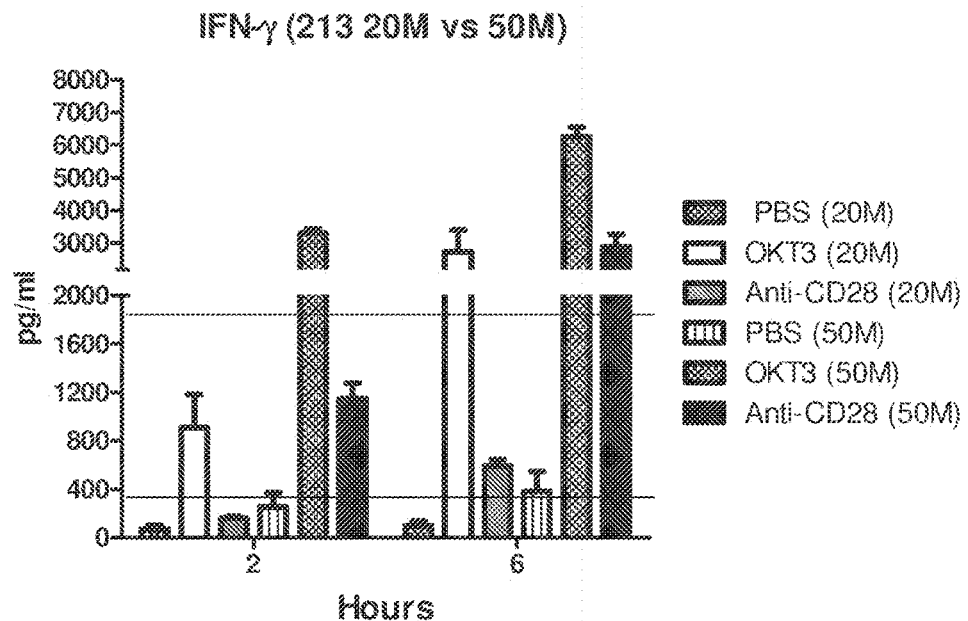
FIGS. 9A-9F depict a comparison of cytokine response in donor 213 humanized mice with 2×10$^7$ PBMCs/mouse or 5×10$^7$PBMCs/mouse.
Figure 9B:
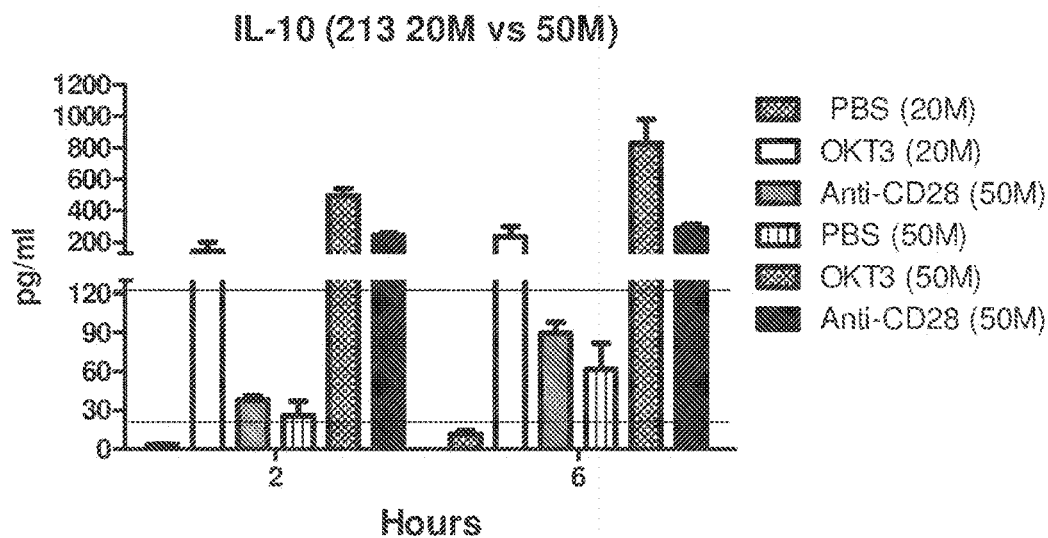
Figure 9C:
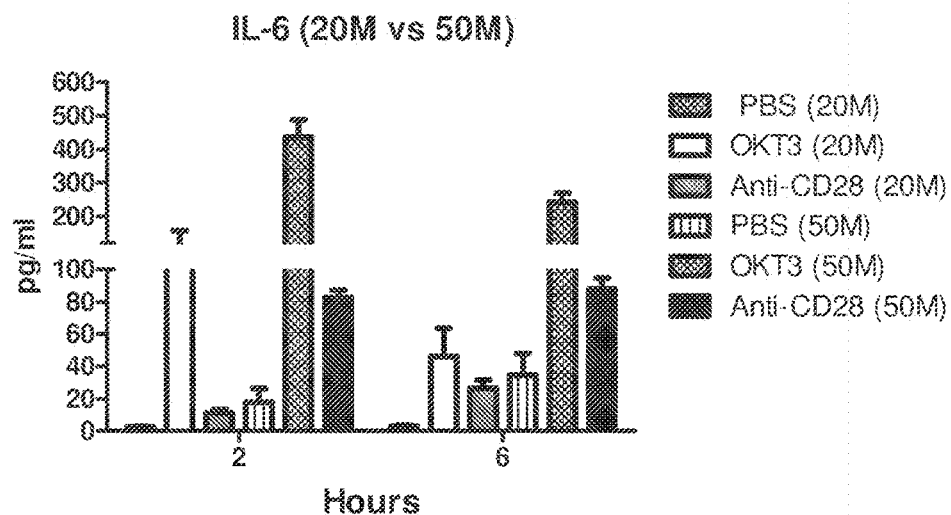
Figure 9D:
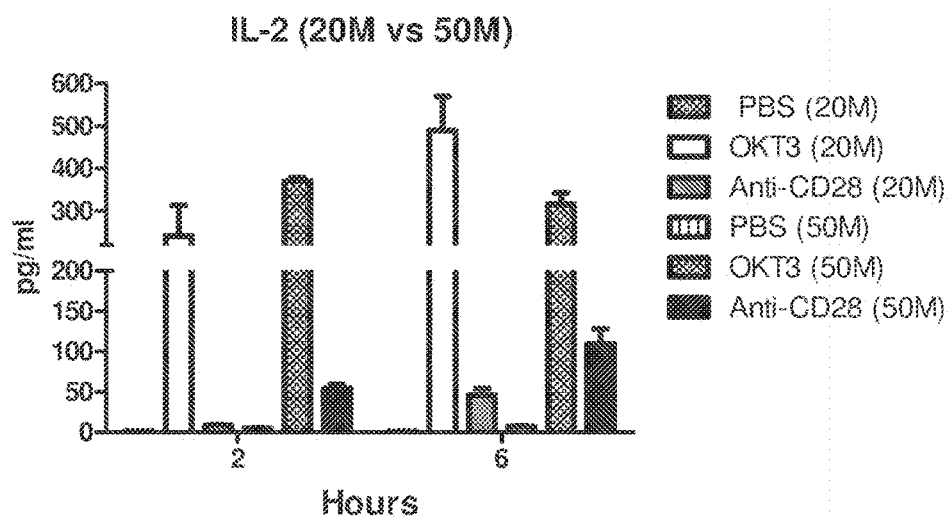
Figure 9E:
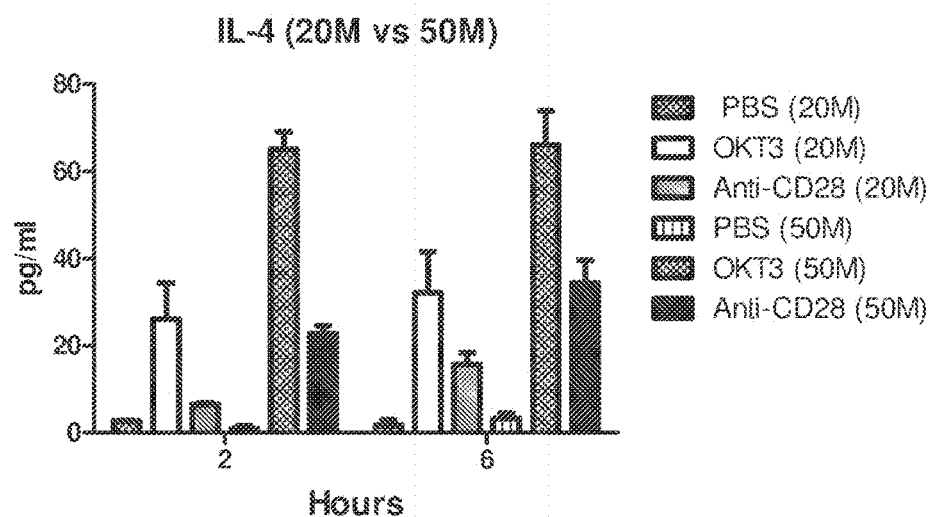
Figure 9F:
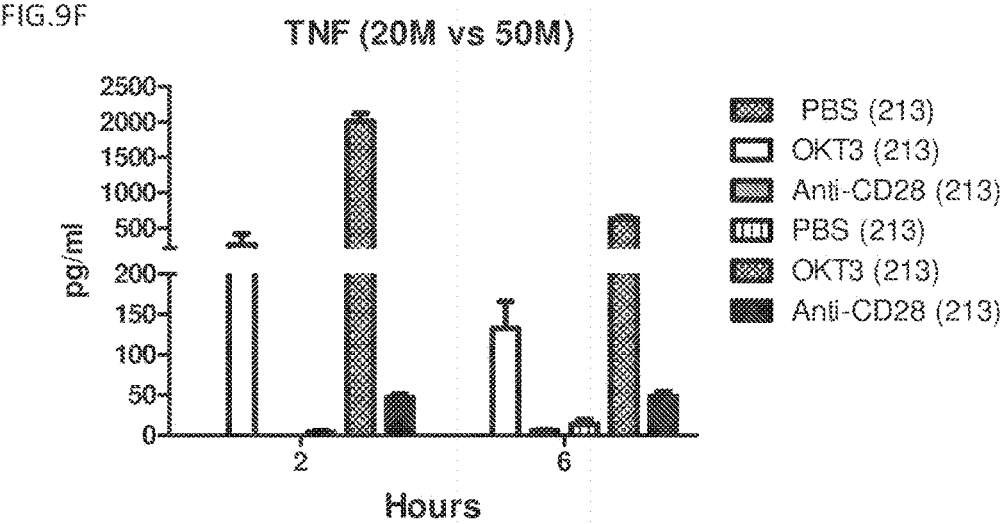

The present inventors compared the response levels of IFN-γ and IL-10 as a function of the number of cells injected in each mouse (20 million cells per mouse vs. 50 million cells per mouse) (see FIGS. 9A-9B). The number of PBMC injected into the mice is a determinative factor. When injected with a high number of PBMCs (e.g., 50 million PBMCs per mouse), the mouse showed high cytokines released, the IFN-γ and IL-10 all increased ≥1,800 pg/ml and ≥120 pg/ml, respectively. But this donor (213) (used in FIG. 9) had low cytokines released when injected with 20 million PBMCs per mouse before. This data shows that 20 million PBMCs per mouse (or a range of 15-30 million PBMCs per mouse) is within a preferred range for patient screening. In accordance with the present invention, the range of PBMCs used in detecting a cytokine storm for an individual in response to an immunotherapeutic drug is between 15 million to 30 million PBMCs. Preferably, the PBMC range is between 20 million to 25 million PBMCs. More preferably, the concentration is 20 million PBMCs per mouse.

The present invention provides an improved in vivo method for determining the potential of an immunomodulatory drug to cause an adverse cytokine release syndrome (CRS) in human patients.

Advantageously, as discussed further herein, the present inventors also found that this assay system is determinative of the in vivo responses and represents a powerful tool in research and pharmaceutical safety evaluations. Current clinical testing of new drug candidates on volunteer human subjects often results in drugs failing. The failure is because of the toxicities that were not exposed in preclinical studies largely due to the inadequacy of the existing in vivo animal models. There is a long-felt unmet need for an in vivo animal model that can accurately predict the adverse effects of a potential drug candidate. Screening of drug candidates for developing into a therapeutic drug candidate must pass both the in vitro and in vivo pre-clinical tests.

As will also be appreciated by those of skill in the art, there are a variety of ways to introduce PBMCs into a non-human mammal. Non-limiting examples of such methods may include intravenous, intrafemoral, intraventricular, intracardial routes of administration. Preferably, PBMCs are introduced via intravenously.

The present inventors have discovered that the PBMC engraftment time is critical. In particular, it is observed that the immunomodulatory drug can be administered within a specific time frame after engraftment of the mouse with PBMCs of the subject.

Figure 2C:
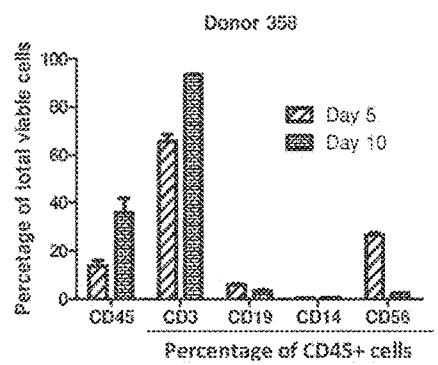
FIG. 2C depicts different cell populations on day 5 or day 10 after engraftment in NSG mice of 3×10$^7$ hPBMCs/mouse from donor 358. 4 mice per group per each time point and data are presented as mean±SEM.
Figure 2B:
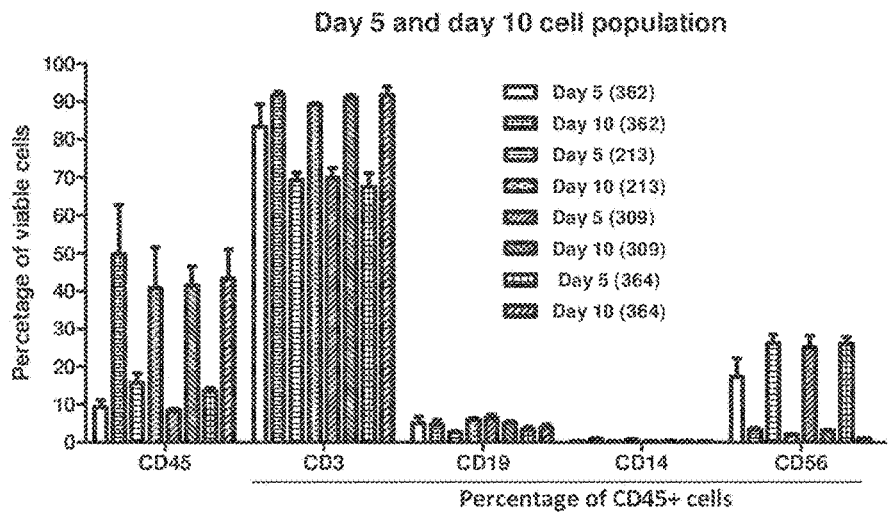
FIG. 2B depicts different cell populations on day 5 or day 10 after engraftment in NSG mice of 2×10$^7$ hPBMCs/mouse from four different donors, 362, 213, 309 and 364. 2-5 mice per group per each time point and data are presented as mean±SEM.

On day 3 after engraftment, there are insufficient cells numbers. The present inventors found that on day 5 there are sufficient human cell types and the number of these human cells are optimal for testing (human CD45%>10%). But on day 10, many cells types' cell number (percentage of total viable cells) decreases. For example, NK cells decreased from 20-30% on day 5 to 1-5% on day 10 (FIGS. 2B and 2C). Thus, the present method includes administering the drug to the humanized mouse between days 4 and 7, or between days 5 and 7, or day 6 after engraftment.

Figure 4A:
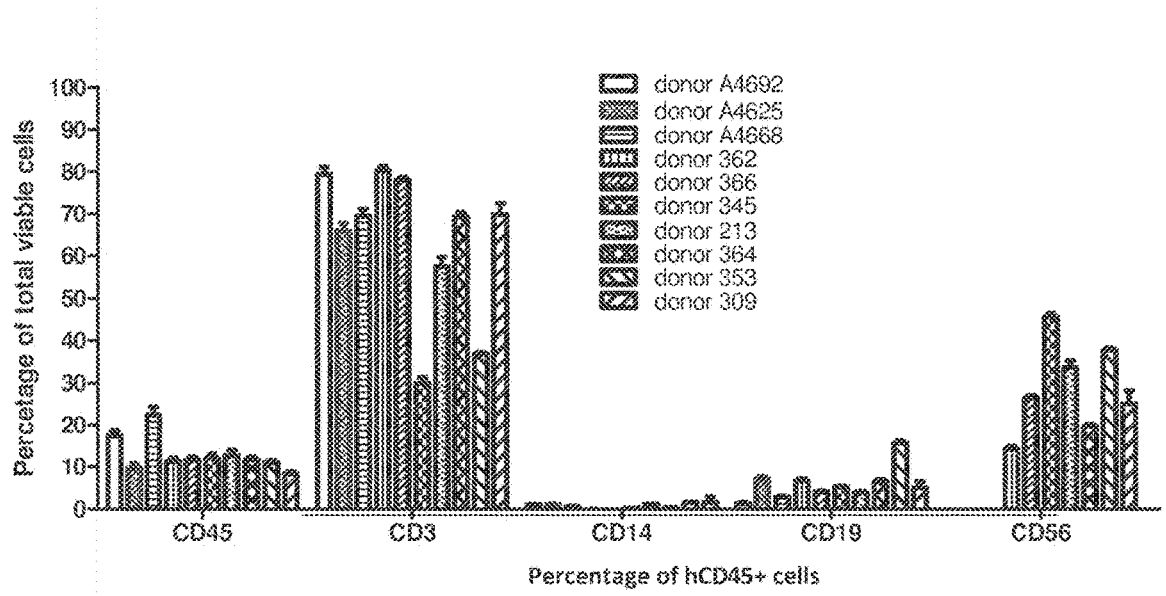
FIG. 4A depicts the comparisons among 10 donors' PBMC reconstitution in humanized mice on day 5 (2×10$^7$ hPBMCs/mouse engraftment). Humanized NSG mice were tested for the indicated immune-cell subset reconstitution by flow cytometry. Human CD45+ cells as a percentage of total cells, as well as CD3, CD19, CD14, and CD56, as a percentage of CD45+ cells (gated on CD45+ cells) are shown. (Donors A4692, A4625, and A4668 only showed CD45, CD3, CD19 and CD14, but not CD56).

It is believed that many lymphoid, myeloid, and potentially other human immune cell types are required to participate in an immune toxicity response, and this includes T cells and NK cells, which play an important role. In the present PBMC humanized mouse model, the inventors found that there are different human cell types present in mice at an early time point. Human T cells and NK cells are predominant cells population in those mice on day 5 of engraftment, (FIG. 2 and FIG. 4A).

It is also believed that for optimal toxicity testing, there requires a critical level of human cells in the mouse. When human PBMCs are injected into a mouse, only human T cells can expand; other cell types will begin to die out with time. An intricate balance is needed between cell number (i.e., the number of PBMCs administered to the mouse) and cell types with time.

Additionally, the present inventors discovered that experiments need to be performed before the mice develop graft versus host disease GVHD, which is manifested by body weight loss. As discussed further below, after 8 days, the inventors observed significant weight loss of many of the humanized mice engrafted with PBMC, which is indicative of severe graft versus host disease GVHD. It is generally believed that human T cells in the mouse cannot grow forever; they will attack the mouse when the T cells number is high, with release of cytokines, and cause GVHD. If the mice have GVHD, it will affect the accuracy of the testing results since cytokines are released when the human T cells attack mouse cells (Ju X P et al. Transplantation. 1997; 63(9):1307-1313). The mice will eventually die due to GVHD.

Figure 3A:
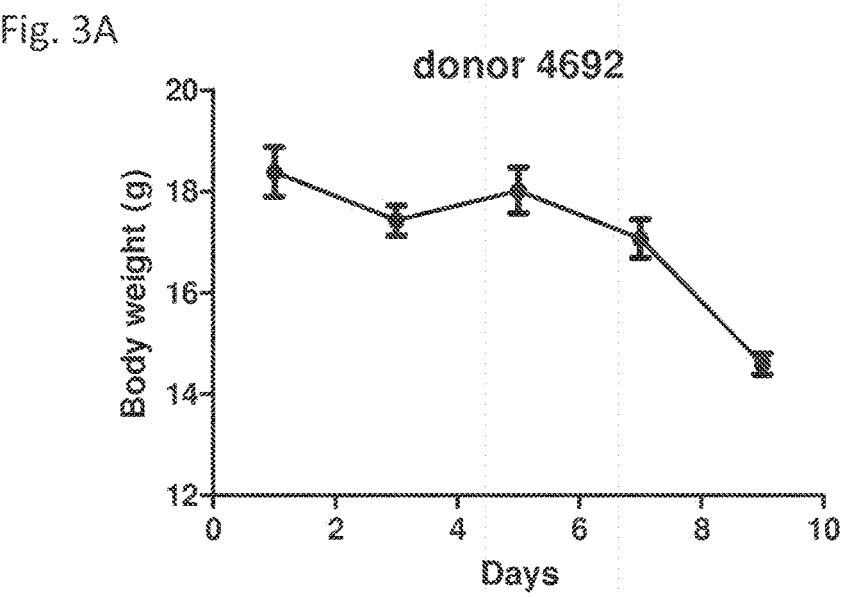
FIG. 3A depicts body weight measurement of 5 NSG mice engrafted with donor 4692 at 5×10$^7$ hPBMC/mouse. Data are the mean±SEM.
Figure 3B:
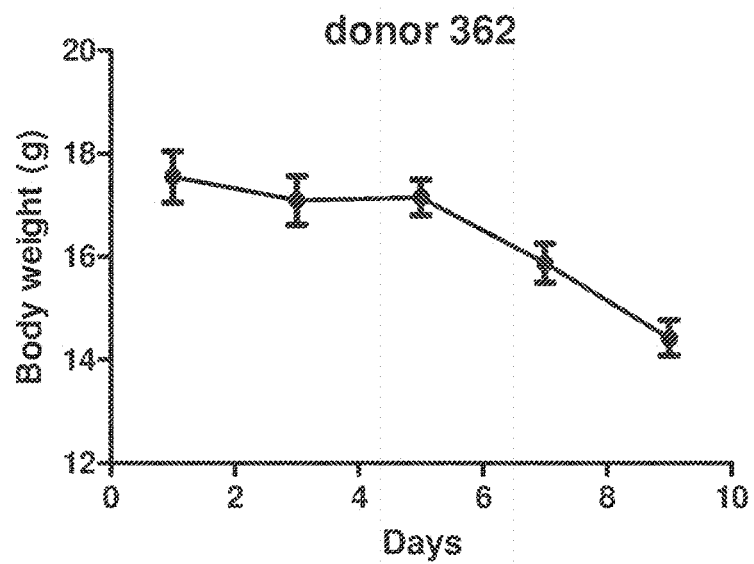
FIG. 3B depicts body weight measurement of 5 NSG mice engrafted with donor 362 at 5×10$^7$ hPBMC/mouse. Data are the mean±SEM.
Figure 3C:
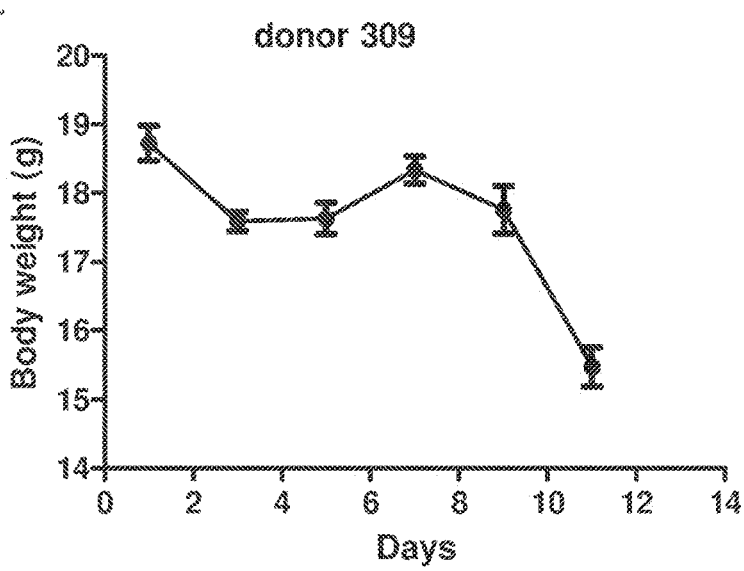
FIG. 3C depicts body weight measurement of 5 NSG mice engrafted with donor 309 at 2×10$^7$ hPBMC/mouse. Data are the mean±SEM.
Figure 3D:
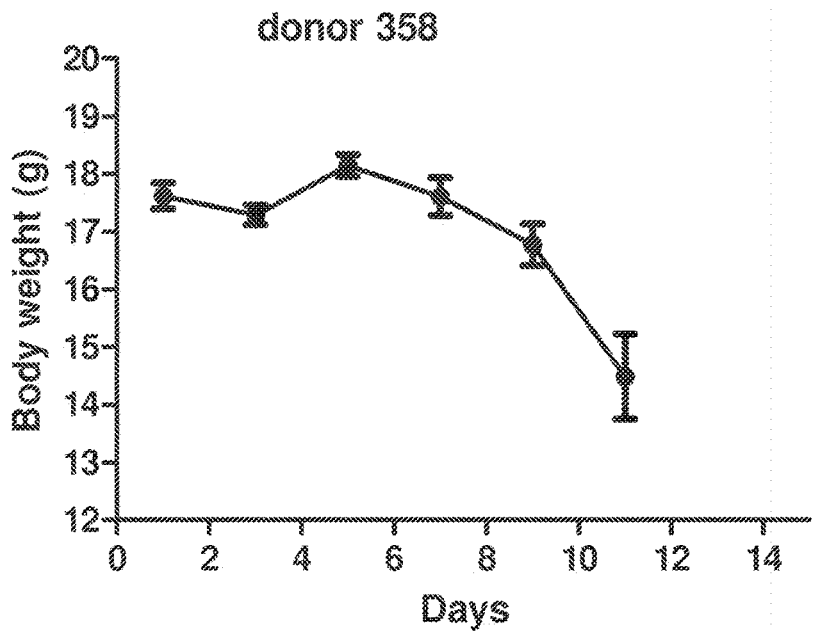
FIG. 3D depicts the body weight measurement of 4 NSG mice engrafted with donor 358 at 3×10$^7$ hPBMC/mouse. Data are the mean±SEM.

Data of examples of GVHD are depicted in FIGS. 3A-3D. In FIGS. 3A and 3B, engrafting PMBC from donors 4629 and 362 in a mouse caused significant body weight loss as early as day 6 after $5 \times 10^7$ PBMC engraftment. FIG. 3C shows that for donor 309, mice receiving $2 \times 10^7$ PMBCs started body weight loss after day 8, while FIG. 3D shows mice receiving $3 \times 10^7$ PMBCs from donor 358 started body weight loss after day 7.

In addition, these mice with GVHD were sick after 8 days, and therefore were no longer suitable for the study. The present inventors observed not only weight loss, they also exhibited hunched posture, fur loss, reduced mobility, and tachypnea. After weight loss of 20%, the mice had to be euthanized.

Thus, to ensure that the mouse is not suffering from GVHD or otherwise sick, it is critical that the immunomodulatory drug is administered before 8 days after engrafting with PBMCs. Further, the drug cannot be administered too early because there may not be enough cells as early as e.g. day 3. There need to be enough circulating cells for the tests to be accurate.

Thus, in view of the above factors, in certain embodiments, the immunomodulatory drug is administered to the mice at 5-7 days after engrafting the mice with PBMCs. In some preferred embodiments, the immunomodulatory drug is administered to the mice at 6 days after engrafting with PBMCs. During this period of time, the mouse should be kept under suitable conditions, including meeting the basic needs (e.g., food, water, light) of the mammal as known to those of skill in the art.

In the examples set forth below, the inventors chose day 6 for the experiments of 10 donors. Methods for measuring increased expression of one or more pro-inflammatory cytokines (human or mouse) are also known to those skilled in the art. Pro-inflammatory human cytokines include IL-2, IL-6, IL-8, IL-113, IL-4, gamma interferon (IFN-γ), tumor necrosis factor alpha (TNF-α, or "TNF"), IL-10, or a combination thereof. Increased expression of pro-inflammatory cytokines can be determined as described herein using flow cytometry.

In another aspect, there is disclosed a method of determining whether a combination of immunomodulatory drugs likely elicits a severe cytokine release syndrome (CRS) in a human following administration of the combination of immunomodulatory drugs. In one embodiment, the combination includes a first immunomodulatory drug and a second immunomodulatory drug. In another embodiment, the method comprises providing an immunodeficient mouse, said mouse is irradiated with 75-125 cGy X-ray; engrafting $1.5$-$3.0 \times 10^7$ peripheral blood mononuclear cells (PBMCs) isolated from a human to the immunodeficient mouse to produce a humanized mouse; administering to the humanized mouse a first immunomodulatory drug and a second immunomodulatory drug 5-7 days after engrafting with the PBMCs; determining blood concentration in the humanized mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and determining the combination of immunomodulatory drugs likely elicits a severe cytokine release syndrome in the human, wherein presence of a severe cytokine release syndrome in the mouse is indicative that administration of the combination of immunomodulatory drugs likely elicits a severe cytokine release syndrome in the human.

The number of PBMCs engrafted per mouse can be $2 \times 10^7$ PBMCs. The immunodeficient mouse can be an NSG mouse, an NSG-IL-6 mouse, or an NSG-CSF-1 mouse, preferably an NSG mouse. The immunodeficient mouse can be irradiated prior to engraftment with 100 cGy X-ray. The administration of the drugs can be performed 6 days after engraftment. The plurality of cytokines can further comprise IL-2, IL-4, IL-6, or TNF. The cytokine concentration can be determined for each of IFN-γ, IL-10, IL-6, IL-2, IL-4, and TNF. The blood concentration of the plurality of cytokines is determined 2 to 6 hours, preferably 6 hours, following administration of said combination of immunomodulatory drugs.

In one exemplary combination of multiple immunomodulatory drugs, the immunomodulatory drugs can independently be selected from an anti-CD28 monoclonal antibody (mAb), an anti-CD3 mAb, an anti-CD20 mAb, an anti-CD52 mAb; granulocyte colony-stimulating factor (G-CSF); an interferon; imiquimod; thalidomide and its derivatives or analogues, such as lenalidomide (REVLIMID®), pomalidomide (IMNOVID®), and apremilast; azathioprine, cladribine, cyclophosphamide, intravenous immunoglobulin, methotrexate, mitoxantrone; IMLYGIC™ (talimogene laherparepvec); adalimumab (HUMIRA®), catumaxomab (REMOVAB®), ibritumomab tiuxetan (ZEVALIN®), tositumomab-$I^{131}$ (BEXXAR®), brentuximab vedotin (ADCETRIS®), betuximab (ERBITUX®), rituximab (MABTHERA® or RITUXAN®), alemtuzumab (CAMPATH-1H®, CAMPATH®, or LEMTRADA®), bevacizumab (AVASTIN®), pertuzumab (PERJETA®), trastuzumab (HERCEPTIN®), trastuzumab emtansinen (KADCYLA™), denosumab (PROLIA® or XGEVA®), ofatumumab (ARZERRA®), panitumumab (VECTIBIX®), pembrolizumab (KEYTRUDA®), nivolumab (OPDIVO®), ipilimumab (YERVOY®), atezolizumab (TECENTRIQ®), avelumab (BAVENCIO®), and durvalumab daratumumab (DARZALEX®), ceritinib (ZYKADIA®), and anti-thymocyte globulin (THYMOGLOBULIN® (rabbit) or ATGAM® (equine)).

In another exemplary combination, the first immunomodulatory drug and the second immunomodulatory drug are independently selected from the group consisting of anti-CD28 mAb, anti-CD3 mAb, anti-CD20 mAb, anti-CD52 mAb, granulocyte colony-stimulating factor (G-CSF); an interferon; imiquimod; thalidomide, lenalidomide, pomalidomide, apremilast; azathioprine, cladribine, cyclophosphamide, intravenous immunoglobulin, methotrexate, mitoxantrone; talimogene laherparepvec; adalimumab, catumaxomab, ibritumomab tiuxetan, tositumomab-$I^{131}$, brentuximab vedotin, betuximab, rituximab, alemtuzumab, bevacizumab, pertuzumab, trastuzumab, trastuzumab emtansinen, denosumab, ofatumumab, panitumumab, pembrolizumab, nivolumab, ipilimumab, atezolizumab, avelumab, durvalumab, daratumumab, ceritinib, elotuzumab, and anti-thymocyte globulin. The anti-CD52 mAb can be alemtuzumab, the anti-C20 mAb can be rituximab, the anti-CD3 mAb can be OKT3, and the anti-CD28 mAb can be TGN1412.

In one preferred embodiment, the first immunomodulatory drug is pembrolizumab or nivolumab and the second immunomodulatory drug is lenalidomide, pomalidomide, epacadostat, talimogene laherparepvec, ipilimumab, atezolizumab, avelumab, rituximab, alemtuzumab, ceritinib, daratumumab, elotuzumab, or durvalumab. In another preferred embodiment, the first immunomodulatory drug is pembrolizumab and the second immunomodulatory drug is lenalidomide. In another preferred embodiment, the first immunomodulatory drug is pembrolizumab and the second immunomodulatory drug is pomalidomide.

In one preferred embodiment, the first immunomodulatory drug is nivolumab and the second immunomodulatory drug is lenalidomide. In another preferred embodiment, the first immunomodulatory drug is nivolumab and the second immunomodulatory drug is pomalidomide. In another preferred embodiment, the first immunomodulatory drug is nivolumab and the second immunomodulatory drug is elotuzumab. In another preferred embodiment, the first immunomodulatory drug is nivolumab and the second immunomodulatory drug is daratumumab. In one preferred embodiment, the first immunomodulatory drug is nivolumab and the second immunomodulatory drug is ipilimumab.

In another preferred embodiment, the first immunomodulatory drug is ipilimumab and the second immunomodulatory drug is lenalidomide, pomalidomide, pembrolizumab, atezolizumab, avelumab, rituximab, alemtuzumab, ceritinib, daratumumab, or durvalumab.

In another preferred embodiment, the first immunomodulatory drug is atezolizumab, avelumab, or durvalumab and the second immunomodulatory drug is lenalidomide, pomalidomide, pembrolizumab, ipilimumab, rituximab, ceritinib, daratumumab, or alemtuzumab. In another preferred embodiment, the first immunomodulatory drug is durvalumab and the second immunomodulatory drug is lenalidomide. In another preferred embodiment, the first immunomodulatory drug is durvalumab and the second immunomodulatory drug is rituximab. In another preferred embodiment, the first immunomodulatory drug is durvalumab and the second immunomodulatory drug is pomalidomide. In another preferred embodiment, the first immunomodulatory drug is durvalumab and the second immunomodulatory drug is daratumumab. In yet another preferred embodiment, the first immunomodulatory drug is durvalumab and the second immunomodulatory drug is ibrutinib.

In one preferred embodiment, the first immunomodulatory drug is elotuzumab and the second immunomodulatory drug is pomalidomide. In another preferred embodiment, the first immunomodulatory drug is atezolizumab and the second immunomodulatory drug is pomalidomide, In another preferred embodiment, the first immunomodulatory drug is atezolizumab and the second immunomodulatory drug is lenalidomide.

In another aspect, the present invention provides a method of determining a safe dosage of an immunomodulatory drug that elicits no cytokine release syndrome in a human following administration of the immunomodulatory drug is disclosed. The present method can comprise providing an immunomodulatory drug having a first dosage, said first dosage of the immunomodulatory drug is determined to elicit a mild or severe cytokine release syndrome in a first irradiated humanized immunodeficient mouse following its administration; providing a second immunodeficient mouse, said second mouse is irradiated with 75-125 cGy X-ray; engrafting $1.5$-$3.0 \times 10^7$ peripheral blood mononuclear cells (PBMCs) isolated from a human to said second mouse; administering to said second mouse an immunomodulatory drug 5-7 days after engrafting with the PBMCs, said immunomodulatory drug is administered at a second dosage that is lower than said first dosage; determining blood concentration in said second mouse of a plurality of cytokines comprising IFN-γ and IL-10; and determining a safe dosage of said immunomodulatory drug for administration in said human, said safe dosage is a dosage producing a blood concentration of IFN-γ is <300 pg/ml and IL-10 is <25 pg/ml following administration of said immunomodulatory drug to said second mouse, wherein blood concentration of IFN-γ<300 pg/ml and IL-10<25 pg/ml in said second mouse is indicative that administration of said safe dosage of said immunomodulatory drug likely elicits no cytokine release syndrome in said human.

In another embodiment, the present method provides the optimization of a safe dosage for an immunomodulatory drug that is suspected of eliciting a mild or severe cytokine release syndrome in a human. The present method comprises: providing an immunodeficient mouse, said mouse is irradiated with 75-125 cGy X-ray; engrafting $1.5$-$3.0 \times 10^7$ peripheral blood mononuclear cells (PBMCs) isolated from a human; administering to said mouse an immunomodulatory drug 5-7 days after engrafting with the PBMCs, said immunomodulatory drug is administered at a dosage that is lower than that which is suspected of eliciting a mild or severe cytokine release; determining blood concentration in said mouse of a plurality of cytokines comprising IFN-γ and IL-10; and determining a safe dosage of said immunomodulatory drug for administration in said human, said safe dosage is a dosage producing a blood concentration of IFN-γ is <300 pg/ml and IL-10 is <25 pg/ml following administration of said immunomodulatory drug to said mouse, wherein blood concentration of IFN-γ<300 pg/ml and IL-10<25 pg/ml in said mouse is indicative that administration of said safe dosage of said immunomodulatory drug likely elicits no cytokine release syndrome in said human.

The number of PBMCs engrafted per mouse can be $2 \times 10^7$ PBMCs. Exemplary immunodeficient mouse includes an NSG mouse, an NSG-IL-6 mouse, an NSG-CSF-1 mouse, and the like. Preferably, immunodeficient mouse is an NSG mouse. In preferred embodiments, the immunodeficient mouse is irradiated prior to engraftment with 100 cGy X-ray.

The administration of the drugs can be performed 6 days after engraftment. The plurality of cytokines can further comprise IL-2, IL-4, IL-6, or TNF. The blood concentration of the plurality of cytokines can be determined 2 to 6 hours after administration of the immunomodulatory drug, preferably 6 hours after administration of the immunomodulatory drug. The immunomodulatory drug can be any of those disclosed herein. For example, the immunomodulatory drug can be anti-CD28 mAb, anti-CD3 mAb, anti-CD20 mAb, anti-CD52 mAb, pembrolizumab, ipilimumab, atezolizumab, avelumab, durvalumab, epacadostat, talimogene laherparepvec, nivolumab, lenalidomide, ceritinib, or anti-thymocyte globulin.

In another aspect, the present invention provides an in vitro method of determining likelihood that administration of an immunomodulatory drug to a human will induce cytokine release syndrome in the human comprises: providing a blood sample from a humanized, irradiated, immunodeficient mouse administered an immunomodulatory drug 5-7 days after engraftment with $1.5$-$3.0 \times 10^7$ isolated peripheral blood mononuclear cells (PBMCs) from a human; and detecting in vitro the concentration of a plurality of cytokines comprising IFN-γ and/or IL-10 present in the blood sample of the mouse, wherein a concentration of IFN-γ≥1,800 pg/ml or of IL-10≥120 pg/ml in the mouse blood sample is indicative that administration of the immunomodulatory drug to the human is likely to induce a severe cytokine release syndrome.

In another aspect, the present invention provides a method of determining likelihood that administration of a combination of a first immunomodulatory drug and a second immunomodulatory drug to a human will induce a severe cytokine release syndrome in the human is disclosed. The present method can comprise providing a blood sample from a humanized, irradiated, immunodeficient mouse administered a combination of a first immunomodulatory drug and a second immunomodulatory drug 5-7 days after engraftment with $1.5$-$3.0 \times 10^7$ isolated peripheral blood mononuclear cells (PBMCs) from a human; and detecting in vitro the concentration of a plurality of cytokines comprising IFN-γ and/or IL-10 present in the blood sample of the mouse, wherein a concentration of IFN-γ≥1,800 pg/ml or of IL-10≥120 pg/ml is indicative that administration of the combination of the first immunomodulatory drug and the second immunomodulatory drug to the human is likely to induce a severe cytokine release syndrome.

According to further aspects, the present invention provides a humanized mouse model as a drug screening platform with accuracy to identify from a large number of clinically relevant drug candidates for clinical evaluation. The present assay eliminates the potential drug candidates that elicit cytokine release in humans and thus represents a robust prediction tool for drug immunotoxicity testing.

The present assay represents a drug testing assay for drug candidate(s) that may adversely affect the immune system in humans. The present assay may also provide drug testing for a drug candidate or combinations of drug candidates. The model provides the necessary link between preclinical and clinical testing. The integration of the present assay into drug development programs should accelerate the FDA approval process for therapeutic drug development. The drug candidate or combinations of drug candidates in these methods are not limited to immunomodulatory drugs mentioned with regard to other embodiments herein, but may include any drug candidates that may have a therapeutic effect with regard to treating, alleviating, and/or curing a disease, illness, ailment, injury or other condition.

Accordingly, in another aspect, the present invention is directed to a method of determining whether a drug candidate causes immune toxicity in a human. The method comprises administering the drug to a non-human immunodeficient mammal (e.g., NSG, NSG-CSF-1, or NSG-IL-6 mouse) that has been engrafted with human peripheral blood mononuclear cells (hPBMCs) and determining whether the drug causes immune toxicity in humans, by determining if the drug causes immune toxicity in the non-human mammal.

Accordingly, the present invention provides an in vivo method of determining immunotoxicity of a drug candidate for use in a human comprising the steps of: (a) providing an immunodeficient mouse, said mouse is irradiated with 75-125 cGy X-ray; (b) engrafting $4.5-5.5 \times 10^7$-$5.5 \times 10^7$ human PBMCs, preferably $5.0 \times 10^7$ human PBMCs, into the mouse (e.g., NSG, NSG-IL-6, or NSG-CSF-1); (c) administering a drug candidate to the mouse 4-7 days after engrafting; (d) determining cytokine concentration in blood of said mouse, wherein said cytokine is at least one cytokine selected from the group consisting of IFN-$\gamma$, IL-2, IL-4, IL-6, IL-10, and TNF; and (e) determining immunotoxicity of said drug candidate, wherein blood concentration in said mouse of at least one cytokine selected from the group consisting of IFN-$\gamma \geq 300$ pg/ml, IL-2$\geq 15$ pg/ml, IL-4$\geq 10$ pg/ml, IL-6$\geq 10$ pg/ml, IL-10$\geq 25$ pg/ml, or TNF $\geq 5$ pg/ml is indicative of an immunotoxicity of said drug candidate in a human. The immunodeficient mouse can be an NSG mouse, an NSG-IL-6 mouse, or an NSG-CSF-1 mouse, preferably an NSG mouse. In a preferred embodiment, the immunodeficient mouse is irradiated with 100 cGy X-ray. Cytokine release can be determined in blood of the mouse 2 to 6 hours after drug candidate administration, preferably 6 hours after drug candidate administration.

In an embodiment, a method of determining human immunotoxicity of a drug candidate comprises engrafting $4.5 \times 10^7$-$5.5 \times 10^7$ of human PBMCs to an irradiated, immunodeficient mouse; administering to said mouse a drug candidate 4-7 days, preferably 5-7 days after engrafting, more preferably 6 days, after engrafting; determining cytokine release in blood of said mouse, wherein the cytokine is at least one cytokine selected from the group consisting of IFN-$\gamma$, IL-2, IL-4, IL-6, IL-10, and TNF; and identifying that the drug candidate has low human immunotoxicity when low cytokine release is detected in blood of the mouse. In an embodiment, a method of determining human immunotoxicity of a drug candidate comprises providing a blood sample from a humanized, irradiated, immunodeficient mouse administered a drug candidate 4-7 days, preferably 5-7 days after engrafting, more preferably 6 days, after engraftment with $4.5-5.5 \times 10^7$ isolated human peripheral blood mononuclear cells (PBMCs); and detecting in vitro the concentration of at least one human cytokine present in the mouse blood sample to determine human immunotoxicity of the drug candidate, wherein the at least one human cytokine is selected from the group consisting of IFN-$\gamma$, IL-2, IL-4, IL-6, IL-10, and TNF$\alpha$ and wherein the drug candidate has low human immunotoxicity when low human cytokine concentration is detected in the mouse blood sample. The immunodeficient mouse can be an NSG mouse, an NSG-IL-6 mouse, or an NSG-CSF-1 mouse, preferably said immunodeficient mouse is an NSG mouse. The immunodeficient mouse can be irradiated with 75-125 cGy X-ray, preferably the immunodeficient mouse is irradiated with 100 cGy X-ray. Cytokine release can be determined in blood of the mouse 2 to 6 hours after drug candidate administration, preferably 6 hours after drug candidate administration. Low cytokine release in blood of the mouse can comprise IFN-$\gamma < 300$ pg/ml, IL-10$<25$ pg/ml, IL-2$<15$ pg/ml, IL-4$<10$ pg/ml, IL-6$<10$ pg/ml, or TNF$<5$ pg/ml. Low cytokine release in blood of the mouse can comprise an amount of the cytokine no more than the amount of the cytokine induced by administration of a negative control.

The present invention further provides a step for identifying whether the drug candidate(s) and/or drug combinations have a safety profile suitable for FDA approval, wherein a low cytokine release is indicative of a safety profile suitable for FDA approval. According to non-limiting example embodiments $4.5 \times 10^7$-$5.5 \times 10^7$ human PBMCs are engrafted into an irradiated, immunodeficient mouse. According to other non-limiting example embodiments, $5.0 \times 10^7$ human PBMCs are engrafted into an irradiated, immunodeficient mouse. The PBMCs engrafted in the method of determining the safety profile can be from a single individual or from a pool of humans. According to preferred embodiments, the immune deficient mouse is irradiated with 75 cGy-125 cGy X-ray at least four hours before PBMCs are engrafted into the immunodeficient mouse. According to other preferred embodiments, the immune deficient mouse is irradiated with 1100 cGy X-ray at least four hours before PBMCs are engrafted into the immunodeficient mouse. The response to the drug may be evaluated in comparison to a control agent for example. The present assay enables the determination of a drug candidate passes the pharmaceutical safety evaluation.

According to other example embodiments, the present invention provides a humanized, irradiated, immunodeficient mouse engrafted with human peripheral blood mononuclear cells, said humanized, irradiated, immunodeficient mouse being a NOD.Cg-Prkdc$^{scid}$Il2rg$^{tm1wjl}$/SzJ (NSG) mouse. Preferably, the mouse is engrafted with $1.5-3.0 \times 10^7$ PBMCs. The NSG mouse can further comprise a human macrophage colony-stimulating factor-1 gene (NSG-CSF-1) or a human interleukin-6 gene (NSG-IL-6). More preferably, the mouse is engrafted with $2 \times 10^7$ PBMCs. According to other example preferred embodiments, the mouse is engrafted with $4.5-5.5 \times 10^7$ PBMC.

According to other example embodiments, the present invention provides a humanized immunodeficient mouse engrafted with human peripheral blood mononuclear cells, said humanized immunodeficient mouse being a NOD.Cg-Prkdc$^{scid}$Il2rg$^{tm1wjl}$/SzJ (NSG) mouse having a human macrophage colony-stimulating factor-1 gene (NSG-CSG-1). Preferably, the mouse is engrafted with $1.5-3.0 \times 10^7$ PBMCs. More preferably, the mouse is engrafted with $2 \times 10^7$ PBMCs. According to other example preferred embodiments, the mouse is engrafted with $4.5-5.5 \times 10^7$ PBMC.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

The following examples are provided to further illustrate various non-limiting embodiments and techniques of the present method, including experiments performed in developing the present method. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

Engraftment of Human PBMCs in Humanized Mice

In this study, two strains of humanized immunodeficient mice were used: 6-week old female (i) NOD.Cg-Prkdc$^{scid}$Il2rg$^{tm1wjl}$/SzJ (NSG, JAX stock number 005557) mice and (ii) NSG-CSF-1 mice (Jackson Laboratory Stock No: 028654). The mice were irradiated with 100cGy X-ray at least 4 hours prior to human PBMC engraftment. Purified/isolated human PBMCs (Astarte Biologics or Allcells) from the same donor were intravenously (iv) injected into NSG or NSG-CSF-1 mice at 1-5×10$^7$ cells/mouse. Following hPBMC injection, mice were observed daily for body weight, general appearance of the fur, and mobility.

FIG. 1A shows the daily body weight changes in ten NSG or NSG-CSF-1 mice after hPBMC engraftment at 2×10$^7$ hPBMC/mouse, presented as the mean±the standard error of the mean (SEM). FIG. 1B depicts the body weight measurements of five individual NSG mice after hPBMC engraftment (2×10$^7$ hPBMC/mouse). Each line represents one mouse. It was observed that most of the mice exhibited a significant weight loss beginning at day 8. Moreover, in addition to loss of body weight after the engraftment, the mice started to show graft versus host disease (GVHD), as discussed further below.

Example 2

Dynamics in Human Engrafted Cell Types and Cell Numbers At Different Time Points After Engraftment In this experiment, cell types and cell numbers of engrafted human mononuclear cells from different human donors were studied after the hPBMCs engraftment of three different strains of mice. Mice were bled at day 5 or/and day 10 after engraftment and human cells (types and percentages) were analyzed by flow cytometry. Specifically, the mouse PBMCs (in mixture with hPBMCs) were stained with human antibodies: anti-CD45, anti-CD3, anti-CD14, anti-CD19, and anti-CD56.

NSG, NSG-IL-6 (Jackson Laboratory Stock No. 028655) and NSG-CSF-1 mice were used for testing the human cells reconstitution (i.e., human cells showed different percentage of total viable cells at different time points after engraftment). FIG. 2A shows that NSG, NSG-IL-6, and NSG-CSF-1 mice reconstitution exhibited comparable human cells on day 5 after engraftment with hPBMCs from donor 331. The results indicate that there was no significant difference between these three mouse strains. All three strains of mice have about 20% human CD45 cells reconstitution on day 5 of engraftment. Among the human CD45 cells, most of them were CD3 T cells and NK cells (FIG. 2A).

In another study, the different cell populations were examined at two different time points after engraftment in NSG of hPBMCs from different donors (FIG. 2B, 2×10$^7$PBMC/mouse) or donor 358 (FIG. 2C, 3×10$^7$PBMC/mouse). In these experiments, 2-5 mice per group per each time point were used and the data are presented as mean±SEM. As shown in FIGS. 2B and 2C, there were ~10 to 15% human CD45+ on day 5, and 35 to 50% CD45+ on day 10. These data indicate that engrafted human CD45 cells increased in the humanized mice over time. Of interest is the observation that on day 5, 20-30% CD56 (NK) cells were present in the population of CD45+ cells in the humanized mice. However, on day 10, CD56 (NK) cells decreased substantially, to 1-5%. These data suggest that the increase in percent CD45 correlates with the disappearance of specific mononuclear cell types (e.g., CD56 NK cells). In sum, there is a dynamic change in cell type and cell number of the engrafted mononuclear cells in the humanized immune deficient mice after engraftment of hPMBCs. T cells and NK cells are predominant cells types on day 5, but on day 10, only T cell type is predominate cell type, NK cells die out with time. For the present methods to work, there must be a balance such that not all of the NK cells die out at the time of drug testing (e.g., at day 10).

The hPBMC humanized mouse model is considered a T-cell model, because the human T cells are the predominant cell population along with the time after human cells reconstitution. The results from this example confirmed this. FIGS. 2B and 2C showed that among human CD45 cells that increased from 10 to 15% at day 5 after engraftment to 35 to 50% at day 10, the CD3 T cell percentage increased from 65 to 80% at day 5 to 90 to 95% at day 10.

There are a lot of cell types involved in immune toxicity response. T cells, NK cells and monocytes cells all play very important roles. In the hPBMC humanized mouse model, it was found that there are different human cell types still in mice at an early time point after engraftment. Human T-cells and NK cells are predominant in the cell population in the hPBMC humanized mice on day 5 of engraftment, FIGS. 2B and 2C. This finding gave the inventors an opportunity to study the immune toxicity response in hPBMC humanized mice. An early time point after engraftment, for example, day 6 was chosen to do the testing for immune toxicity and CRS.

Mice were irradiated on day 0 and were engrafted with hPBMC on the same day. The mice's body weight dropped from day 1 to day 3 because of the irradiation. After day 4, the mice started to add weight. Apparently, as shown in FIG. 1A, NSG mice have more weight compared to NSG-CSF-1. The NSG mice also looked healthier and more active. Therefore, NSG mice were used for later testing.

Example 3

Criticality of Engraftment Time

In this study, the basis for weight lost in some of the humanized mice was examined after hPBMC engraftment. Significant weight loss was observed in a number of mice, indicative of graft versus host disease (GVHD) in these mice. Data for examples of GVHD are depicted in FIGS. 3A, 3B, 3C, and 3D.

FIGS. 3A and 3B depict body weight measurements of 5 humanized NSG mice as a function of time after engraftment with 5×10$^7$ PBMCs/mouse in an NSG mouse for donor 4692 and donor 362, respectively. This level of engrafted cells caused a significant body weight loss (10%) after day 7 post-engraftment of PBMCs from either donor. A ~20% body weight loss represents a severe state of GVHD in the mouse and requires euthanasia of the mouse.

FIG. 3C depicts body weight measurements of 5 humanized NSG mice as a function of time after donor 309 engraftment ($2 \times 10^7$ PBMCs/mouse). Significant body weight loss (10%) is observed after day 8 post-engraftment of PBMCs.

FIG. 3D shows body weight measurements of 4 humanized NSG mice as a function of time after donor 358 engraftment ($3 \times 10^7$ PBMCs/mouse). The mice receiving the PMBCs from donor 358 started significant body weight loss (10%) on day 9 after engraftment.

It is believed that GVHD accounted for the observed body weight loss. As engrafted human T-cells in the mouse began to grow, they attack the mouse cells. As discussed in Example 2 above, there was an increase in % of CD45 cells with time after engraftment and when the T-cell number is high, the mice with GVHD became sick after 8 days, and were no longer suitable for the study.

GVHD mice not only exhibited weight loss, they also showed signs of hunched posture, fur loss, reduced mobility, and tachypnea. After weight loss of 20%, the mice had to be euthanized and experiments were terminated. Frequent occurrence of GVHD after 8 days of engraftment reveals another aspect of the criticality of the timing of human PBMC engraftment prior to the administration of immunomodulatory drugs for the toxicity testing.

Immunomodulatory drugs cannot be administered too early after engraftment (e.g., day 2-3) because there may not be sufficient circulating cell numbers and types in the mice to produce reliable and reproducible results.

If the mice have GVHD however, it will affect the testing results. Therefore, in subsequent experiments day 6 after cells engraftment was chosen for testing the effects of drug administration on more donors.

Different cytokines may release at different time points after drug administration. The earliest released cytokine should be TNF, which always peaks before or on 1 hour after drug administration. Further, most cytokines would be back to normal levels after 24 hours if there is no organ failure. Therefore, 2 and 6 hours after drug administration were chosen as times for bleeding the mice and testing the serum for cytokine concentration.

Example 4

Human T-Cells and NK Cells Represent Predominant Cell Populations in hPBMCs Humanized NSG Mice on Day 5 of Engraftment In this study, ten (10) donors' mononuclear cell reconstitution was examined and compared in humanized mice. Each mouse was engrafted with $2 \times 10^7$ hPBMCs from a donor. The de-identified patient information of seven of the ten donors is set forth in FIG. 4B.

Five humanized NSG mice for each donor were tested for the indicated immune-cell subset reconstitution by flow cytometry. In hPBMC-injected NSG mice, on day 5 of reconstitution, the whole blood was analyzed by flow cytometry. Human CD45, CD3, CD19, CD14, and CD56 were measured. Human CD45+ cells as a percentage of total cells, as well as CD3, CD19, CD14, and CD56, as a percentage of CD45+ cells (gated on CD45+ cells), are shown for the 10 donors in FIG. 4A. Donors A4692, A4625 and A4668 only showed CD45, CD3, CD19, and CD14. The humanized mice showed an average of 10-25% of human CD45+ cells in peripheral blood (FIG. 4A). Among the human CD45 cells, there were 30-80% T cells and 10-40% CD56 (NK) cells, with variation shown among the different donors.

In subsequent experiments, a day in the range of days 5-7 after engraftment was chosen as the optimal time to administer immunomodulatory drugs to the mice for toxicity testing.

Example 5

Cytokines Release Induced by Immunomodulatory Drugs in Humanized Mice

To establish a humanized mouse model for screening and determining the drug immune toxicity, cytokine release syndrome (CRS), for pre-clinical testing and clinical trials, a positive control is needed for all patients. ORTHOCLONE OKT3, also referred to as muromonab-CD3, is a murine monoclonal antibody (mAb) (anti-CD3 mAb) that was used as an immunosuppressant drug to immunosuppress transplant recipients. OKT3 binds the CD3 receptor, which can activate T cells to release cytokines, causing cytokine release syndrome (CRS). OKT3 was used as positive control for all patients. For testing the method's specificity and sensitivity, a target drug needed to be chosen that has few methods to test its immune toxicity. An anti-CD28 mAb was chosen as a target drug for evaluation of the present method's specificity and sensitivity.

PBMCs of nine (10) different donors were used to produce humanized NSG mice for these experiments. On day 6 of hPBMC engraftment ($2 \times 10^7$ PBMCs/mouse), the mice were induced for human cytokine release by i.v. injection with antibodies OKT3 (anti-CD3 mAb; BioLegend, Cat. No. 317302) or ANC28.1/5D10 (also referred to as "ANC28", "anti-CD28 mAb," or "anti-CD28"; Ancell, Cat. No. 177-824). PBS buffer served as a negative control. The mice were bled at 2 and 6 hours, sera were collected and analyzed for cytokine concentrations using BD Cytometric Bead Array (CBA) Human Th1/Th2 Cytokine kit II (BD, Cat. No. 551809) (See, FIGS. 5A-5F).

FIGS. 5A-5F depict multiple graphs of concentration of different cytokines (i.e., IFN-γ, IL-6, IL-2, IL-10, IL-4, and TNF, respectively) measured at 2 and 6 hours after injection of antibodies OKT3 (anti-CD3 mAb) and ANC28 (anti-CD28) into sets of humanized mice for nine (9) different donors. Mice were i.v. injected with 0.5 mg/kg OKT3 or 1 mg/kg anti-CD28, and 5 ml/kg PBS (a negative control). Mice were bled at 2 and 6 hours and circulating cytokine concentrations were measured by BD CBA Th1/Th2 II kit. The number of mice for each group was 2-5 and data are presented as mean±SEM.

Example 6

Enhanced Circulating Cytokine Concentrations After Drug Administration

To ascertain whether a cytokine storm was induced, cytokines (human IFN-γ, IL-2, IL-4, IL-6, IL-10, and TNF) were assayed in the sera of mice after 2 and 6 hours after antibody injection (See, FIGS. 5A-5F). Significant induction of human IFN-γ, IL-6, IL-10, IL-2, IL-4, and TNF upon injection of OKT3 was found in all 10 donors at both 2 and 6 hours.

But with the anti-CD28 mAb administrated mice, only some donors induced significant release of cytokines. Not all donors had a cytokine release response upon anti-CD28 injection.

Figure 5A:
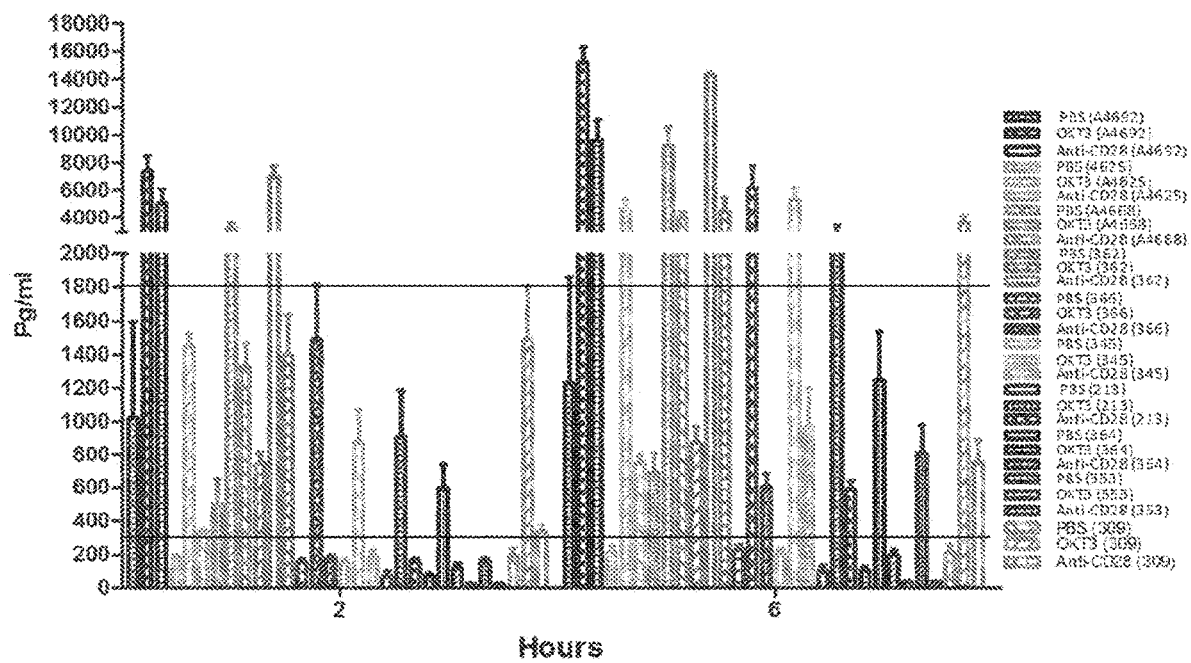
FIGS. 5A-5F depict the induction of cytokines after injection of mAbs into 10 different donors' hPBMC (2×10$^7$ PBMCs/mouse) humanized NSG mice. Mice were i.v. injected with 0.5 mg/kg OKT3 or 1 mg/kg anti-CD28 (ANC28.1/5D10 mAb), or PBS (control). Mice were bled at 2 and 6 hours and circulating cytokine concentrations were measured by BD CBA Th1/Th2 II kit. Cytokine concentrations are shown in FIGS. 5A-5F. The number of mice for each group was 2-5 and data are presented as mean±SEM.

As shown in FIG. 5A, the 10 donors showed different release profiles regarding the IFN-γ cytokine at 6 hours after anti-CD28 injection:
SEVERE/HIGH response: donors A4692, A4668, and 362 (IFN-γ≥1,800 pg/ml),
MEDIUM/MILD response: donors A4625, 366, 345, 309, and 213 (IFN-γ≥300 pg/ml to <1,800 pg/ml), and
LOW/NO response: donors 364 and 353 (IFN-γ<300 pg/ml).

Figure 5B:
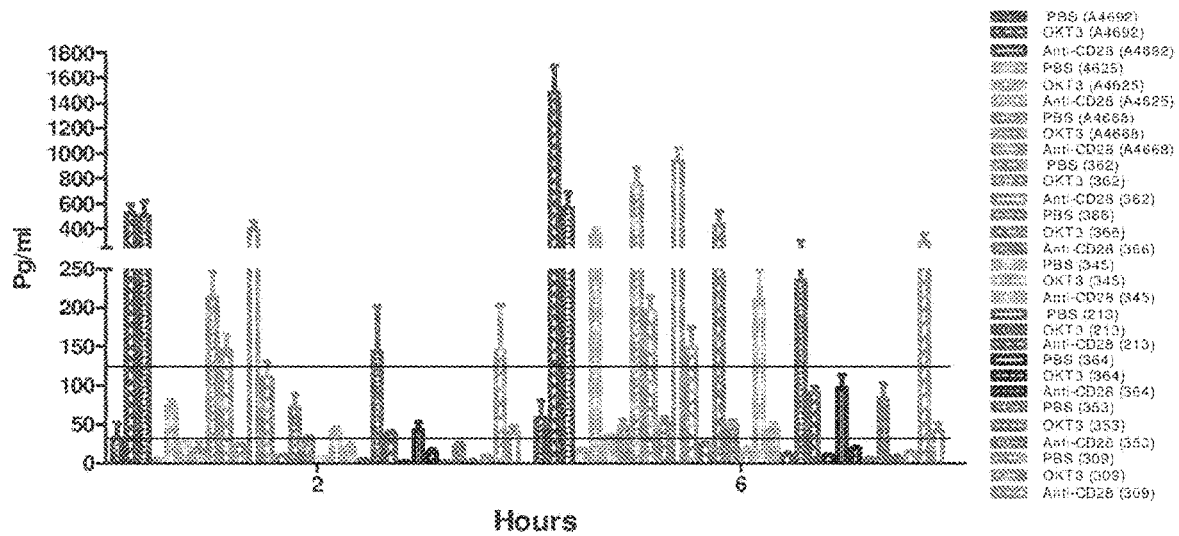

FIG. 5B shows anti-CD28 mAb IL-10 cytokine responses observed at 2 or 6 hours in an NSG mouse who had been engrafted with 2×10$^7$ (PBMCs/mouse). A line is depicted at the IL-10 level of 120 pg/ml, which is the cutoff between severe/high response and low response, so that it is easier to determine if the response is a severe/high response. The responses at 6 hours were as follows:
SEVERE/HIGH response: donors A4692, A4668, and 362 (IL-10≥120 pg/ml),
MEDIUM/MILD response: donors A4625, 366, 345, 213, and 309 (IL-10≥25 pg/ml to <120 pg/ml), and
LOW/NO response: donors 364 and 353 (<25 pg/ml).

We observed that donors whose IFN-γ level is ≥1,800 pg/ml (either by OKT3 or anti-CD28 mAb) also exhibited an increase in IL-10 level (i.e., ≥120 pg/ml). When both \IFN-γ and IL-10 levels are increased above ≥1,800 pg/ml and ≥120 pg/ml, respectively, the donor is very likely to develop CRS if injected with the drug.

FIGS. 5C-5F depict the cytokine releases for IL-6, IL-2, IL-4, and TNF, respectively, at 2 or 6 hours.

Figure 5C:
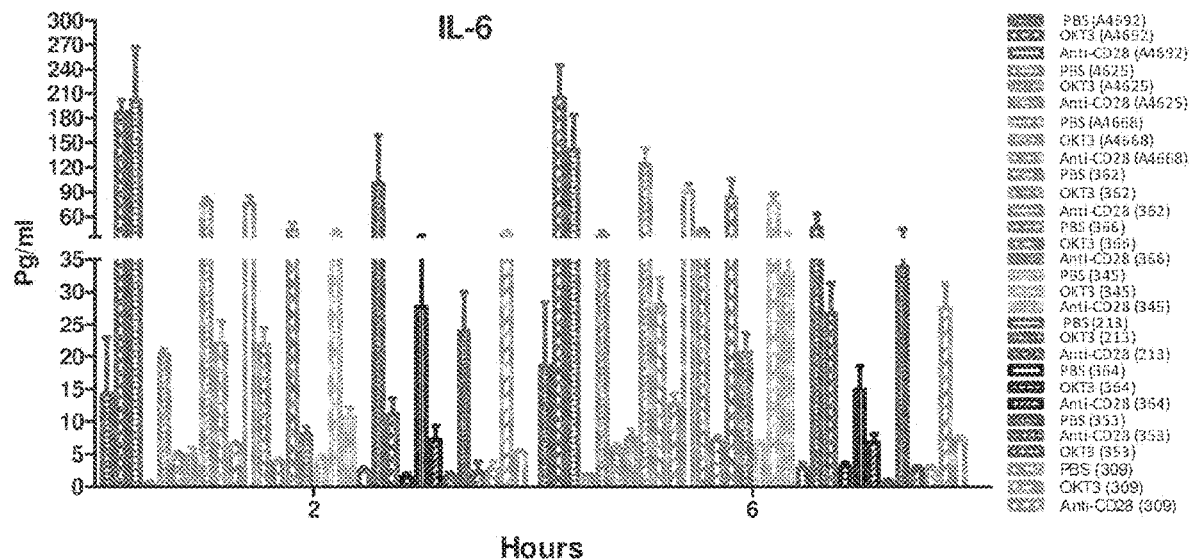

FIG. 5C shows anti-CD28 mAb IL-6 cytokine responses observed at 2 or 6 hours in an NSG mouse who had been engrafted with 2×10$^7$ (PBMCs/mouse). The responses at 6 hours were as follows:
SEVERE/HIGH response: donors A4692, A4668, and 362 (IL-6≥25 pg/m1),
MEDIUM/MILD response: donors A4625, 366, 345, 213, and 309 (IL-6≥10 pg/ml to <25 pg/ml), and
LOW/NO response: donors 364 and 353 (IL-6<10 pg/ml).

Figure 5D:
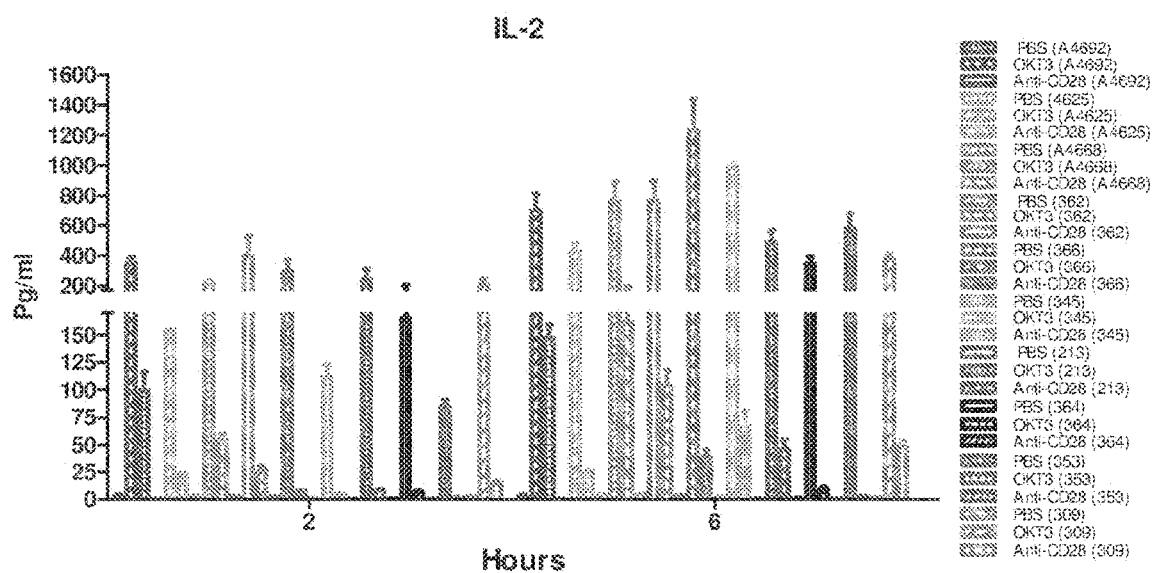

FIG. 5D shows anti-CD28 mAb IL-2 cytokine responses observed at 2 or 6 hours in an NSG mouse who had been engrafted with 2×10$^7$ (PBMCs/mouse). The responses at 6 hours were as follows:
SEVERE/HIGH response: donors A4692, A4668, and 362 (IL-2≥80 pg/ml),
MEDIUM/MILD response: donors A4625, 366, 345, 213, and 309 (15 pg/ml≤IL-2≥80 pg/ml), and
LOW/NO response: donors 364 and 353 (IL-2<15 pg/ml).

Figure 5E:
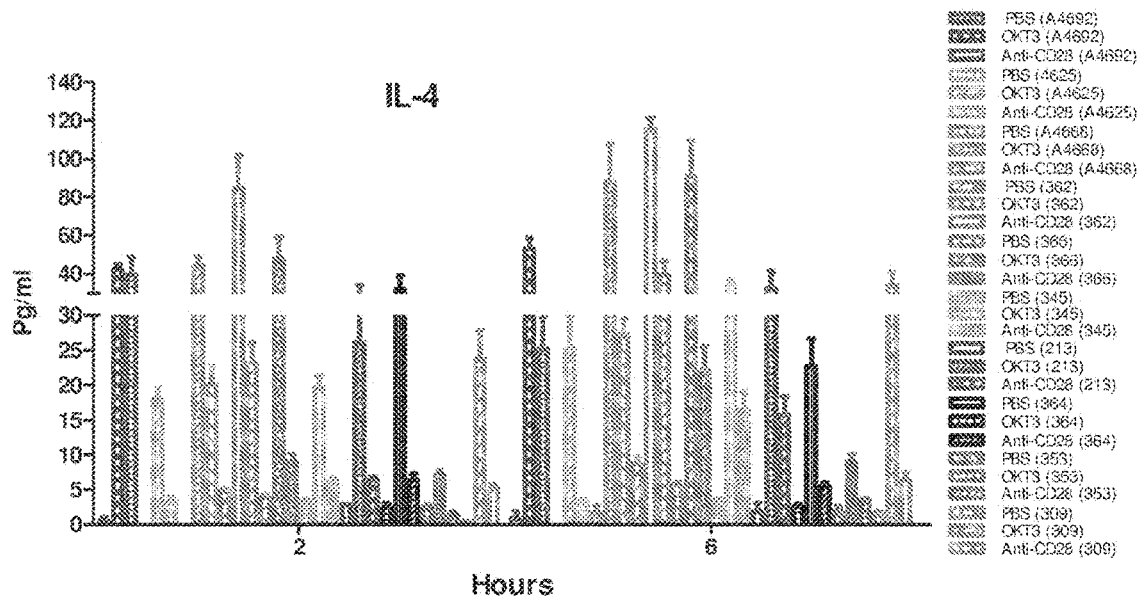

FIG. 5E shows anti-CD28 mAb IL-4 cytokine responses observed at 2 or 6 hours in an NSG mouse who had been engrafted with 2×10$^7$ (PBMCs/mouse). The responses at 6 hours were as follows:
SEVERE/HIGH response: donors A4692, A4668, and 362 (IL-4≥25 pg/ml),
MEDIUM/MILD response: donors A4625, 366, 345, 213, and 309 (10 pg/ml≤IL-4<25 pg/ml), and
LOW/NO response: donors 364 and 353 (IL-4<10 pg/ml).

Figure 5F:
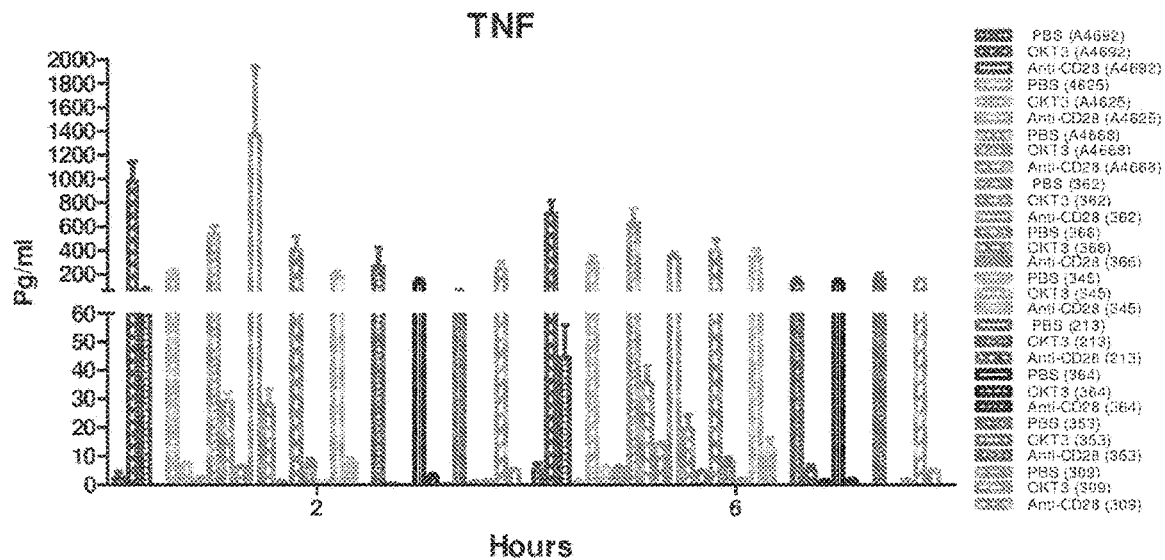

FIG. 5F shows anti-CD28 mAb TNF cytokine responses observed at 2 or 6 hours in an NSG mouse who had been engrafted with 2×10$^7$ (PBMCs/mouse). The responses at 6 hours were as follows:
SEVERE/HIGH response: donors A4692, A4668, and 362 (TNF≥20 pg/ml),
MEDIUM/MILD response: donors A4625, 366, 345, 213, and 309 (5 pg/ml≤TNF<20 pg/ml), and
LOW/NO response: donors 364 and 353 (TNF<5 pg/ml).

FIG. 6 summarizes the response of 10 donors after administration of OKT3 or anti-CD28 in terms of their ability to induce IFN-γ and IL-10. Note that after anti-CD28 mAb administration, donors A4692, A4668 and 362 are severe/high responders; donors A4625, 366, 345, 309 and 213 are medium/mild responders; and donors 364 and 353 are low/no responders. These data clearly show that the NSG/NSG-CSF-1/NSG-IL-6 mouse with PBMC engraftment model is useful to differentiate (or be a predictor of) whether a human is likely to elicit a severe cytokine release syndrome response following administration of an immunomodulatory drug to the human.

As shown in FIGS. 5A-F and FIG. 6, all ten donors'/patients' PBMC engrafted mice showed substantial cytokine release after OKT3 injection. But with administration of anti-CD28 mAb, only a portion of the donors' PBMC engrafted mice showed significant induction of those cytokines. Not every donor had a high level of cytokine release in response to anti-CD28 injection. These results are similar to the variation in human beings. For a CRS-strong-inducer, such as OKT3, every donor had a response, but for a weak inducer, such as anti-CD28, no other methods can detect there is a huge variation between donors, as observed in this method. IFN-γ response can be used as an example: three donors'/patients' PBMCs engrafted mice show high response to the anti-CD28, five donors'/patients' PBMCs engrafted mice show medium response to the anti-CD28, two donors'/patients' PBMC engrafted mice show low/no response to the anti-CD28. The mice also show body temperature drop and increased clinical score when there was cytokine release. The present methods may be used to detect new drug immune toxicity, and also to screen the drug toxicity for an individual patient.

Example 7

Body Temperature Changes in NSG Mice After Immunomodulatory Drug Treatment

Figure 7:
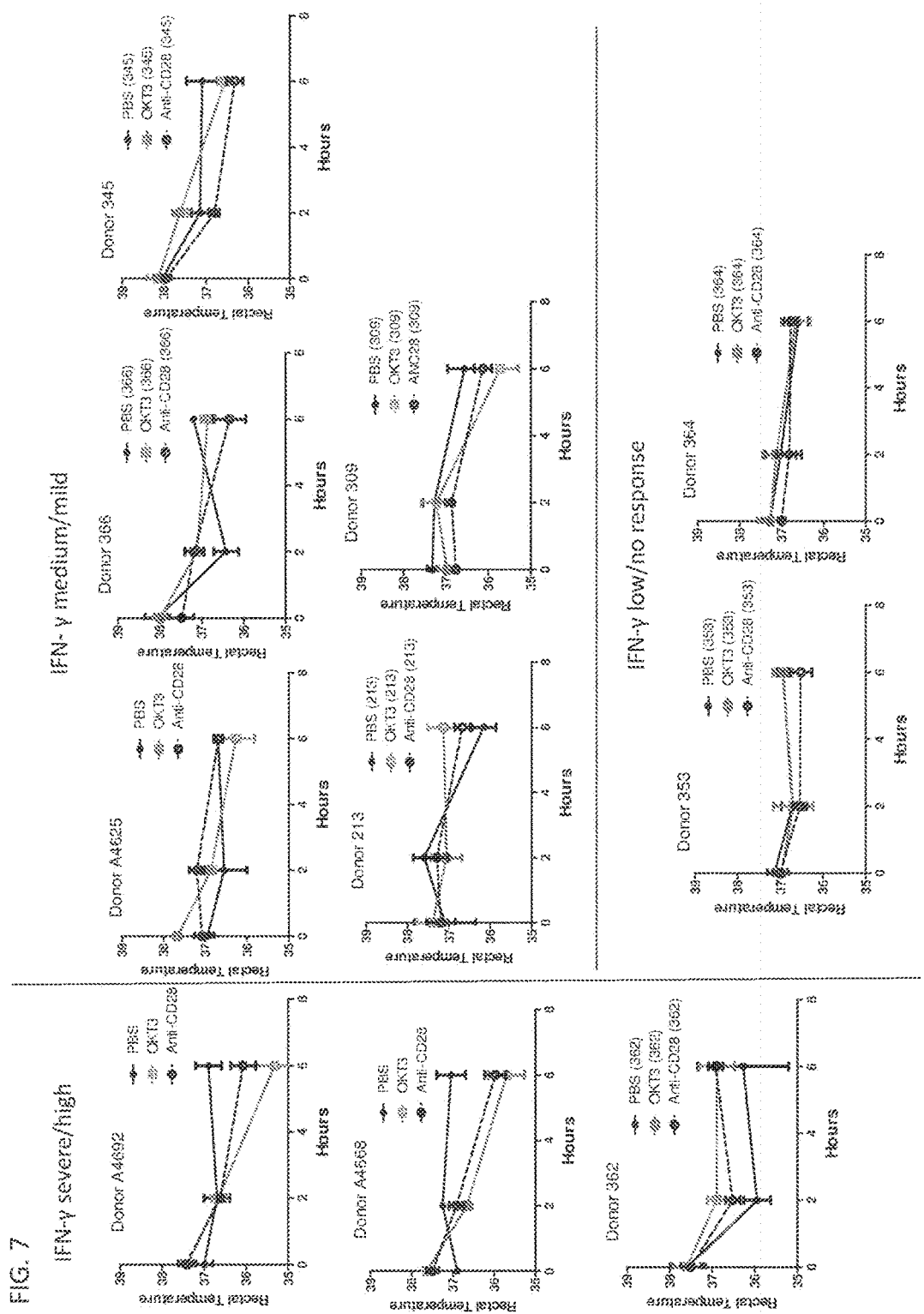
FIG. 7 depicts the changes in rectal temperature in hPMBCs engrafted humanized NSG mice of 10 donors followed by injected with control PBS, OKT3, or anti-CD28 mAb. The number of mice for each group was 2-5 and data are presented as mean±SEM.

Rectal temperature of the mice of Examples 5 and 6 was measured before treatment and again immediately before each time-point bleed. The temperature data are shown in FIG. 7. Humanized NSG mice showed body temperature slightly drop in some animals after drugs treatment. It was noted that body temperature dropped more often in mice that had high IFN-γ release (FIG. 7). For mice in the OKT3 and anti-CD28 groups, body temperature dropped from 37-38° C. to below 36° C. at the 6 hour time point. FIG. 7 shows hypothermia induction after injection of drugs. Rectal temperature was measured in hPMBCs humanized mice of 10 donors injected with control PBS, OKT3, and anti-CD28. The number of mice for each group was 2-5 and data are presented as mean±SEM.

Example 8

Evaluation of the Clinical Score of Mice After Injection of Drugs

The clinical score in the mice was monitored by performing the signs and the grading of scores as follow: Score: 0=normal activity; 1=normal activity, piloerection, tiptoe gait; 2=hunched, reduced activity but still mobile; 3=hypomotile but mobile when prompted; 4=moribund (point of death). Mice with a clinical score of 4 were euthanized. The number of mice for each group was 2-5 and data are presented as mean±SEM.

Figure 8:
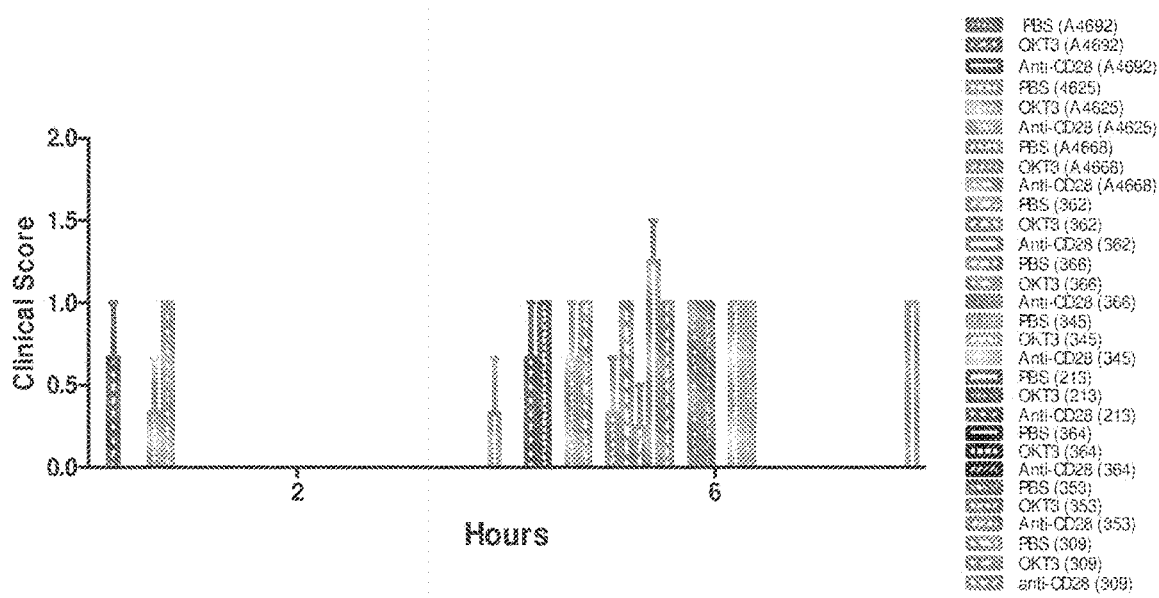
FIG. 8 depicts the clinical score of the 10 donors' humanized mice after injection of the immunomodulatory drugs. At 2 and 6 hours after PBS, OKT3, or anti-CD28 mAb injection, the clinical score of each mouse was evaluated with the following criteria: Score: 0=normal activity; 1=normal activity, piloerection, tiptoe gait; 2=hunched, reduced activity but still mobile; 3=hypomotile but mobile when prompted; 4=moribund (non-responsive to touch). The number of mice for each group was 2-5 and data are presented as mean±SEM.

Most of the mice with cytokine release in the OKT3 or anti-CD28 mAb treated groups were scored 1 at the 6 hour time point. The mice with no or low cytokine release had no clinical score. The clinical score of the mice after injection of drugs is depicted in FIG. 8. Most of the mice had a clinical score of 1.

Example 9

Engraftment of PBMCs (5×10$^7$/mouse) Provides a Humanized Mouse Model for Drug Candidate Toxicity Screening We have developed a humanized mouse model that is useful for toxicity testing to screen potential drugs in discovery. During the early phase of drug candidate development, it is required to screen if a potential drug candidate may possess toxicity activity. In this mouse model, the cytokine response sensitivity was purposely enhanced so as to screen for any toxicity (e.g., cytokine release syndrome) associated with the potential drug candidates.

To do so, a high number of PBMCs (i.e., 5×10$^7$/mouse) was engrafted into the humanized NSG mice. On day 6, the mice received the drug and a cytokine release profile was determined. Here, the IFN-γ and IL-10 levels were evaluated as in the above-mentioned experiments using 2×10$^7$ PBMCs/mouse.

FIGS. 9A and 9B depict donor 213 comparing the 2×10$^7$ vs. 5×10$^7$ PBMC/mouse for IFN-γ or IL-10 level after drug injection. It was observed that the IFN-γ and IL-10 level increased with higher PBMC engraftment upon the administration of OKT3 and anti-CD28 mAbs on day 6 using the same amounts of the mAbs (i.e., OKT3 mAb =0.5 mg/kg and anti-CD28 mAb=1 mg/kg). This enhanced cytokine release with 5×10$^7$ PMBC/mouse is believed to be suitable for a screening assay in pre-clinical drug development. FIGS. 9C-9F depict a comparison of cytokine response (IL-6, IL-2, IL-4, and TNF, respectively) in donor 213 with 2×10$^7$ PBMCs/mouse and 5×10$^7$ PBMCs/mouse. These data indicate that for drug toxicity screening, a high number of PBMCs provides a reliable and sensitive method for testing.

Example 10

Comparison of Cytokine Release with Varying PBMC Engraftment Concentrations

In this experiment, we compared cytokine release using humanized mice that were engrafted with one of three concentrations of PBMCs to determine the effect of cell concentration. In particular, we compared the cytokine levels generated in humanized NSG mice, engrafted with 2×10$^7$ PBMCs/mouse, 3×10$^7$ PBMCs/mouse, or 4×10$^7$PBMCs/mouse, after treatment in such mice with an immunotherapeutic drug (i.e., mAbs OKT3, anti-CD28 or KEYTRUDA® (pembrolizumab).

Figure 10A:
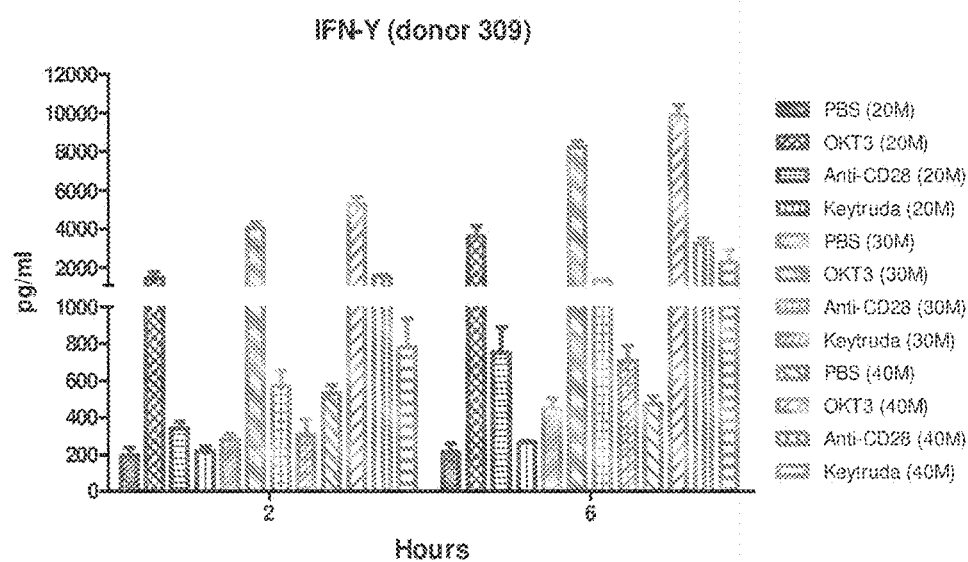
FIGS. 10A-10F depict the induction of cytokines after injection of antibodies in different human PBMCs concentration ($2\times10^7$, $3\times10^7$ and $4\times10^7$ per mouse from donor 309) humanized NSG mice. Mice were iv injected with 0.5 mg/kg OKT3, 1 mg/kg anti-CD28, 10 mg/kg KEYTRUDA® (pembrolizumab), or PBS as control. Mice were bled at 2 and 6 hours and circulating cytokine concentrations were measured by BD CBA Th1/Th2 II kit. The number of mice for each group was 3-5 and data are presented as mean±SEM.
Figure 10B:
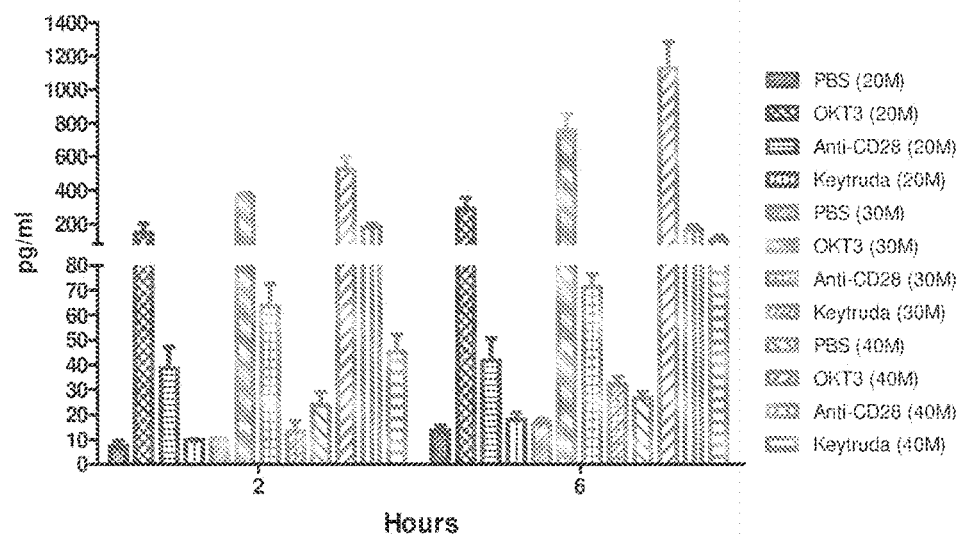
Figure 10C:
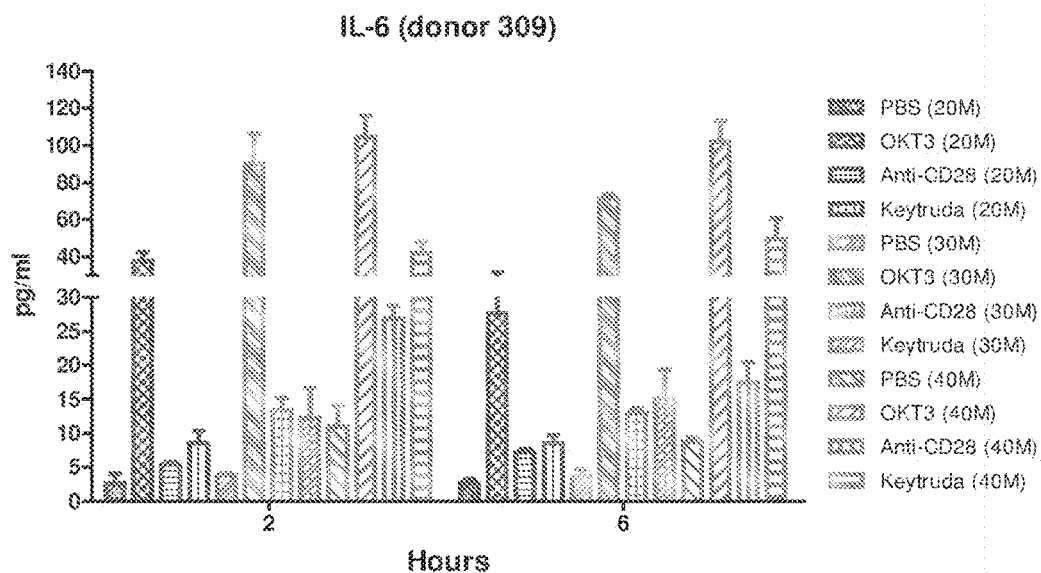
Figure 10D:
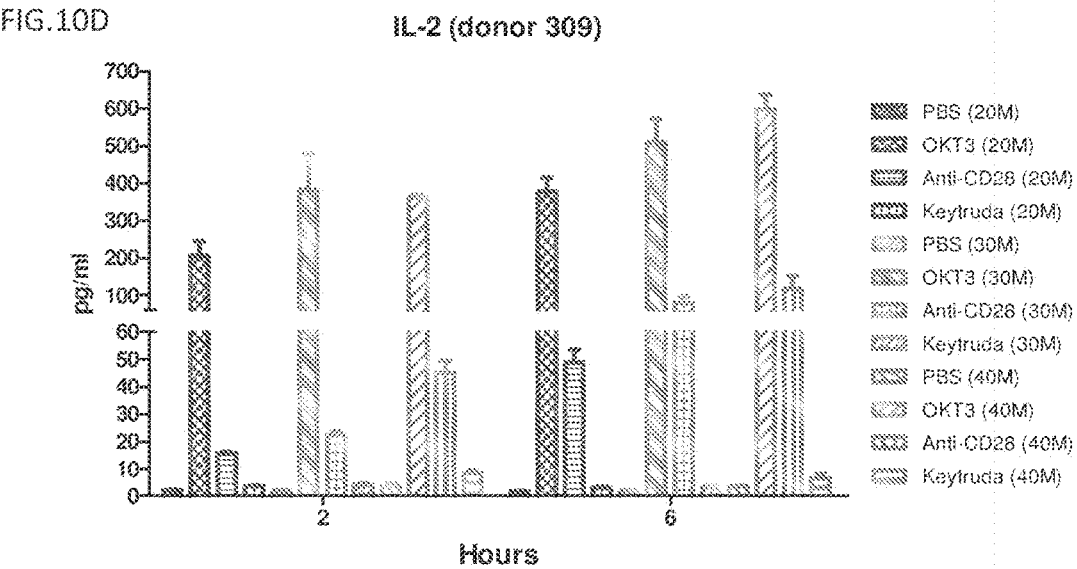
Figure 10E:
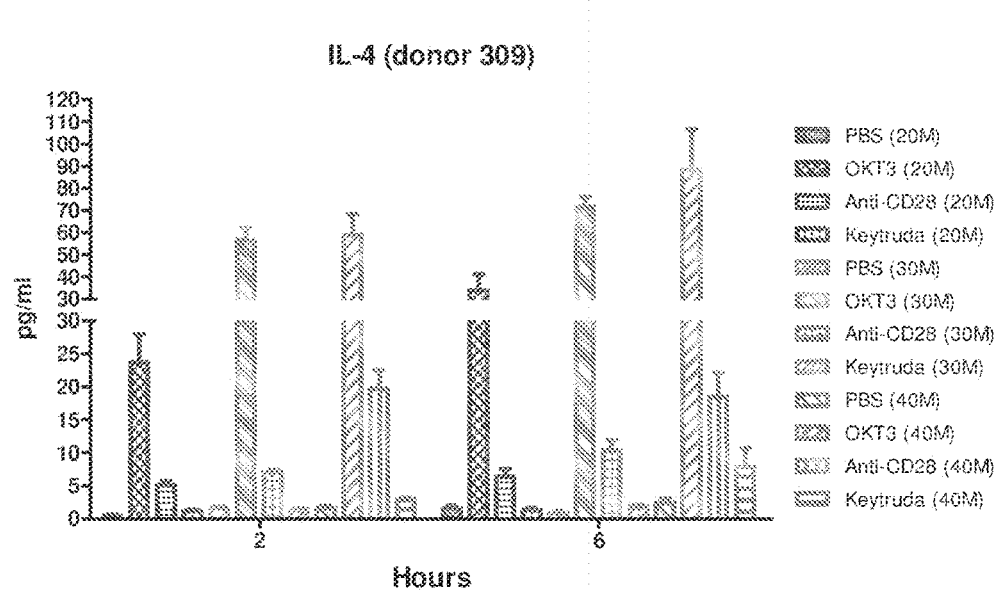
Figure 10F:
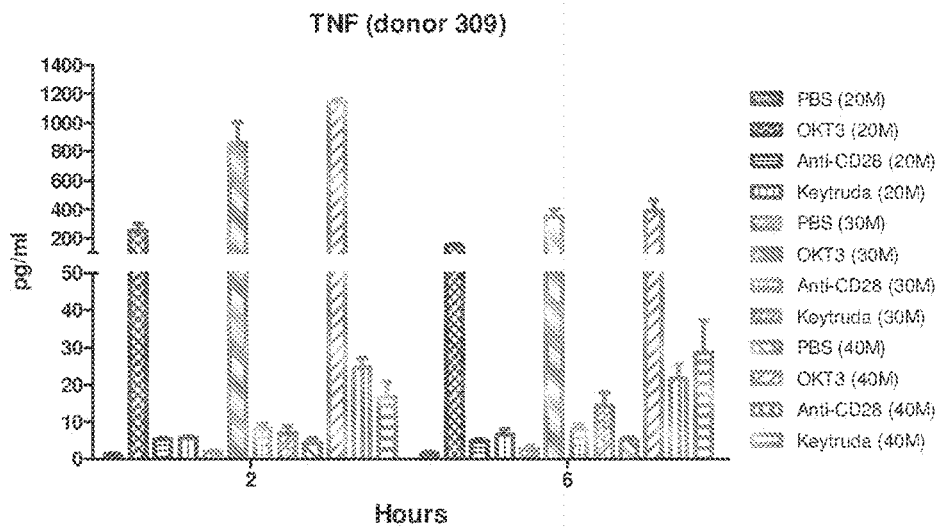
Figure 12A:
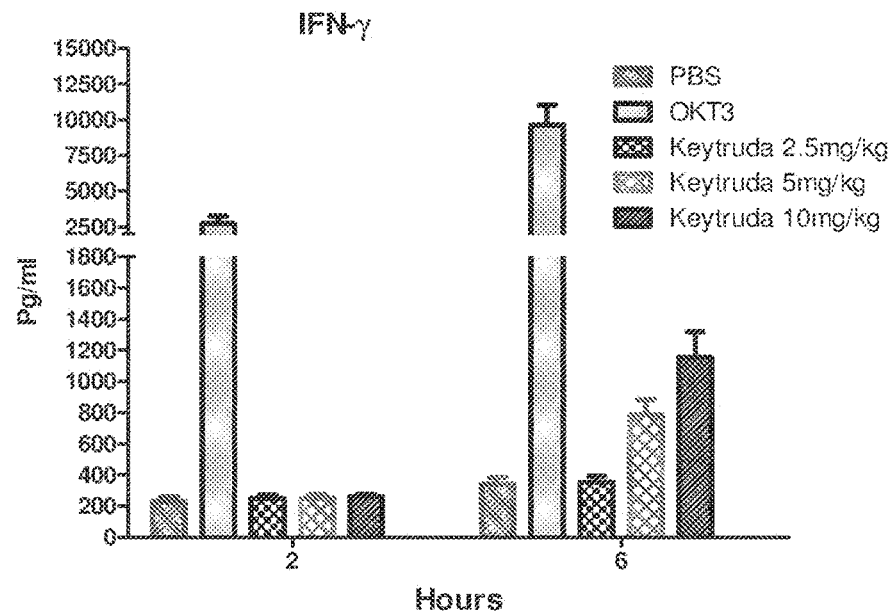
Figure 12B:
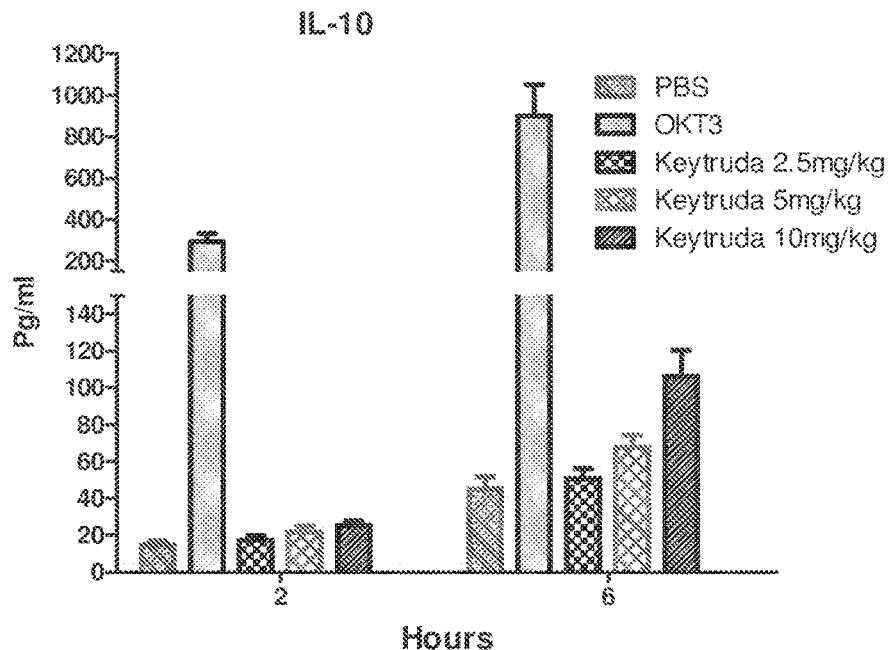
Figure 12C:
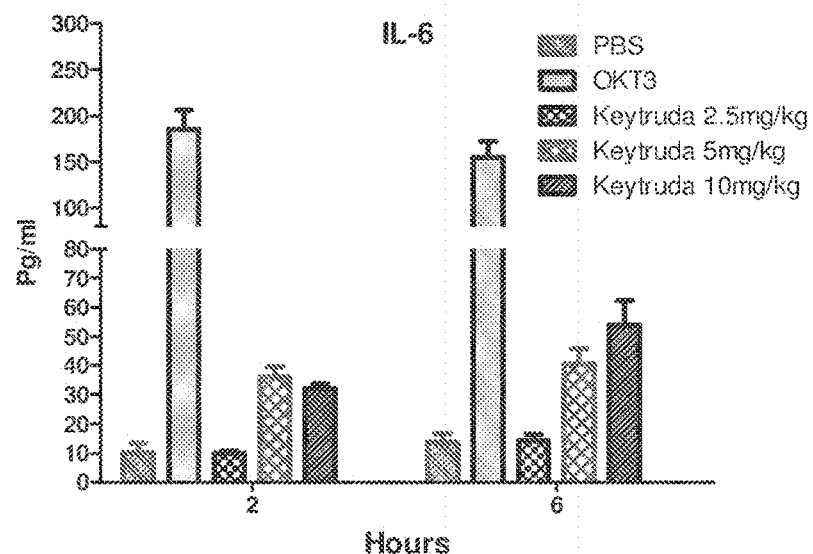
Figure 12D:
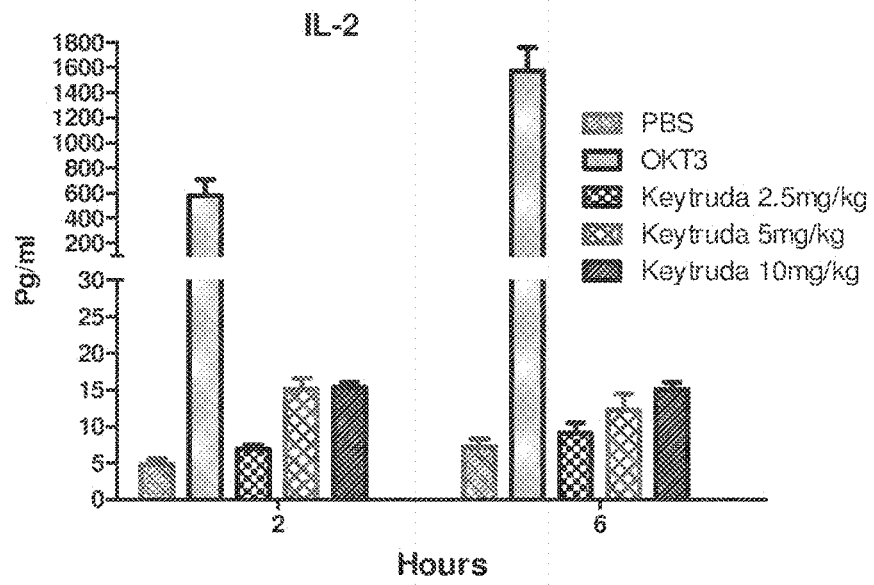
Figure 12C:
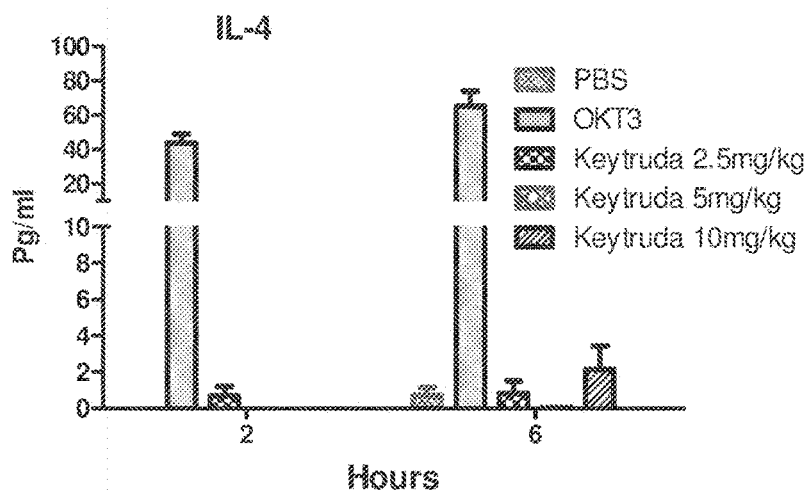
Figure 12F:
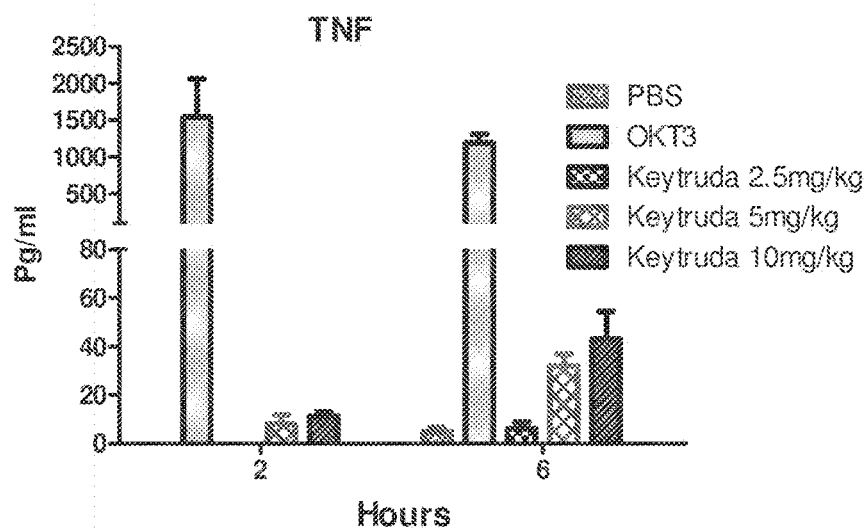

On day 6 after engraftment, the mice received the immunotherapeutic drug (mAb) and a cytokine release profile was determined in these three groups of mice. Mice were bled at 2 and 6 hours and circulating cytokine concentrations were measured by BD CBA Th1/Th2 II kit. FIGS. 10A-F depict the cytokine levels after drug injection in donor 309 humanized NSG mice engrafted with 2×10$^7$, 3×10$^7$, or 4×10$^7$PBMCs/mouse. FIG. 10A depicts the INFγ level for each group of mice. FIG. 10B depicts the IL-10 level for each group of mice. FIG. 10C depicts the IL-6 level for each group of mice. FIG. 10D depicts the IL-2 level for each group of mice. FIG. 10E depicts the IL-4 level for each group of mice. FIG. 10F depicts the TNF level for each group of mice.

We observed that, under these experimental conditions, the cytokine levels exhibited similar increases upon the administration of OKT3 and anti-CD28 mAbs and KEYTRUDA® (pembrolizumab) on day 6 using the same amounts of the mAbs (i.e., OKT3 mAb=0.5 mg/kg, anti-CD28 mAb=1 mg/kg and KEYTRUDA®=10 mg/kg) in the two mouse groups at the lower engraftment levels, 2×10$^7$ or 3×10$^7$ PBMCs per mouse. However, with engraftment at 4×10$^7$PBMCs per mouse, under these experimental conditions, cytokine response to each of the drug injections were found to be too high to differentiate individual response with optimal sensitivity. In contrast, engraftment of PBMCs at 2×10$^7$ and 3×10$^7$ cells per mouse under these conditions provides a sensitive test for screening for occurrence of cytokine storm in response to a drug in individual humans.

Example 11

Body Temperature and Clinical Score in Different Concentration of PBMCs Engraftment In this study, we measured the different cell types, body temperature, and clinical score in the humanized mice after engraftment with different PBMC concentrations. PBMCs used in this study were obtained from donor 309. FIG. 11A depicts the cell population on day 5 after PBMC engraftment. The total human CD45+ cells percentage increased with increasing level of PBMC engraftment in the mice, although the percentages of different cell types within the CD45 population were similar. FIG. 11B depicts the clinical score in the humanized mice after administration with OKT3 mAb (0.5 mg/kg), anti-CD28 (1 mg/kg) and KEYTRUDA® (pembrolizumab; 10 mg/kg). FIGS. 11C, 11D, and 11E depict mouse body temperature change. As shown in FIGS. 11C and 11D, there was a slight body temperature drop in the 3×10$^7$ PBMCs/mouse group, as compared to that in the 2×10$^7$ PBMCs/mouse group.

Example 12

Cytokine Levels Increase with Increased Drug Dosage

Drug tolerance is often different from person to person. The humanized immunodeficient mouse model can be used to test drug concentration dependence of cytokine release in individual patients.

In this study, the inventors examined different concentrations of KEYTRUDA® (pembrolizumab) to determine if there is dosage dependence in the CRS in humanized mice. 6-week old female NOD.Cg-Prkdc$^{scid}$Il2rg$^{tm1wjl}$/SzJ (NSG, JAX stock number 005557) mice were irradiated with 100cGy X-ray at least 4 hours prior to human PBMCs engraftment. The PBMCs in these experiments were from donor 358. Purified/isolated human PBMCs were intravenously injected into the mice at 3×10$^7$ cells/mouse. Six days after PBMC engraftment, mice were iv injected with PBS (negative control), 0.5 mg/kg OKT3 (positive control), 2.5 mg/kg, 5 mg/kg, or 10 mg/kg KEYTRUDA®. There were 5 mice per group. These KEYTRUDA® dosages are in the range of dosages studied in clinical trials discussed on the U.S. prescribing information for KEYTRUDA®. Few adverse effect reports of severe cytokine release syndrome after KEYTRUDA® administration have been documented.

Mice were bled at 2 and 6 hours and circulating cytokine concentrations were measured using a BD CBA Th1/Th2 II kit. As shown in FIGS. 12A-F, the level measured after injection of the positive control OKT3 was very high for each of IFN-γ, IL-10, IL-6, IL-2, IL-4, and TNF. As shown in FIGS. 12A-F, cytokine levels increased along with the increasing dosage of KEYTRUDA®. At 2.5 mg/kg KEYTRUDA®, the cytokine levels were similar to the negative control group (i.e., PBS control group) and there was almost no cytokine release. In contrast, the cytokine levels increased with increasing KEYTRUDA® dosages, with a high cytokine response when 10 mg/kg KEYTRUDA® was used.

As can be seen in FIGS. 12A to 12F, cytokine levels six hours after dosing showed a dose-dependent response on amount of KEYTRUDA® (pembrolizumab), increasing with increasing dose. At a KEYTRUDA® concentration of 2.5 mg/kg, the level of each cytokine was within the error range of the level measured for the PBS control group, indicating there was almost no cytokine release. At 10 mg/kg KEYTRUDA®, the level of each cytokine was in the medium range for predicting CRS. Thus for donor 358, administration of 2.5 mg/kg KEYTRUDA® would have a lower risk of producing CRS than administration of 10 mg/kg KEYTRUDA® (pembrolizumab).

The dose-dependence of the cytokine release shows that the in vivo humanized mouse model may be used to screen for the best drug concentration, with respect to avoiding immune toxicity, for an individual patient. Such information can then be used in conjunction with other knowledge about the dosing range effective for treatment of the disorder afflicting the patient to determine an effective, but safe dose of the drug.

Example 13

Body Temperature and Clinical Score for Different Doses of KEYTRUDA® (Pembrolizumab)

Figure 13A:
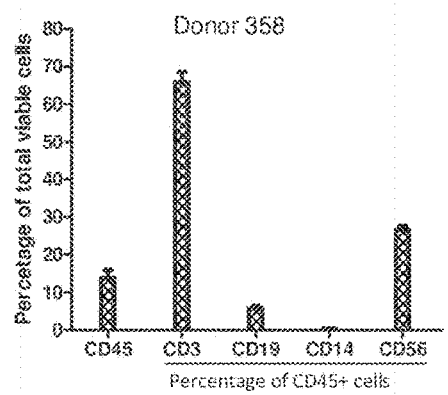
FIGS. 13A-13C depict the body temperature and clinical score changes in response to KEYTRUDA® (pembrolizumab) in donor 358 PBMC humanized mice.
Figure 13B:
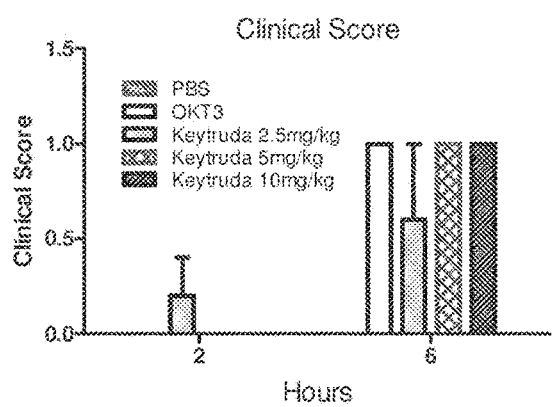
Figure 13C:
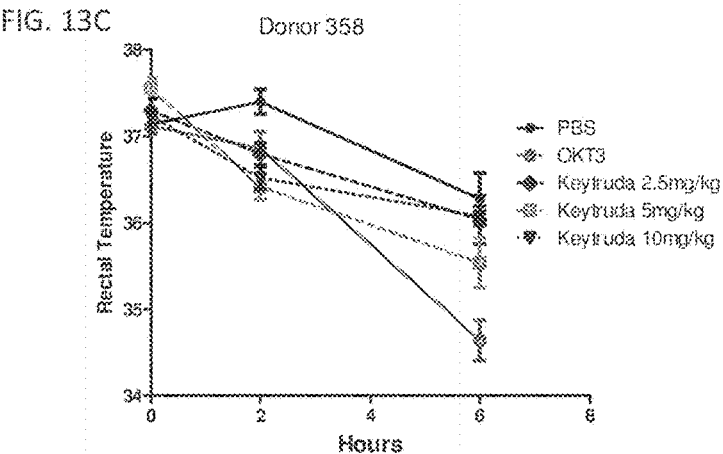

In this study, the inventors measured the various cell types, body temperature, and clinical score in the humanized mice described in Example 12. FIG. 13A depicts the cell population on day 5 after cells engraftment. The inventors observed that T-cells and NK cells represent the predominant cells types in these mice. FIG. 13B depicts the clinical score after administration of the immunotherapeutic drug (KEYTRUDA® (pembrolizumab)) with different doses of KEYTRUDA®. The clinical score 6 hours after dosing was the same as positive control (OKT administration) when dosed with 5 mg/kg and 10 mg/kg KEYTRUDA®. FIG. 13C depicts mouse body temperature changes with different doses of KEYTRUDA®.

Example 14

Comparison—In Vivo Humanized Mouse Method Versus In Vitro Assay

In vitro whole-blood or PBMC assays are currently the main assays for testing cytokines release for drug screening. In this example, cytokine release in response to a drug treatment was determined by two methods for the same PBMC donor, an in vitro PBMC assay and the in vivo humanized mouse method.

In Vivo Method

Day 0: 6-week old female NOD.Cg-Prkdc$^{scid}$I12rg$^{tm1wjl}$/SzJ (NSG, JAX stock number 005557) mice were irradiated with 100 cGy X-ray at least 4 hours prior to human PBMC engraftment. Purified/isolated human PBMCs were intravenously injected to the mice at 3×10$^7$ cells/mouse. PBMCs were from donor 213, 309, 345, or 366. Day 5, bled the mice for human cells engraftment testing. Day 6, administer drug to mouse; determine cytokine levels in mouse serum 6 hours after administering the drug using a BD CBA Th1/Th2 II kit. In these experiments, 5 mice were used per group.

In Vitro Method

Day-1: Coated the plate with drugs: dilute drug (e.g., an antibody) in PBS; leave plate open under hood.

Day 0: Process PBMCs from each donor. PBMCs were from donor 213, 309, 345, or 366. Thaw PBMCs in supplemented RPMI and wash once. Count cells and re-suspend in supplemented RPMI at 1×10$^6$ cells/ml. Wash coated wells twice with 200 µl PBS and then once with 200 µL supplemented RPMI. Plate 100 µl of cells in each well (for a total of 1×10$^5$ cells per well).

Day 2: Harvest supernatant from each well and measure the cytokine level using a BD CBA Th1/Th2 II kit.

Results

Figure 14A:
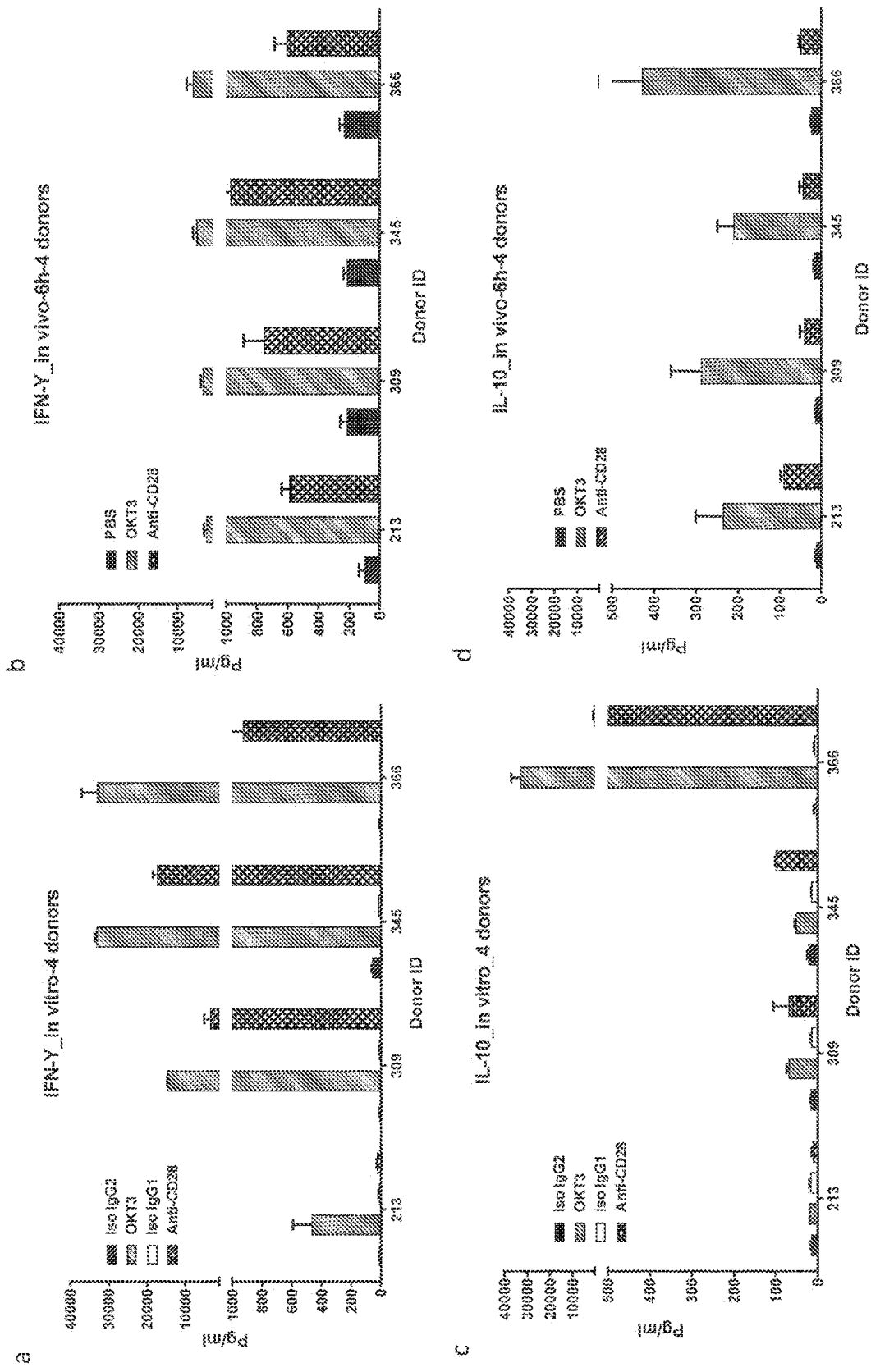
FIGS. 14A-B depicts the different results of in vitro and in vivo measurement of cytokine release after drug exposure.
Figure 14B:
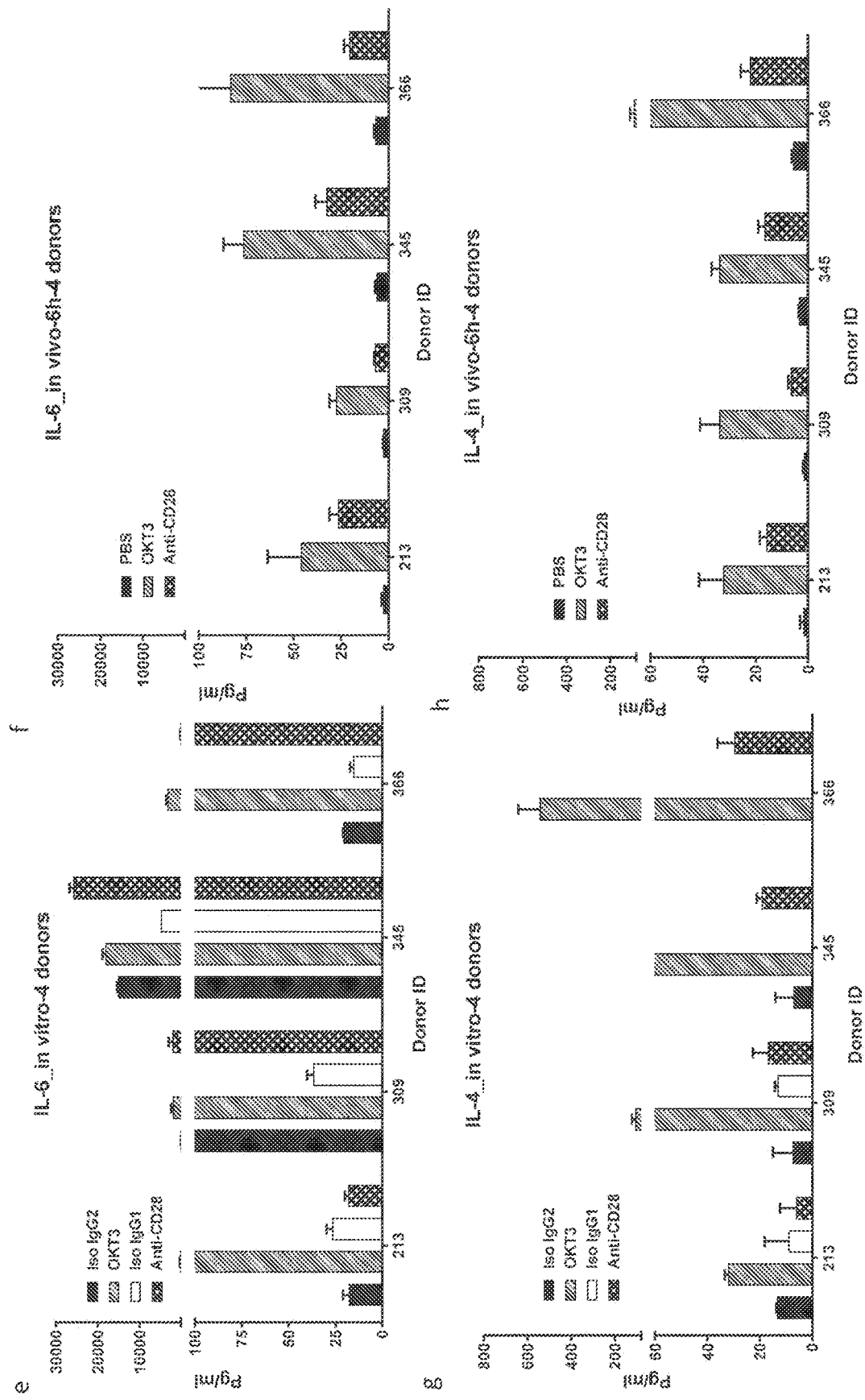

The two methods for determining cytokine release levels after a drug treatment were compared for treatment of PBMCs from four different donors with an anti-CD28 antibody (Ancell, Cat. No. 177-824). For the in vitro assay, anti-CD28 was dosed at 10 µg/well in the 96 well plates. For the in vivo method, anti-CD28 was dosed at 1 mg/kg. Supernatants of the in vitro PBMC culture wells and serum from the mice were collected and cytokine levels were measured. Antibody OKT3 (0.5 mg/kg for the in vivo assay or 1 mg/ml for the in vitro assay) was used as a positive control and either PBS or isotype antibodies were used as negative controls in the in vivo assay or the in vitro assay, respectively. The cytokine levels determined are presented in FIGS. 14A (IFN-γ and IL-10) and 14B (IL-6 and IL-4) as mean values ±standard error of the mean (SEM). FIGS. 14A and 14B show that for each of the four PBMC donors, for any given cytokine, different levels were determined by the two assays.

Figure 15:
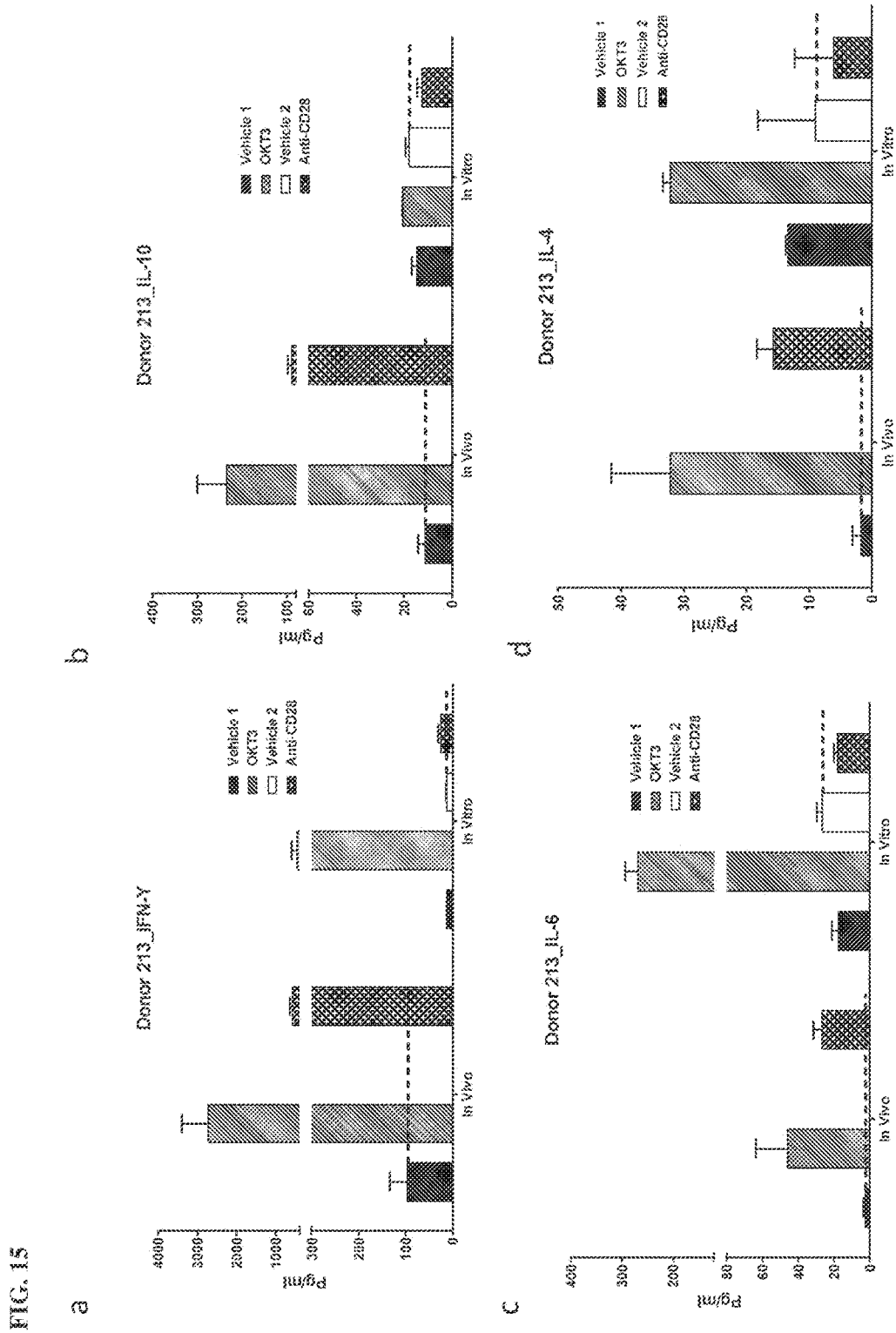
FIG. 15 presents histograms of cytokine release levels in response to anti-CD28 treatment obtained by in vitro or in vivo experiments with PBMC donor 213 for a) IFN-γ; b) IL-10; c) IL-6; and d); IL-4. Data are presented as mean±SEM. The dotted line in each graph is the control level for the anti-CD28 experiment.

FIG. 15 replots the FIG. 14A and FIG. 14B cytokine level data of donor 213 to permit easier comparison of the differences in cytokine levels determined in the two tests. For each of the four cytokines, IFN-γ, IL-10, IL-6, and IL-4, the in vitro test showed relatively little cytokine release was produced in donor 213 cells after dosing with anti-CD-28. In the in vitro assay, measured cytokine levels after dosing with ant-CD28 were little different from those determined after dosing with the control isotype antibody ("vehicle 2") for anti-CD28, while cytokine levels after dosing with the control OKT3 antibody were much higher than levels determined after dosing with the control isotype antibody for OKT3 ("vehicle 1"). In contrast, by the in vivo testing method, for each of the four cytokines, IFN-γ, IL-10, IL-6, and IL-4, the cytokine level produced in donor 213 cells after dosing with either anti-CD-28 or OKT3 was much higher than the level measured in the negative control.

These results show that for some humans the in vitro test may fail to show that they will react with a cytokine storm upon dosing with an immunoactive drug, although the in vivo test shows that those individuals may react with a cytokine storm upon dosing with the immunoactive drug. The in vivo humanized mouse method is more sensitive than the in vitro assay and can predict the potential for a cytokine storm in a human which the in vitro test may miss.

Example 15

Cytokine Release After Treatment With Drug Combinations

The PBMC humanized mouse model can effectively test whether single drugs can induce a cytokine storm in an individual. However, for drug screening and clinical therapy, sometimes drug combinations must be used. This example shows that the PBMC humanized mouse model can be used to test drug combinations for cytokine release. The results obtained with the model are shown to be donor specific.

6-week old female NOD.Cg-Prkdc$^{scid}$Il2rg$^{tm1wjl}$/SzJ (NSG, JAX stock number 005557) mice were irradiated with 100cGy X-ray at least 4 hours prior to engraftment with human PBMCs. Isolated human PBMCs from respective donors were intravenously injected to the mice at $3\times10^7$ cells/mouse. PBMCs were from donor 213 or donor 364. Day 6 after PBMC engraftment, we administered a combination of drugs to mice and determined cytokine levels in mouse serum 6 hours after administering the drugs using a BD CBA Th1/Th2 II kit. Five mice were used in every experimental group.

Drug combinations tested were: KEYTRUDA® (pembrolizumab) and REVLIMID® (lenalidomide); KEYTRUDA® and anti-thymocyte globulin (ATG) (THYMOGLOBULIN® (rabbit)); and anti-CD28 and ATG.

Pembrolizumab (KEYTRUDA®) is a humanized antibody used in cancer immunotherapy. Lenalidomide (REVLIMID®) is a derivative of thalidomide which is an oral immunomodulatory small molecule drug used in cancer treatment. Anti-thymocyte globulin (ATG), marketed as THYMOGLOBULIN® (rabbit), is an immunosuppressant used to reduce the body's natural immunity in patients who receive transplants, such as kidney transplants.

In the KEYTRUDA® (pembrolizumab) and REVLIMID® (lenalidomide) experiments, the humanized NSG mice were intravenously (iv) injected with 5 mg/kg KEYTRUDA®, per orally administered 100 mg/kg lenalidomide, or received both drugs. Treatment with iv 5 ml/kg PBS was used as the control.

In the KEYTRUDA® (pembrolizumab) and ATG experiments, the humanized NSG mice were intravenously injected with 5 mg/kg KEYTRUDA®, 1 mg/kg ATG, or received both drugs. Treatment with iv 5 ml/kg PBS was used as the control.

In the anti-CD28 and ATG experiments, the humanized NSG mice were intravenously injected with 1 mg/kg anti-CD28, 1 mg/kg ATG, or received both drugs. Treatment with iv 5 ml/kg PBS was used as the negative control.

Figure 16:
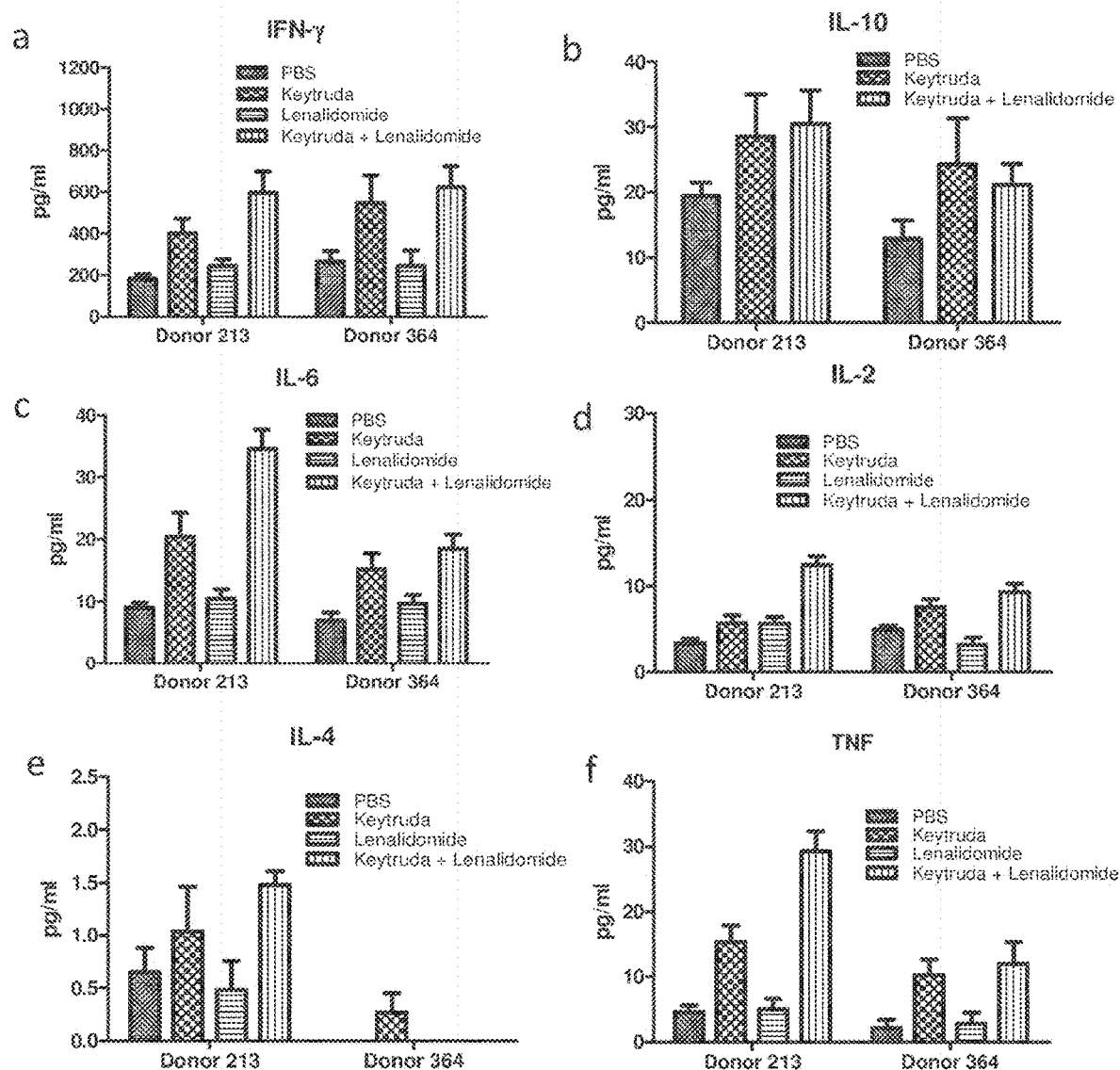
FIG. 16 presents histograms of cytokine release levels in response to treatment with KEYTRUDA® (pembrolizumab), REVLIMID® (lenalidomide), or both drugs for PBMC donor 213 or donor 364 for a) IFN-γ; b) IL-6; c) IL-4 d) IL-10; e) IL-2; and f) TNF. Treatment with PBS was the control. Data are presented as mean±SEM.

The cytokine levels determined in the KEYTRUDA® (pembrolizumab) and REVLIMID® (lenalidomide) experiments are shown in FIG. 16 for both donors. Cytokines for which levels were measured were IFN-γ(panel a); IL-10 (panel b); IL-6 (panel c); IL-2 (panel d); IL-4 (panel e); and TNF (panel f).

Based on data from two halted clinical trials evaluating KEYTRUDA® (pembrolizumab) in combination with dexamethasone and the immunomodulatory agent REVLIMID® (lenalidomide) for treating multiple myeloma, the FDA issued a statement in 2017 that treatment with the combination of KEYTRUDA and lenalidomide resulted in an increased risk of severe toxicity and death.

As shown in FIG. 16, IFN-γ, IL-6, IL-2 and TNF each showed a significant increase in cytokine release when KEYTRUDA® (pembrolizumab) and REVLIMID® (lenalidomide) were used in combination over the level produced by treatment with each drug alone for donor 213, but not for donor 364.

Figure 17:
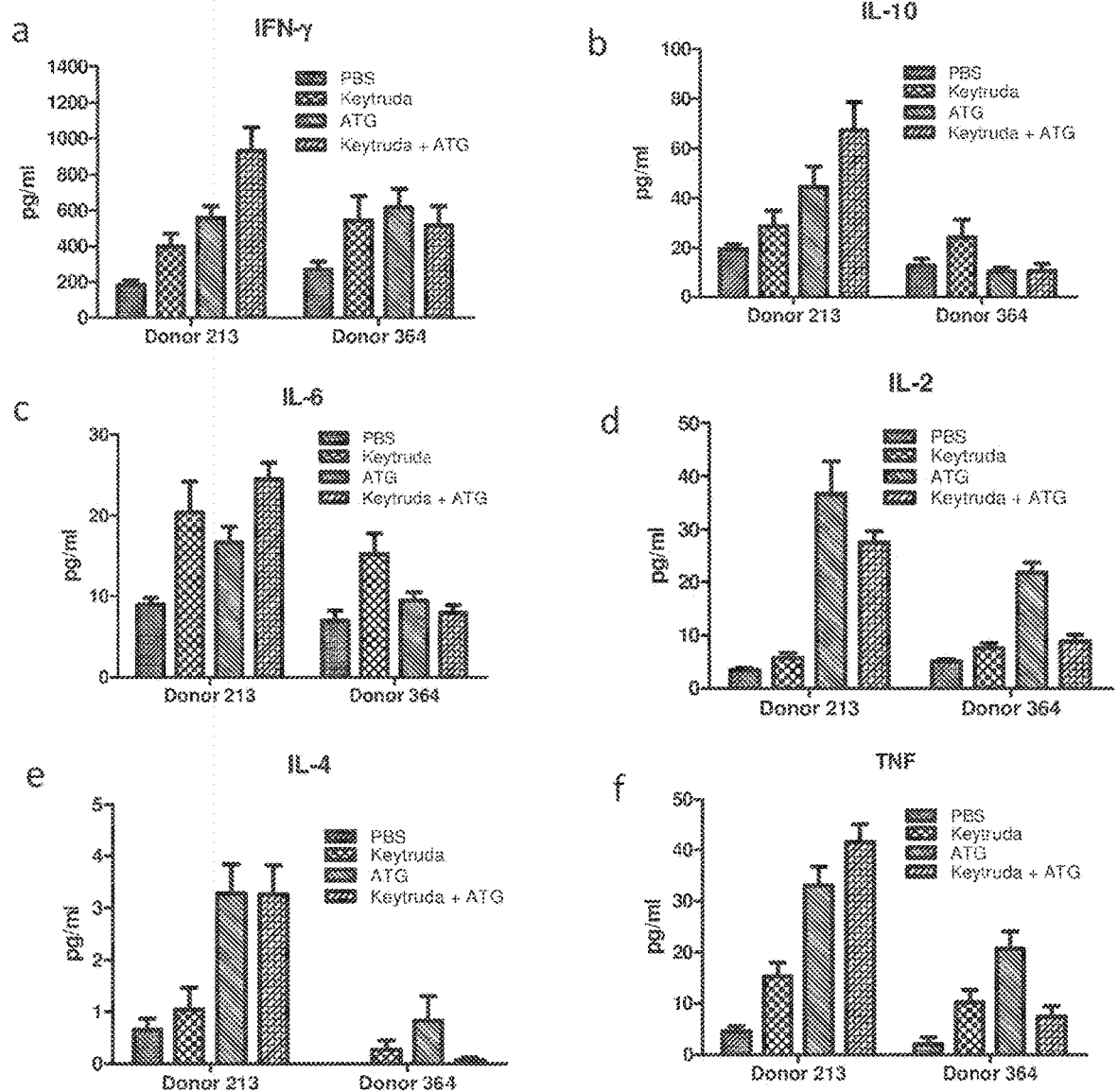
FIG. 17 presents histograms of cytokine release levels in response to treatment with KEYTRUDA® (pembrolizumab), ATG, or both drugs for PBMC donor 213 or donor 364 for a) IFN-γ; b) IL-10; c) IL-6 d) IL-2; e) IL-4; and f) TNF. Treatment with PBS was the control. Data are presented as mean±SEM.

Anti-thymocyte globulin (ATG) is used in the prevention and treatment of acute rejection in organ transplantation and therapy of aplastic anemia. ATG has been previously demonstrated to stimulate clinical toxicity. FIG. 17 shows the cytokine results after treatment with KEYTRUDA® (pembrolizumab) alone, ATG alone, and the combination of KEYTRUDA® and ATG. The levels of IFN-γ, IL-6, IL-10 and TNF were higher after treatment with the combination of KEYTRUDA® and ATG than after treatment with either drug alone for donor 213, but not for donor 364.

Figure 18:
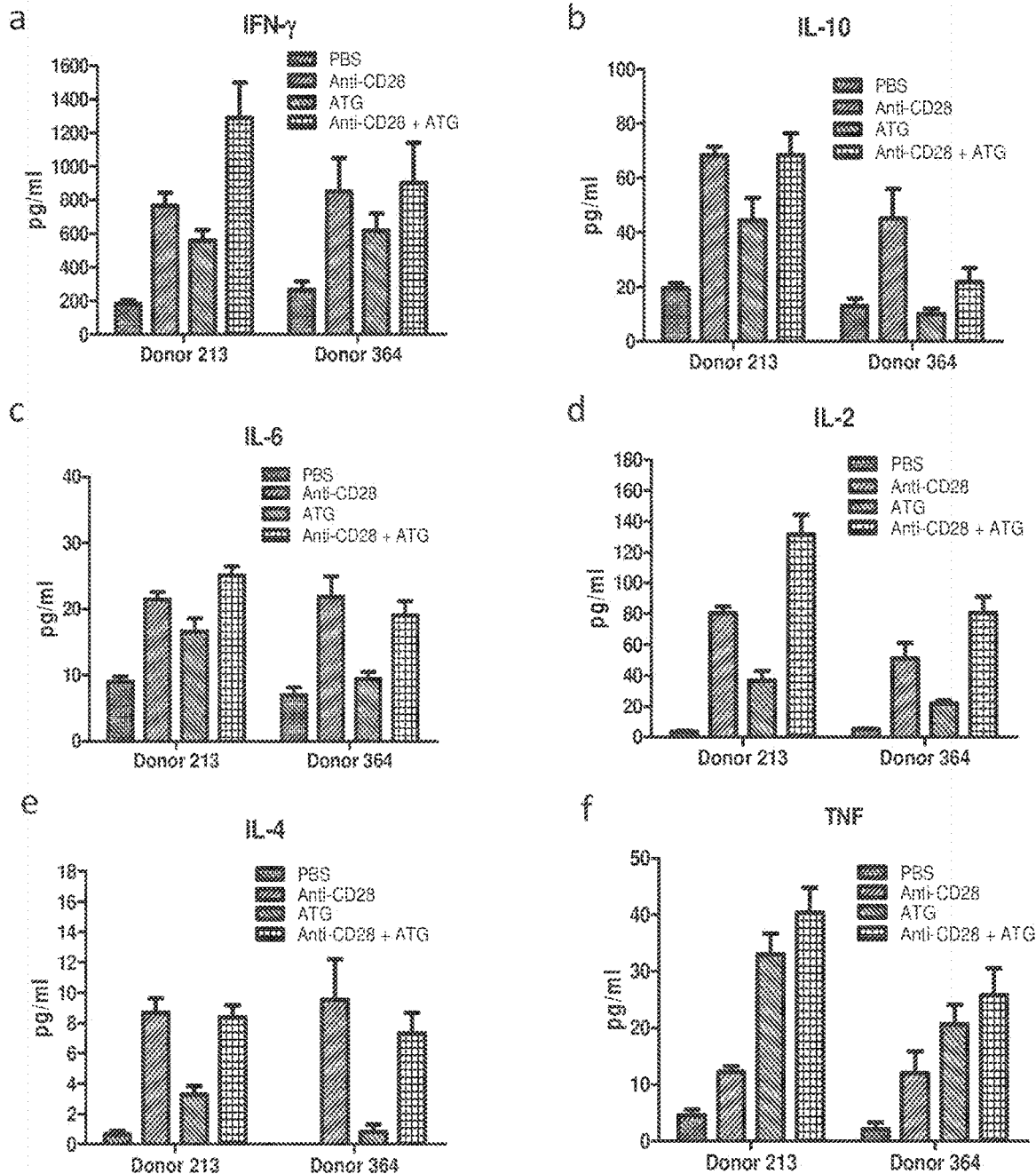
FIG. 18 presents histograms of cytokine release levels in response to treatment with anti-CD-28, ATG, or both drugs for PBMC donor 213 or donor 364 for a) IFN-γ; b) IL-6; c) IL-4 d) IL-2; e) IL-4; and f) TNF. Treatment with PBS was the control. Data are presented as mean±SEM.

FIG. 18 shows the cytokine results after treatment with anti-CD28 alone, ATG alone, and the combination of anti-CD28 and ATG. The levels of IIFN-γ, IL-6, IL-2 and TNF were higher after treatment with the combination of drugs compared to after treatment with either drug alone for donor 213, but only IL-2 and TNF increased after treatment with the combination of drugs compared to after treatment with either drug alone for donor 364.

These results indicate that the in vivo humanized mouse model can predict likelihood of high cytokine release by a single drug, and also for drug combinations. In addition, different PBMC donors showed different cytokine release responses to the combination therapies.

This study demonstrates the advantage of using a patient's own PBMCs in an in vivo method to screen, prior to clinical administration, if a specific combination of drugs to a patient can likely induce severe cytokine release. Similarly, the present method is useful to screen possible drug-related toxicity associated with administration of a drug combination.

Example 16

Human Immune Cell Population and Cell-Type Distribution in Irradiated Humanized Mice In this example, we evaluated the human immune cell population and cell type distribution in irradiated humanized mice. The effects of X-ray irradiation before human PBMC engraftment into immunodeficient mice and the time after engraftment on the human cell population in the mice are demonstrated.

Six-week old female NOD.Cg-Prkdc$^{scid}$Il2rg$^{tm1wjl}$/SzJ (NSG, JAX stock number 005557) mice were used for engraftment with human PBMCs. For the mice subjected to the irradiation treatment, mice were irradiated with 100cGy X-ray at least 4 hours prior to engraftment with human PBMCs. Purified/isolated human PBMCs from the donor were intravenously injected to the mice at $2\times10^7$ cells/mouse. PBMCs were from one of six different donors: 362, 345, 2785, 213, 364, or 3251. Mice were bled at day 5 and day 10 after engraftment and human cells in the mouse blood were analyzed by flow cytometry to determine human cell types present and percentages of each type. Specifically, the mouse PBMCs in mixture with the human PBMCs were stained with human antibodies: anti-CD45, anti-CD3, anti-CD14, anti-CD19, and anti-CD56 mAbs. The results are shown in FIG. 19, which illustrates that the human cell population is different between the mice with and without irradiation on day 5 and day 10.

Figure 19:
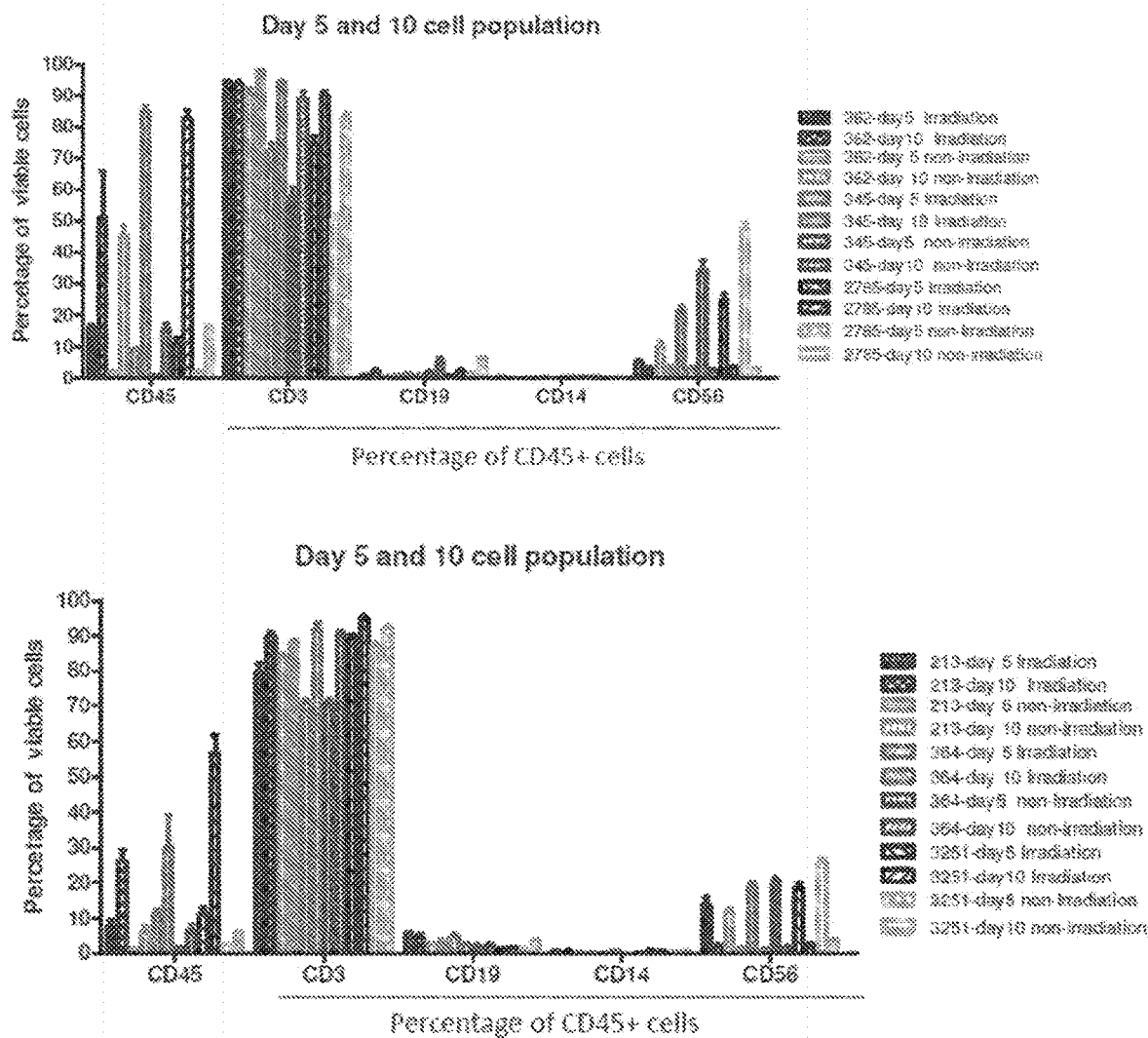
FIG. 19 illustrates the day 5 and day 10 cell populations in whole blood of humanized mice with or without irradiation prior to engraftment with human PBMCs; mice were humanized with PBMCs from one of six different donors: 362, 345, and 2785 (upper graph) and 213, 364, and 3251 (lower graph).

As shown in FIG. 19, on day 5, the total human leukocyte cell population (CD45+) was about 8-15% in the irradiated mice, but only 1-3% in non-irradiated mice, with variation between donors as to the total population. FIG. 19 further shows that on day 5, the distribution of leukocyte cell types within the total human cell (CD45+) population for irradiated or non-irradiated mice was almost identical, with the pre-dominant cell types in each being CD3+ cells (T cells) and CD56+(NK cells), with small percentages of CD19+ cells (B-cells) and CD14+ cells (monocytes).

FIG. 19 shows that on day 10, the total human cell (CD45+) population has grown to about 30-85% of viable cells in the irradiated mice, but to only 8-17% of viable cells in the non-irradiated mice, with variation between individual donors.

FIG. 19 further shows that on day 10, the distribution of leukocyte cell types within the total human cell (CD45+) population was again similar for irradiated or non-irradiated mice. In either irradiated or non-irradiated mice, the pre-dominant cell type was CD3+ cells (T cells), which grew and expanded their population in the mice. Only small or negligible percentages surviving of CD56+(NK cells), CD19+ cells (B-cells) and CD14+ cells (monocytes) were present in the irradiated or non-irradiated mice—i.e., these cells did not grow and expanded their populations in the mice.

Because the absolute number of human cells present on day 5 or day 10 in the irradiated mice was about 3 to 15 times higher than the absolute number of human cells present on the same day in the non-irradiated mice, the irradiated mice exhibited higher numbers of each of the types of human leukocytes present. Importantly, on day 5 the irradiated mice had higher absolute numbers of surviving CD56+ (NK cells), CD19+ cells (B-cells) and CD14+ cells (monocytes) within the human CD45+ cell population, providing a superior modeling of the human immune system that enhances sensitivity and accuracy of testing for cytokine release syndrome.

Example 17

Figure 20:
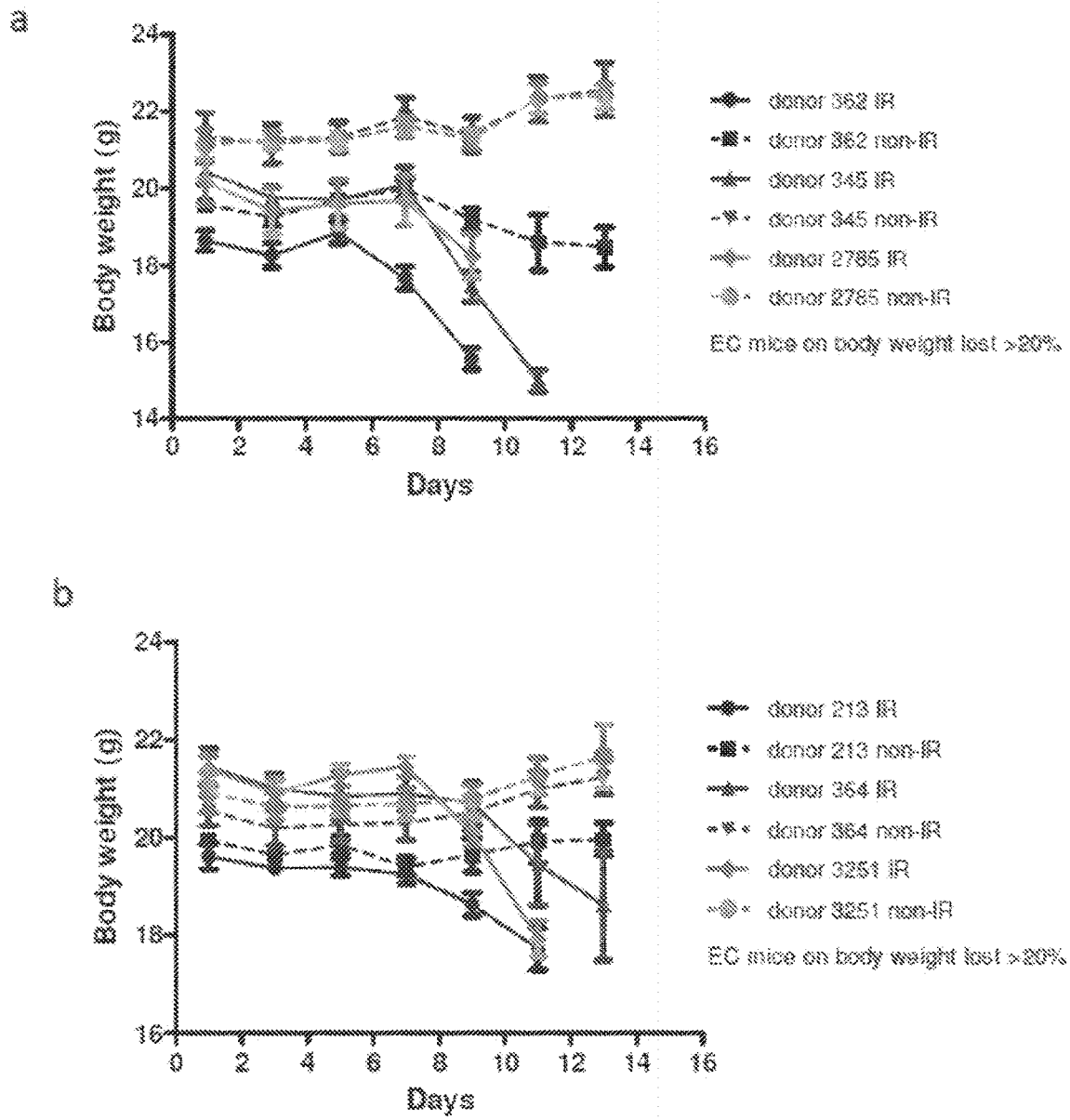
FIG. 20 shows the body weight lost as a function of days after PBMC engraftment for mice humanized with PBMCs from one of six different donors: 362, 345, and 2785 (panel a) and 213, 364, and 3251 (panel b) after irradiation (IR) and without irradiation (non-IR).

Body Weight Loss as Indicator of GVHD in Irradiated or Non-Irradiated Humanized Mice In this study, we used body weight loss as an indicator of GVHD in humanized mice. Body weight measurements were made daily on humanized mice engrafted with 20 million PBMCs from each of six different human donors (362, 345, 2785, 213, 364, or 3251). Mice were either irradiated or not irradiated prior to engraftment with donor PBMCs, in accordance with the procedures in Example 16. The body weight measurements for the irradiated and non-irradiated groups for each donor are shown in FIG. 20, panel a (donors 362, 345, and 2785); panel b (donors 213, 364, and 3251). FIG. 20 shows that for all donors, body weight loss occurs earlier for the irradiated mice than for the non-irradiated mice, demonstrating that GVHD develops faster for the irradiated humanized mice than for the non-irradiated humanized mice. For all six human donors, body weight loss for the irradiated humanized mice after day 8 is significant (at least about 10%), indicating significant GVHD after day 8. The non-irradiated mice did not show significant body weight loss even at 12-14 days after PBMC engraftment, indicating much slower onset of significant GVHD.

Example 18

GVHD Causes Human Cytokine Release in Humanized Mice Alone (In The Absence of Drug Treatment)

This example demonstrates that mice experiencing significant GVHD secreted human cytokines as a result of GVHD. GVHD developed faster for the irradiated humanized mice than for the non-irradiated humanized mice.

Figure 21:
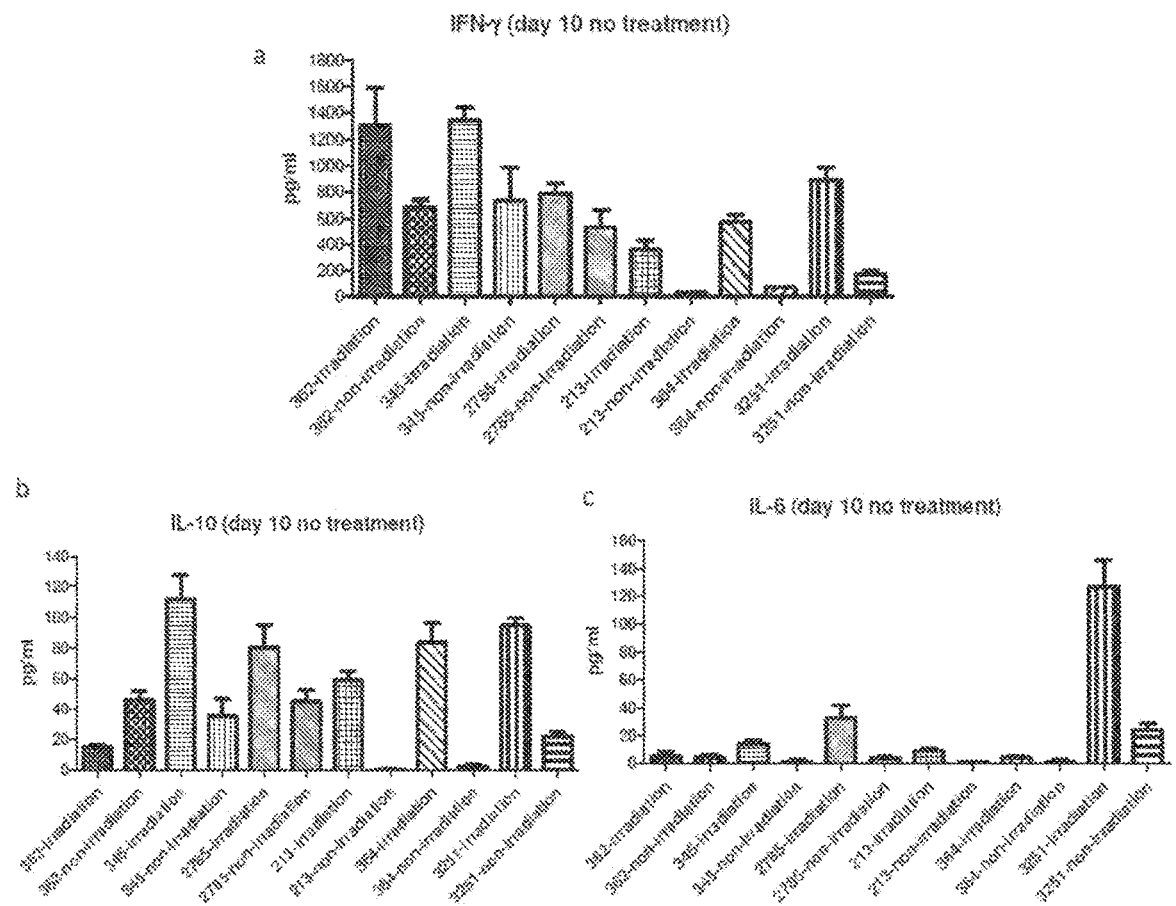
FIG. 21 shows cytokine level in PBMC humanized mice without any drug treatment on day 10 after engraftment with PBMCs.

FIG. 21 shows human cytokine levels present in humanized mice on day 10 after PBMC engraftment in the absence of any drug treatment. Cytokine measurements are shown for IFN-γ(panel a), IL-10 (panel b) and IL-6 (panel c) for humanized mice of the six donors (362, 345, 2785, 213, 364, and 3251), with or without irradiation prior to PBMC engraftment. For each donor, on day 10 after engraftment, more of each of the three cytokines was present in the blood of the irradiated mice than in the non-irradiated mice. At day 10, based on the body weight measurements disclosed in Example 17, the irradiated mice had more severe GVHD, with consequent GVHD-associated secretion of human cytokines from the human leukocytes present, than do the non-irradiated mice.

Example 19

Cytokine Release in Irradiated and Non-Irradiated Humanized Mice

This example evaluates the effect of X-ray irradiation (prior to PBMC engraftment) of mice on drug-induced human cytokine release.

Figure 22A:
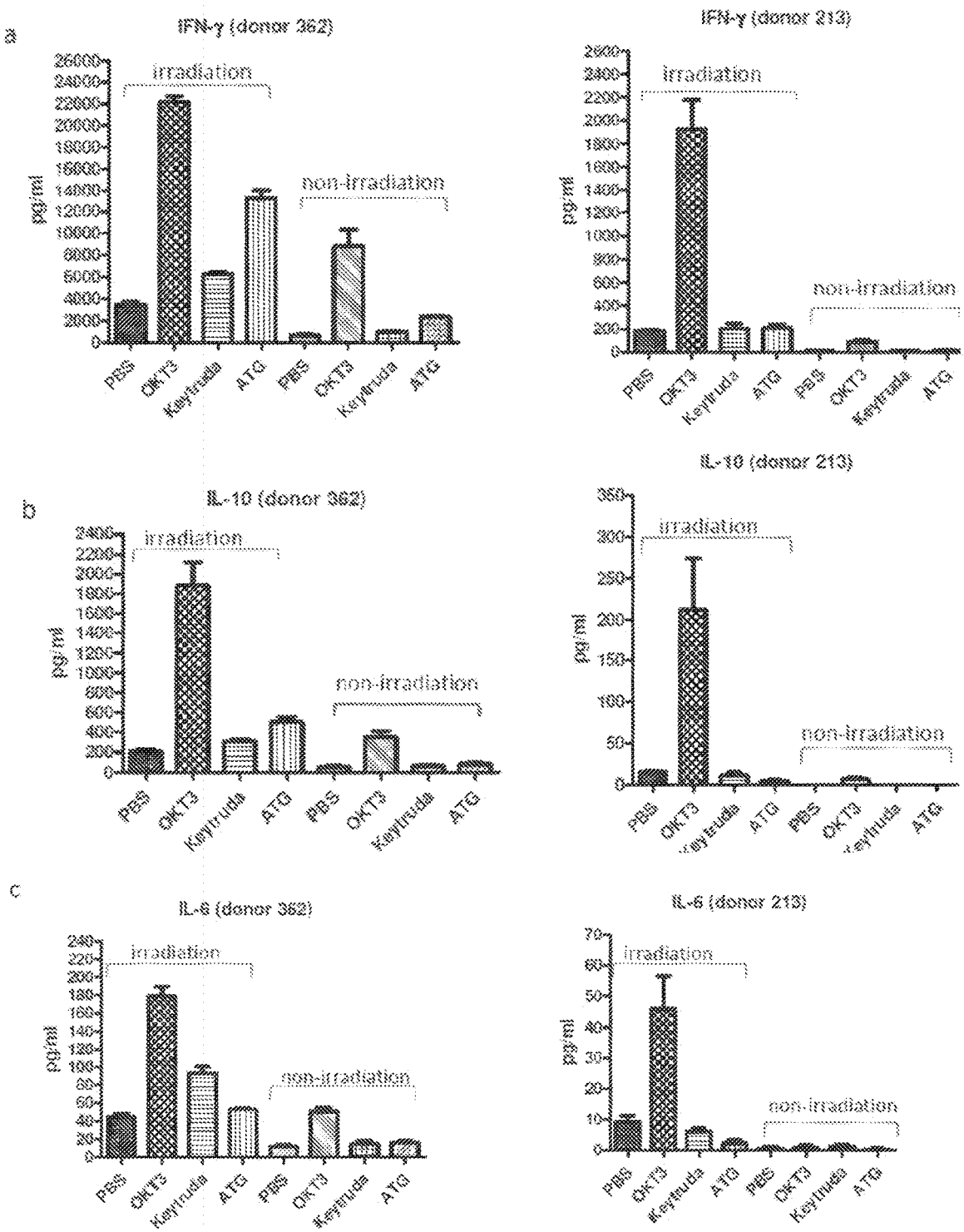
FIGS. 22A-22B presents graphs of level of cytokines released after drug treatment (by irradiated or non-irradiated mice humanized with PBMCs of either donor 362 or 213. Drugs (OKT3, KEYTRUDA, or ATG) or the negative control (PBS) were administered on day 6 after PBMC engraftment.
Figure 22B:
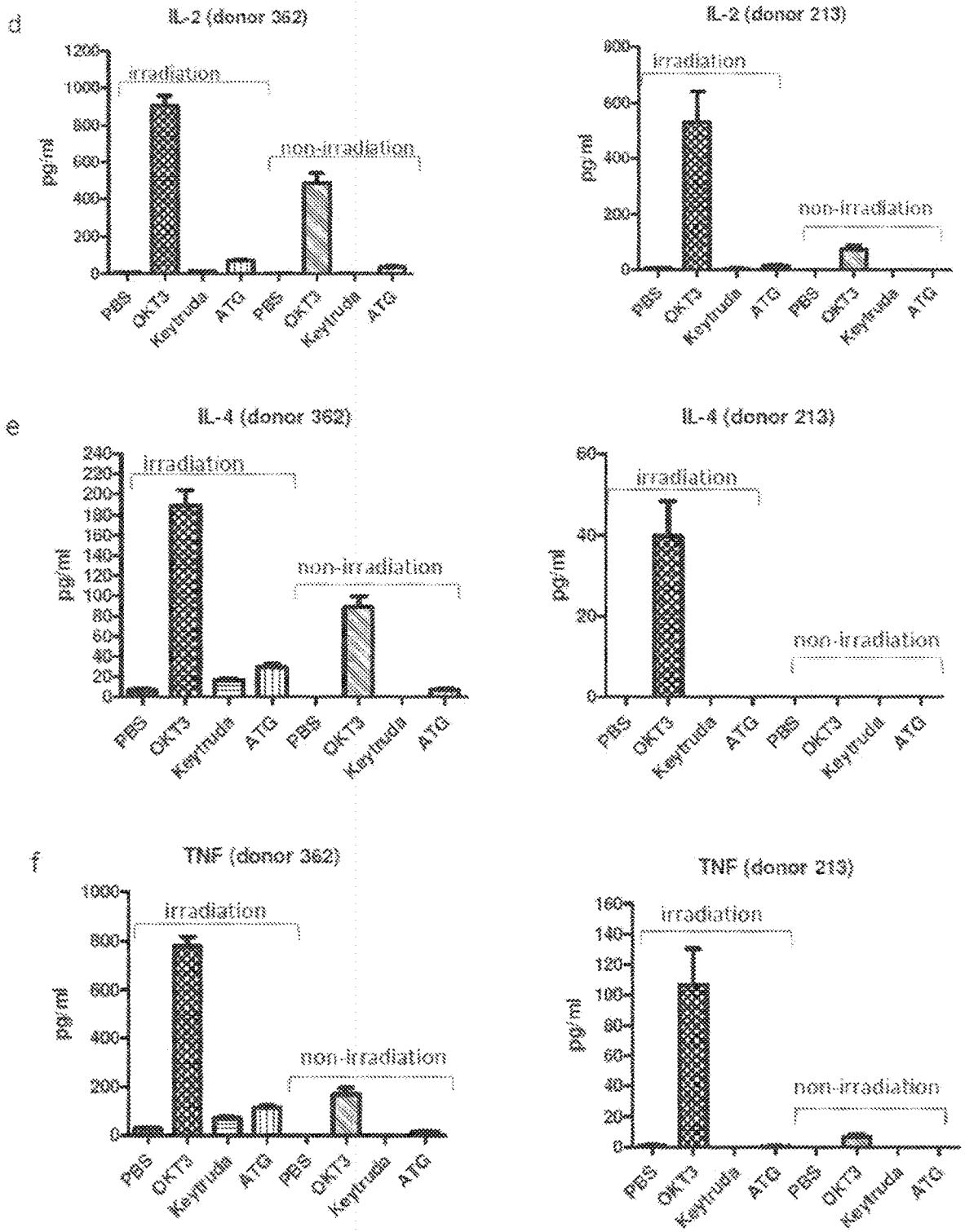

Mice were engrafted with 20 million PBMCs from donor 362 (a high responder), or donor 21 (a medium responder). Mice were either irradiated or not irradiated prior to engraftment with donor hPBMCs. Six days after engraftment, mice were treated with an immunomodulatory drug (iv injection with 0.5 mg/kg OKT3, 10 mg/kg KEYTRUDA, 1 mg/kg ATG, or 5 ml/kg PBS (negative control)). Cytokine levels were determined in mouse blood obtained six hours after the drug treatment. The results comparing drug-induced cytokine level in the irradiated and non-irradiated humanized mice are shown in FIGS. 22A-22B. FIG. 22A presents the data for IFN-γ(panel a), IL-10 (panel b), and IL-6 (panel c), while FIG. 22B presents the data for IL-2 (panel d), IL-4 (panel e), and TNF (panel f). FIGS. 22A-22B show that for each cytokine, in either donor, the cytokine levels in the non-irradiated mice are consistently lower after a given drug treatment as compared to those determined in the irradiated mice after the same drug treatment.

The higher cytokine levels produced in the irradiated mice are likely due to the higher number of human immune cells (T cells and NK cells) present in those mice, as disclosed in Example 16. Thus, the irradiated humanized mouse model provides greater sensitivity for detection of individual variation in immunostimulation in response to a given drug.

Materials & Methods

1. PBMCs Humanized Mice Reconstitution

Six weeks old female NOD.Cg-Prkdc$^{scid}$Il2rg$^{tm1wjl}$/SzJ (NSG, JAX stock number 005557) mice and their derivatives, NSG-CSF-1, NSG-IL-6 mice were irradiated with 100 cGy X-ray at least 4 hours before human PBMCs engraftment. Purified human PBMCs were commercially purchased (Astarte Biologics or Allcells technologies). The PBMCs were washed twice with PBS after thawing, then intravenously (i.v.) injected to NSG mice with 10-50 million cells/mouse. Following hPBMCs injection, mice were observed daily for general appearance of the fur, and mobility. On a different day after the hPBMCs engraftment, mice were bled for testing human cells percentage by flow cytometry. The mouse PBMCs were stained with human anti-CD45, anti-CD3, anti-CD14, anti-CD19, anti-CD56.

2. Inducement and measurement of cytokines release in humanized mice

On day 6 of hPBMCs engraftment, the mice were induced human cytokines release by iv injected with antibodies OKT3 (anti-CD3 mAb) and ANC28 (anti-CD28 mAb), KEYTRUDA® (pembrolizumab) (anti-PD-1), ATG, REVLIMID® (lenalidomide) and PBS buffer as a baseline control. The mice were bled at 2 and/or 6 hours, serum was collected and analyzed for cytokines concentration using BD Cytometric Bead Array (CBA) Human Th1/Th2 Cytokine kit II (BD Cat. No. 551809). The limits of detection of the present assays for the various cytokines are as follows: IFN-γ, 7 pg/ml; IL-2, 2.6 pg/ml; IL-4, 2.6 pg/ml; IL-6, 3.0 pg/ml; IL-10, 2.8 pg/ml; and TNF, 2.8 pg/ml.

3. Measurement of Body Temperature

Rectal temperature of the mice was measured before treatment and again immediately before each time-point bleed. Temperature was measured by the insertion of a rectal thermocouple probe and waiting until a stable reading was obtained.

4. Evaluation of Clinical Score

As in a reference by Brady et al., Clinical & Translational Immunology, 2014, the inventors performed the signs and the grading of scores as follow: Score: 0=normal activity; 1=normal activity, piloerection, tiptoe gait; 2=hunched, reduced activity but still mobile; 3=hypomotile but mobile when prompted; 4=moribund (point of death). Mice with a clinical score of 4 were euthanized 5. Statistical analysis Results were analyzed using GraphPad Prism 5.0.

This disclosure further encompasses the following aspects.

Aspect 1. A method of determining whether an immunomodulatory drug likely elicits a severe cytokine release syndrome in a human following administration of the immunomodulatory drug, said method comprising: (a) providing an immunodeficient mouse, said mouse is irradiated with 75-125 cGy X-ray; (b) engrafting $1.5-3.0 \times 10^7$ peripheral blood mononuclear cells (PBMCs) isolated from a human to said mouse; (c) administering to said mouse an immunomodulatory drug 5-7 days after engrafting with the PBMCs; (d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and (e) determining said immunomodulatory drug likely elicits a severe cytokine release syndrome in said human, wherein presence of a severe cytokine release syndrome in said mouse is indicative that administration of said immunomodulatory drug likely elicits a severe cytokine release syndrome in said human.

Aspect 2. A method of determining likelihood that administration of an immunomodulatory drug to a human will induce a severe cytokine release syndrome in the human, the method comprising: (a) providing a blood sample from a humanized, irradiated, immunodeficient mouse administered an immunomodulatory drug 5-7 days after engraftment with $1.5-3.0 \times 10^7$ isolated peripheral blood mononuclear cells (PBMCs) from a human; and (b) detecting in vitro the concentration of a plurality of cytokines comprising IFN-γ and/or IL-10 present in the blood sample of the mouse, wherein a concentration of IFN-γ≥1,800 pg/ml or of IL-10≥120 pg/ml in the mouse blood sample is indicative that administration of the immunomodulatory drug to the human is likely to induce a severe cytokine release syndrome.

Aspect 3. A method of determining whether a combination of a first immunomodulatory drug and a second immunomodulatory drug likely elicits a severe cytokine release syndrome in a human following administration of said combination of immunomodulatory drugs, said method comprising: (a) providing an immunodeficient mouse, said mouse is irradiated with 75-125 cGy X-ray; (b) engrafting $1.5-3.0 \times 10^7$ peripheral blood mononuclear cells (PBMCs) isolated from a human to said mouse; (c) administering to said mouse a first immunomodulatory drug and a second immunomodulatory drug 5-7 days after engrafting with the PBMCs; (d) determining blood concentration in said mouse of a plurality of cytokines comprising IFN-γ and IL-10, wherein blood concentration of IFN-γ≥1,800 pg/ml and IL-10≥120 pg/ml is indicative of a severe cytokine release syndrome in said mouse; and (e) determining said combination of immunomodulatory drugs likely elicits a severe cytokine release syndrome in said human, wherein presence of a severe cytokine release syndrome in said mouse is indicative that administration of said combination of immunomodulatory drugs likely elicits a severe cytokine release syndrome in said human.

Aspect 4. A method of determining likelihood that administration of a combination of a first immunomodulatory drug and a second immunomodulatory drug to a human will induce a severe cytokine release syndrome in the human, the method comprising:(a) providing a blood sample from a humanized irradiated immunodeficient mouse administered a combination of a first immunomodulatory drug and a second immunomodulatory drug 5-7 days after engraftment with $1.5-3.0 \times 10^7$ isolated peripheral blood mononuclear cells (PBMCs) from a human; and (b)

detecting in vitro the concentration of a plurality of cytokines comprising IFN-γ and/or IL-10 present in the blood sample of the mouse, wherein a concentration of IFN-γ≥1,800 pg/ml or of IL-10≥120 pg/ml is indicative that administration of the combination of the first immunomodulatory drug and the second immunomodulatory drug to the human is likely to induce a severe cytokine release syndrome.

Aspect 5. A method of determining a safe dosage of an immunomodulatory drug that elicits no cytokine release syndrome in a human following administration of the immunomodulatory drug, said method comprising: (a) providing an immunomodulatory drug having a first dosage, said first dosage of the immunomodulatory drug is determined to elicit a mild or severe cytokine release syndrome in a first humanized irradiated immunodeficient mouse following its administration; (b) providing a second immunodeficient mouse, said second mouse is irradiated with 75-125 cGy X-ray; (c) engrafting $1.5-3.0 \times 10^7$ peripheral blood mononuclear cells (PBMCs) isolated from a human to said second mouse; (d) administering to said second mouse an immunomodulatory drug 5-7 days after engrafting with the PBMCs, said immunomodulatory drug is administered at a second dosage that is lower than said first dosage; (e) determining blood concentration in said second mouse of a plurality of cytokines comprising IFN-γ and IL-10; and (f) determining a safe dosage of said immunomodulatory drug for administration in said human, said safe dosage is a dosage producing a blood concentration of IFN-γ is <300 pg/ml and IL-10 is <25 pg/ml following administration of said immunomodulatory drug. to said second mouse, wherein blood concentration of IFN-γ<300 pg/ml and IL-10<25 pg/ml in said second mouse is indicative that administration of said safe dosage of said immunomodulatory drug likely elicits no cytokine release syndrome in said human.

Aspect 6. A method of determining immunotoxicity of a drug candidate for use in a human, said method comprising: (a) providing an immunodeficient mouse, said mouse is irradiated with 75-125 cGy X-ray; (b) engrafting 4.5-5.5×$10^7$ of human PBMCs to said mouse; (c) administering a drug candidate to said mouse 4-7 days after engrafting; (d) determining cytokine concentration in blood of said mouse, wherein said cytokine is at least one cytokine selected from the group consisting of IFN-γ, IL-2, IL-4, IL-6, IL-10, and TNF; and (e) determining immunotoxicity of said drug candidate, wherein blood concentration in said mouse of at least one cytokine selected from the group consisting of: IFN-γ≥300 pg/ml, IL-2≥15 pg/ml, IL-4≥10 pg/ml, IL-6≥10 pg/ml, IL-10≥25 pg/ml, or TNF≥5 pg/ml, is indicative of an immunotoxicity of said drug candidate in a human.

Aspect 7. A method of determining immunotoxicity of a drug candidate in a human, the method comprising: (a) providing a blood sample from a humanized, irradiated, immunodeficient mouse administered a drug candidate 4-7 days after engraftment with 4.5-5.5×$10^7$ isolated human peripheral blood mononuclear cells (PBMCs); and (b) detecting in vitro the concentration of at least one human cytokine present in the mouse blood sample to determine human immunotoxicity of the drug candidate, wherein the at least one human cytokine is selected from the group consisting of IFN-γ, IL-2, IL-4, IL-6, IL-10, and TNF and wherein the drug candidate has low human immunotoxicity when low human cytokine concentration is detected in the mouse blood sample.

Aspect 8. The method of any one of aspects 1 to 7, wherein said mouse is an NSG, NSG-IL-6, or NSG-CSF-1 mouse.

Aspect 9. The method of any one of aspects 1 to 8, wherein said mouse is an NSG mouse.

Aspect 10. The method of any one of aspects 1 to 9, wherein said mouse is irradiated with 100 cGy X-ray.

Aspect 11. The method of any one of aspects 1 to 5 and 8-10, wherein said engrafting step is performed with 2×$10^7$ PBMCs.

Aspect 12. The method of any one of aspects 1 to 11, wherein said administering step is performed 6 days after engrafting.

Aspect 13. The method of any one of aspects 1 to 12, wherein said plurality of cytokines further comprises IL-2, IL-4, IL-6, and TNF.

Aspect 14. The method of any one of aspects 1 to 13, wherein blood concentration of plurality of cytokines is determined 2 to 6 hours following administration of said immunomodulatory drug or said combination of immunomodulatory drugs.

Aspect 15. The method of any one of aspects 1 to 14, wherein blood concentration of plurality of cytokines is determined 6 hours following administration of said immunomodulatory drug or said combination of immunomodulatory drugs.

Aspect 16. The method of any one of aspects 1 to 15, wherein said immunomodulatory drug is selected from the group consisting of an anti-CD28 monoclonal antibody (mAb), an anti-CD3 mAb, an anti-CD20 mAb, an anti-CD52 mAb; granulocyte colony-stimulating factor (G-CSF); an interferon; imiquimod; thalidomide, lenalidomide, pomalidomide, apremilast; azathioprine, cladribine, cyclophosphamide, intravenous immunoglobulin, methotrexate, mitoxantrone; talimogene laherparepvec; adalimumab, catumaxomab, ibritumomab tiuxetan, tositumomab-$I^{131}$, brentuximab vedotin, betuximab, rituximab, alemtuzumab, bevacizumab, pertuzumab, trastuzumab, trastuzumab emtansinen, denosumab, ofatumumab, panitumumab, pembrolizumab, nivolumab, ipilimumab, atezolizumab, avelumab, durvalumab, daratumumab, ceritinib, elotuzumab, and anti-thymocyte globulin.

Aspect 17. The method of aspect 16, wherein said anti-CD28 mAb is TGN1412.

Aspect 18. The method of aspect 16, wherein said anti-CD3 mAb is OKT3.

Aspect 19. The method of aspect 16, wherein said anti-C20 mAb is rituximab.

Aspect 20. The method of aspect 16, wherein said anti-CD52 mAb is alemtuzumab.

Aspect 21. The method of any one of aspects 3 to 4 and 5-15, wherein said first immunomodulatory drug and said second immunomodulatory are independently selected from the group consisting of an anti-CD28 monoclonal antibody (mAb), an anti-CD3 mAb, an anti-CD20 mAb, an anti-CD52 mAb; granulocyte colony-stimulating factor (G-CSF); an interferon; imiquimod; thalidomide, lenalidomide, pomalidomide), apremilast; azathioprine, cladribine, cyclophosphamide, intravenous immunoglobulin, methotrexate, mitoxantrone; talimogene laherparepvec; adalimumab, catumaxomab, ibritumomab tiuxetan, tositumomab-$I^{131}$, brentuximab vedotin, betuximab, rituximab, alemtuzumab, bevacizumab, pertuzumab, trastuzumab, trastuzumab emtansinen, denosumab, ofatumumab, panitumumab, pembrolizumab, nivolumab, ipilimumab, atezolizumab, avelumab), durvalumab, daratumumab, ceritinib, elotuzumab, and anti-thymocyte globulin.

Aspect 22. The method of any one of aspects 3 to 4, 5-15, and 21, wherein said first immunomodulatory drug is pembrolizumab or nivolumab; and said second immunomodulatory drug is lenalidomide, pomalidomide, epacadostat, talimogene laherparepvec, ipilimumab, atezolizumab, avelumab, rituximab, alemtuzumab, ceritinib, daratumumab, or durvalumab.

Aspect 22. The method of any one of aspects 3 to 4, 5-15, and 21, wherein said first immunomodulatory drug is ipilimumab and said second immunomodulatory drug is lenalidomide, pomalidomide, pembrolizumab, atezolizumab, avelumab, rituximab, alemtuzumab, ceritinib, daratumumab, or durvalumab.

Aspect 23. The method of any one of aspects 3 to 4, 5-15, and 21, wherein said first immunomodulatory drug is atezolizumab, avelumab, or durvalumab and said second immunomodulatory drug is lenalidomide, pomalidomide, pembrolizumab, ipilimumab, rituximab, ceritinib, daratumumab, or alemtuzumab.

Aspect 24. The method of aspect of any one of aspects 3 to 4, 5-15, and 21, wherein said anti-CD52 mAb is alemtuzumab, said anti-C20 mAb is rituximab, said anti-CD3 mAb is OKT3, or said anti-CD28 mAb is TGN1412.

Aspect 25. The method of aspect 6 or 7, wherein said engrafting step (b) is performed with 5×$10^7$ PBMCs.

Any publications or references mentioned in this specification are indicative of the level of those skilled in the art to which the invention pertains. All patents, publications, and/or references herein are incorporated by reference to the same extent as if each individual publication was specifically and individually indicated as having been incorporated by reference in its entirety.

While example embodiments are described herein with respect to using humanized immunosuppressed mice to determine if immunomodulatory drugs may be administered to a human without eliciting an unacceptably high cytokine response in the human, it should be understood that the present methods may be used with various mammals and/or drugs, and/or may be used to treat mammals other than humans. Therefore, the present invention is not limited to the present examples. In view of the teachings provided herein, one having ordinary skill in the art would recognize other applications for which the present invention could be used. Thus, one having ordinary skill in the art would be able to use the methods of the present invention in other applications. Accordingly, these alternative uses are intended to be part of the present invention.

In the foregoing specification, the invention has been described with reference to specific embodiments thereof. It will, however, be evident that various modifications and changes may be made thereto without departing from the broader spirit and scope of the invention. Accordingly, it is intended that such changes and modifications fall within the scope of the present invention as defined by the claims appended hereto. The specification and drawings are, accordingly, to be regarded in an illustrative rather than restrictive sense.

What is claimed is:

1. A method for assessing immune toxicity of an immunomodulatory agent on a human immune system, the method comprising:
   (a) subjecting an immunodeficient mouse to myeloablation;
   (b) administering $1.5 \times 10^7$-$3.0 \times 10^7$ human peripheral blood mononuclear cells (PBMCs) to the immunodeficient mouse;
   (c) administering an immunomodulatory agent to the immunodeficient mouse fewer than 8 days after the administering of the human PBMCs;
   (d) measuring blood concentration of a human cytokine selected from interferon-gamma (IFN-γ), interleukin (IL)-10, IL-6, IL-2, IL-4, and tumor necrosis factor alpha (TNFα) in a sample from the immunodeficient mouse, within 24 hours of the administering of the immunomodulatory agent,
   (e) determining severity of cytokine release induced by the immunomodulatory agent based on a comparison of the blood concentration of the human cytokine to a threshold value; and
   (f) assessing immune toxicity of the immunomodulatory agent on the human immune system based on the severity of cytokine release.

2. The method of claim 1, wherein the myeloablation comprises irradiation.

3. The method of claim 1, wherein the immunodeficient mouse has a non-obese diabetic (NOD) severe combined immunodeficiency (scid) gamma genetic background.

4. The method of claim 1, wherein the administering of the human PBMCs comprises administering $2.0 \times 10^7$ human PBMCs to the immunodeficient mouse.

5. The method of claim 1, wherein the administering of the immunomodulatory agent to the immunodeficient mouse is 4-7 days after administering the human PBMCs.

6. The method of claim 5, wherein the administering of the immunomodulatory agent to the immunodeficient mouse is 5-7 days after administering the human PBMCs.

7. The method of claim 1, wherein the measuring is 2 to 6 hours following the administering of the immunomodulatory agent.

8. The method of claim 1, wherein the immunomodulatory agent is selected from immunostimulating drugs.

9. The method of claim 1, wherein the immunomodulatory agent is selected from antibodies.

10. The method of claim 9, wherein the antibodies are selected from monoclonal antibodies.

11. The method of claim 1, wherein the immunomodulatory agent is selected from granulocyte colony-stimulating factor (G-CSF), interferons, imiquimod, thalidomide and its derivatives or analogues, lenalidomide, pomalidomide, apremilast, azathioprine, cladribine, cyclophosphamide, intravenous immunoglobulin, methotrexate, mitoxantrone, talimogene laherparepvec, a genetically modified oncolytic viral therapy, daratumumab, an antiCD38 antibody, adalimumab, elotuzumab, epacadostat, an orally available hydroxyamidine inhibitor of indoleamine 2,3-dioxygenase (ID01), catumaxomab, ibritumomab tiuxetan, tositumomab-I131, brentuximab vedotin, betuximab, rituximab, alemtuzumab, bevacizumab, pertuzumab, trastuzumab, trastuzumab emtansinen, denosumab, ipilimumab, ofatumumab, and panitumumab.

12. The method of claim 1, wherein the immunomodulatory agent is selected from checkpoint inhibitors.

13. The method of claim 12, wherein the checkpoint inhibitors are selected from cytotoxic T lymphocyte antigen-4 (CTLA-4) inhibitors, programmed death-1 (PD-1) inhibitors, and programmed death-ligand 1 (PD-L1) inhibitors.

14. The method of claim 13, wherein the checkpoint inhibitors are selected from ipilimumab, pembrolizumab, nivolumab, atezolizumab, avelumab, and durvalumab.

15. The method of claim 1, wherein the threshold value for IFN-γ, IL-10, IL-6, IL-2, IL-4, and TNFα is respectively 1,800 pg/ml, 120 pg/ml, 25 pg/ml, 80 pg/ml, 25 pg/ml, and 20 pg/ml.

* * * * *